United States Patent
Kornbluth et al.

(10) Patent No.: US 10,238,734 B2
(45) Date of Patent: Mar. 26, 2019

(54) COMPOSITIONS AND METHODS FOR SELF-ADJUVANTING VACCINES AGAINST MICROBES AND TUMORS

(75) Inventors: Richard Syd Kornbluth, La Jolla, CA (US); Geoffrey William Stone, Coral Gables, FL (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/635,885

(22) PCT Filed: Mar. 22, 2011

(86) PCT No.: PCT/US2011/029458
§ 371 (c)(1),
(2), (4) Date: Nov. 9, 2012

(87) PCT Pub. No.: WO2011/119628
PCT Pub. Date: Sep. 29, 2011

(65) Prior Publication Data
US 2013/0039942 A1    Feb. 14, 2013

Related U.S. Application Data

(60) Provisional application No. 61/340,843, filed on Mar. 23, 2010.

(51) Int. Cl.
| | | |
|---|---|---|
| *A61K 39/00* | (2006.01) | |
| *A61K 39/39* | (2006.01) | |
| *C12N 15/86* | (2006.01) | |
| *A61K 35/763* | (2015.01) | |
| *C07K 14/005* | (2006.01) | |
| *C07K 14/705* | (2006.01) | |

(52) U.S. Cl.
CPC ............ *A61K 39/39* (2013.01); *A61K 35/763* (2013.01); *C07K 14/005* (2013.01); *C07K 14/70578* (2013.01); *C12N 15/86* (2013.01); *A61K 2039/5256* (2013.01); *A61K 2039/55516* (2013.01); *C07K 2319/03* (2013.01); *C12N 2710/16222* (2013.01); *C12N 2710/16632* (2013.01); *C12N 2710/24143* (2013.01); *C12N 2740/15011* (2013.01); *C12N 2740/16011* (2013.01)

(58) Field of Classification Search
CPC .......................... A61K 2300/00; A61K 39/12; A61K 39/0011; A61K 39/245; A61K 2039/53; A61K 38/162; A61K 35/763; A61K 2039/522; A61K 2039/525; A61K 2039/58; A61K 35/76; C12N 7/00; C12N 15/86; C12N 2710/16234; C12N 2710/16222; C12N 2710/16211; C12N 2710/16232; C12N 2710/16233; C07K 14/005; C07K 2319/00; C07K 14/70578; C07K 16/087; C07K 14/045

See application file for complete search history.

(56) References Cited

U.S. PATENT DOCUMENTS

| | | | |
|---|---|---|---|
| 6,306,401 B1* | 10/2001 | Brown et al. .............. | 424/218.1 |
| 6,544,781 B1* | 4/2003 | Jiang ..................... | C12N 15/86 |
| | | | 435/320.1 |
| 6,589,533 B1* | 7/2003 | Brown et al. .............. | 424/205.1 |
| 7,335,363 B2* | 2/2008 | Hernandez et al. ....... | 424/199.1 |
| 7,387,271 B2 | 6/2008 | Noelle et al. | |
| 7,803,378 B2 | 9/2010 | Tranchand-Bunel | |
| 8,329,162 B2* | 12/2012 | Wang et al. ................. | 424/93.2 |
| 2003/0212028 A1* | 11/2003 | Raz et al. ........................ | 514/44 |
| 2004/0141950 A1 | 7/2004 | Noelle et al. | |
| 2005/0158831 A1* | 7/2005 | Kornbluth .................... | 435/69.5 |
| 2007/0048329 A1* | 3/2007 | Khanna ............... | C07K 14/005 |
| | | | 424/186.1 |
| 2008/0019998 A1* | 1/2008 | Wang et al. ............... | 424/199.1 |
| 2008/0075717 A1 | 3/2008 | Tranchand-Bunel | |
| 2009/0081157 A1* | 3/2009 | Kornbluth et al. .......... | 424/85.2 |
| 2009/0202584 A1* | 8/2009 | Thomson et al. ........ | 424/196.11 |
| 2009/0263348 A1* | 10/2009 | Kornbluth .................... | 424/85.1 |
| 2010/0255030 A1* | 10/2010 | Kinney et al. ............. | 424/202.1 |
| 2010/0270202 A1* | 10/2010 | Guy et al. ....................... | 206/570 |
| 2010/0278773 A1* | 11/2010 | Chambers et al. .......... | 424/85.2 |
| 2010/0291144 A1* | 11/2010 | Ramanathan et al. ..... | 424/208.1 |
| 2011/0111502 A1* | 5/2011 | Saint-Remy ................. | 435/377 |

(Continued)

OTHER PUBLICATIONS

Latham T, Galarza JM. Formation of wild-type and chimeric influenza virus-like particles following simultaneous expression of only four structural proteins. J Virol. Jul. 2001;75(13):6154-65.*

Chen XY, Zhang G, Liu F, Li HL, Fang WY, Jiang QP, Zhao T. [Construction and identification of a recombinant lentivirus vector of latent membrane protein 1]. Nan Fang Yi Ke Da Xue Xue Bao. May 2009;29(5):837-40. Chinese.*

Dullaers M, Van Meirvenne S, Heirman C, Straetman L, Bonehill A, Aerts JL, Thielemans K, Breckpot K. Induction of effective therapeutic antitumor immunity by direct in vivo administration of lentiviral vectors. Gene Ther. Apr. 2006;13(7):630-40.*

(Continued)

*Primary Examiner* — Rachel B Gill
(74) *Attorney, Agent, or Firm* — DLA Piper LLP (US)

(57) ABSTRACT

The present invention is drawn to compositions and methods to enhance an immune response in order to prevent or treat infections or hyperproliferative diseases such as cancer. More particularly, the composition is an immunostimulatory intracellular signaling peptide fused directly or indirectly to a peptide that leads to multimerization into complexes of three or more units, where the intracelluar signaling peptide must be present in a complex of three or more units in order to stimulate an immune response. Inserting this fusion construct into viruses like HIV-1 or introducing it into dendritic cells or tumor cells is predicted to lead to a positive therapeutic effect in humans, non-human mammals, birds, and fish.

39 Claims, 32 Drawing Sheets
Specification includes a Sequence Listing.

(56) References Cited

U.S. PATENT DOCUMENTS

| | | | |
|---|---|---|---|
| 2011/0236421 A1* | 9/2011 | Brown et al. | 424/218.1 |
| 2012/0263754 A1* | 10/2012 | Dubensky et al. | 424/204.1 |
| 2013/0202634 A1* | 8/2013 | Shresta et al. | 424/186.1 |
| 2013/0216575 A1* | 8/2013 | Coller et al. | 424/218.1 |
| 2013/0243812 A1* | 9/2013 | Pugachev | 424/199.1 |
| 2013/0323278 A1* | 12/2013 | Chambers | 424/205.1 |
| 2014/0024081 A1* | 1/2014 | Smith et al. | 435/91.3 |
| 2015/0232812 A1 | 8/2015 | Coffin | |

OTHER PUBLICATIONS

Breckpot K, Aerts JL, Thielemans K. Lentiviral vectors for cancer immunotherapy: transforming infectious particles into therapeutics. Gene Ther. Jun. 2007;14(11):847-62. Epub Mar. 22, 2007.*

Dai B, Yang L, Yang H, Hu B, Baltimore D, Wang P. HIV-1 Gag-specific immunity induced by a lentivector-based vaccine directed to dendritic cells. Proc Natl Acad Sci U S A. Dec. 1, 2009;106(48):20382-7. doi: 10.1073/pnas.0911742106. Epub Nov. 16, 2009.*

Schroers R, Chen SY. Lentiviral transduction of human dendritic cells. Methods Mol Biol. 2004;246:451-9.*

Lutzky VP, Corban M, Heslop L, Morrison LE, Crooks P, Hall DF, Coman WB, Thomson SA, Moss DJ. Novel approach to the formulation of an Epstein-Barr virus antigen-based nasopharyngeal carcinoma vaccine. J Virol. Jan. 2010;84(1):407-17. Epub Oct. 21, 2009.*

Gupta S, Termini JM, Niu L, Kanagavelu SK, Schmidtmayerova H, Snarsky V, Kornbluth RS, Stone GW. EBV LMP1, a viral mimic of CD40, activates dendritic cells and functions as a molecular adjuvant when incorporated into an HIV vaccine. J Leukoc Biol. Aug. 2011;90(2):389-98. doi: 10.1189/jlb.0211068. Epub May 17, 2011.*

Terrin L, Dal Col J, Rampazzo E, Zancai P, Pedrotti M, Ammirabile G, Bergamin S, Rizzo S, Dolcetti R, De Rossi A. Latent membrane protein 1 of Epstein-Barr virus activates the hTERT promoter and enhances telomerase activity in B lymphocytes. J Virol. Oct. 2008;82(20):10175-87. doi: 10.1128/JVI.00321-08. Epub Aug. 6, 2008.*

System Biosciences. "Lentivector Expression Systems: Guide to Packaging and Transduction of Target Cells." User Manual. Ver. 071510, Jul. 15, 2010.*

Matthews TJ, Lyerly HK, Weinhold KJ, Langlois AJ, Rusche J, Putney SD, GalloRC, Bolognesi DP. Prospects for development of a vaccine against HTLV-III-related disorders. AIDS Res Hum Retroviruses. 1987;3 Suppl 1:197-206.*

Desrosiers RC. Prospects for an AIDS vaccine. Nat Med. Mar. 2004;10(3):221-3.*

Wang F. Nonhuman primate models for Epstein-Barr virus infection. Curr Opin Virol. Jun. 2013;3(3):233-7. Epub Apr. 3, 2013.*

Chen XY, et. al. Construction and Identification of a Recombinant Lentivirus Vector of Latent Membrane Protein 1. English translation. J South Med Univ. vol. 29 (5): 837-840. 2009.*

Buchman AR, Berg P. Comparison of intron-dependent and intron-independent gene expression. Mol Cell Biol. Oct. 1988; 8(10):4395-405.*

Lu S, Cullen BR. Analysis of the stimulatory effect of splicing on mRNA production and utilization in mammalian cells. RNA. May 2003;9(5):618-30.*

Li KJ, Garoff H. Packaging of intron-containing genes into retrovirus vectors by alphavirus vectors. Proc Natl Acad Sci U S A. Mar. 31, 1998;95(7):3650-4.*

Price MA, Case SS, Carbonaro DA, Yu XJ, Petersen D, Sabo KM, Curran MA, Engel BC, Margarian H, Abkowitz JL, Nolan GP, Kohn DB, Crooks GM. Expression from second-generation feline immunodeficiency virus vectors is impaired in human hematopoietic cells. Mol Ther. Nov. 2002;6(5):645-52.*

"Principles of Retroviral Vector Design." In "Retroviruses". Coffin JM, Hughes SH, Varmus HE, editors. Cold Spring Harbor (NY): Cold Spring Harbor Laboratory Press; 1997.*

Munis JR, Kornbluth RS, Guatelli JC, Richman DD. Ordered appearance of human immunodeficiency virus type 1 nucleic acids following high multiplicity infection of macrophages. J Gen Virol. Aug. 1992;73 ( Pt 8):1899-906.*

Levy DN, Aldrovandi GM, Kutsch O, Shaw GM. Dynamics of HIV-1 recombination in its natural target cells. Proc Natl Acad Sci U S A. Mar. 23, 2004;101(12):4204-9. Epub Mar. 9, 2004. Erratum in: Proc Natl Acad Sci U S A. Feb. 1, 2005;102(5):1808.*

The WayBack Machine. www.clontech.com website from May 18, 1998 regarding Living Colors proteins such as GFP. https://web.archive.org/web/19980517164409/http://www.clontech.com/clontech/Catalog/GeneExpression/PDF/GFPintro.pdf.*

Graham JP, Moore CR, Bishop GA. Roles of the TRAF2/3 binding site in differential B cell signaling by CD40 and its viral oncogenic mimic, LMP1. J Immunol. Sep. 1, 2009;183(5):2966-73. doi: 10.4049/jimmunol.0900442. Epub Aug. 10, 2009.*

Nott A, Meislin SH, Moore MJ. A quantitative analysis of intron effects on mammalian gene expression. RNA. May 2003;9(5):607-17.*

Van Maanen M, Tidwell JK, Donehower LA, Sutton RE. Development of an HIV-based cDNA expression cloning system. Mol Ther. Jul. 2003;8(1):167-73.*

Hatzivassiliou et al., "A Fusion of the EBV Latent Membrane Protein-1 (LMP1) Transmembrane Domains to the CD40 Cytoplasmic Domain is Similar to LMP1 in Constitutive Activation of Epidermal Growth Factor Receptor Expression, Nuclear Factor-κb, and Stress-Activated Protein Kinase," *J. Immunol.* (1998), 160:1116-1121, The American Association of Immunologists, Bethesda, Maryland.

Panagopoulos et al., "Comparative Analysis of Signal Transduction by CD4O and the Epstein-Barr V," *J. Virol.* (2004), 78(23):13253-13261, American Society for Microbiology.

Stone Geoffrey W et al: "Multimeric soluble CD40 ligand and GITR ligand as adjuvants for human immunodeficiency virus DNA vaccines", Journal of Virology, vol. 80, No. 4, Feb. 2006 (Feb. 2006), pp. 1762-1772, XP002711225, ISSN: 0022-538X.

Saravana K Kanagavelu et al: "Soluble multi-trimeric TNF superfamily ligand adjuvants enhance immune responses to a HIV-1 Gag DNA vaccine", Vaccine, Elsevier Ltd, GB, vol. 30, No. 4, Nov. 22, 2011 (Nov. 22, 2011), pp. 691-702, XP028434514, ISSN: 0264-410X, DOI: 10.1016/J.VACCINE.2011.11.088, (retrieved on Nov. 28, 2011).

Gupta Sachin et al: "Latent Membrane Protein 1 as a molecular adjuvant for single-cycle lentiviral vaccines", Retrovirology, vol. 8, May 2011 (May 2011), XP002711226.

European Search Report regarding application No. EP 11 76 0085.

Meij, P., et al. (1999). Restricted low-level human antibody responses against Epstein-Barr virus (EBV)-encoded latent membrane protein 1 in a subgroup of patients with EBV-associated diseases: The Journal of Infectious Diseases, 179(5), 1108-1115.

Zhang, B., et al. (2012). Immune Surveillance and Therapy of Lymphomas Driven by Epstein-Barr Virus Protein LMP1 in a Mouse Model: Cell, 148(4, 739-751.

Mosiaios, George et al.: "*The Epstein-Barr Virus Transforming Protein LMP1 Engages Signaling Proteins for the Tumor Necrosis Factor Receptor Family*": Cell, vol. 80, Feb. 10, 1995, pp. 389-399.

Hanks, B.A. et al.: "*Re-engineered CD40 receptor enables potent pharmacological activation of dendritic-cell cancer vaccines in vivo*"; Nat Med., Feb. 11, 2005, (2):130-7.

Kaykas, A. et al.: "*CD40 and LMP-1 both signal from lipid rafts but LMP-1 assembles a distinct, more efficient signaling complex*"; EMBO J., Jun 1, 2001; 20(11)2641-54.

Koya, R. C. et al: "*Potent maturation of monocyte-derived dendritic cells after CD4OL lentiviral gene delivery*"; J Immunother., Sep.-Oct. 2003; 26(5):451-60.

Aghi, M. et al.: "*Oncolytic herpes virus with defective ICP6 specifically replicates in quiescent cells with homozygous genetic mutations in p16*"; Oncogene, Jul. 10, 2008; 27(30): pp. 4249-4254.

Desai, P. J. et al.: "*Excretion of non-infectious virus particles lacking glycoprotein H by a temperature-sensitive mutant of herpes simplex virus type 1: evidence that gH is essential for virion infectivity*"; J Gen Virol., Jun. 1988, vol. 69, pp. 1147-1156.

(56) References Cited

OTHER PUBLICATIONS

Rowe, Martin et al.: "*Restoration of endogenous antigen processing in Burkitt's lymphoma cells by Epstein-Barr virus latent membrane protein-1: coordinate up-regulation of peptide transporters and HLA-class I antigen expression*"; Eur. J. Immunol., 1995, vol. 25: pp. 1374-1384.

Smith, Corey et al.: "*Discerning regulation of cis- and trans-presentation of CD8 T-cell epitopes by EBV-encoded oncogene LMP-1 through self-aggregation*"; Blood, Jun. 11, 2009, vol. 113, No. 24, pp. 6148-6152.

\* cited by examiner

Infect DC with HIV virus and culture 6 days

Coculture DC with autologous T cells for 12 days in the presence of nevirapine.

Perform ELISPOT, restimulating T cells with Gag 15-mer peptide pool.

Infect DC with scSIV virus and culture 4 days
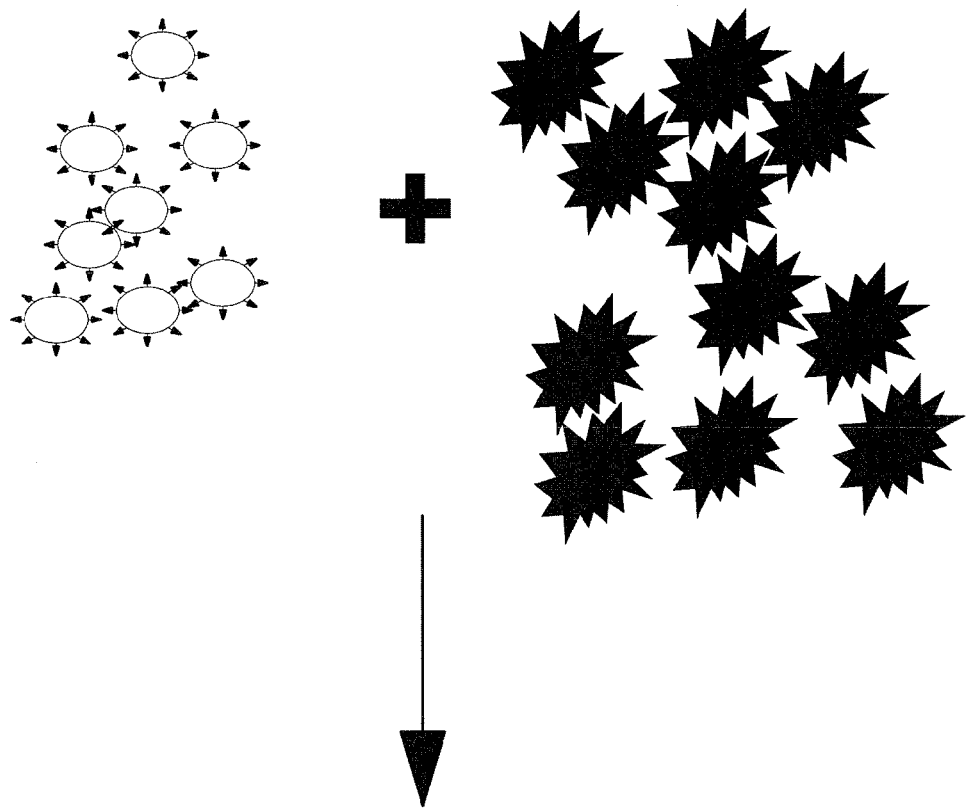
Coculture DC with autologous T cells for 12 days in the presence of nevirapine.
Perform ELISPOT, restimulating T cells with Gag 15–mer peptide pool.

COMPOSITIONS AND METHODS FOR SELF-ADJUVANTING VACCINES AGAINST MICROBES AND TUMORS

CROSS-REFERENCE TO RELATED APPLICATIONS

This application is a 35 USC § 371 National Stage application of International Application No. PCT/US2011/029458 filed Mar. 22, 2011, now expired; which claims the benefit under 35 USC § 119(e) to U.S. Application Ser. No. 61/340,843 filed Mar. 23, 2010. The disclosure of each of the prior applications is considered part of and is incorporated by reference in the disclosure of this application.

GRANT INFORMATION

This invention was made in part with government support under Grant Nos. 1R21AI078834, 1K22AI068489, 1R21AI63982 and 1R21AI973240 awarded by the National Institutes of Health. The United States government has certain rights in this invention.

BACKGROUND OF THE INVENTION

Field of the Invention

The present invention relates generally to compositions and methods for improved immune response to prevent or treat infections or hyperproliferative diseases such as cancer, and more specifically to compositions and methods for self-adjuvanting vaccines against microbes and tumors.

Background Information

Immune responses are highly desirable when they protect the body from infection by a microorganism or control the growth of tumors and other hyperproliferative disorders. To generate an immune response, three components are needed: (1) an antigen; (2) an adjuvant; and (3) a delivery method. The most common means for generating an immune response is by administering a vaccine. In the case of the tetanus vaccine, the antigen is heat-inactivated tetanus toxoid protein, the adjuvant is alum (i.e., hydrated aluminum potassium sulfate), and the delivery method is the needle and syringe used for the subcutaneous or intramuscular injection.

For other kinds of vaccines, notably viral vaccines such as measles, mumps, rubella, polio, and varicella vaccines, a live, replicating virus is used. The live virus is typically attenuated or weakened as part of its selection and production, but the live virus vaccine contains both the viral antigens (proteins, carbohydrates, or lipids from the virus) along with the means of delivery. In this case, the delivery component is intrinsic to the ability of the virus to enter cells, partially or completely replicate, and thereby lead to the generation of its antigens in the host. The live virus vaccine can also carry its own adjuvant and thereby elicit a strong immune response. A good example of this is the Yellow Fever vaccine 17D in which the live virus vaccine is capable of interacting with Toll-Like Receptors (TLRs) on dendritic cells and other antigen-presenting cells, thereby activating these cells to initiate and amplify an immune response.

On the other hand, some vaccines fail to provide sufficient adjuvant activity. A good example is the live replicating viral vaccine for Respiratory Syncytial Virus (RSV). About half of all children are infected by RSV during their first year of life. However, a formalin-fixed RSV virus vaccine failed to protect children. This was subsequently traced to an inability of the vaccine to provide the appropriate adjuvant activity, specifically the activation of TLRs on antigen-presenting cells. Conversely, if TLR agonists were added to the ineffective RSV vaccine, it became sufficient to elicit strong protective immune responses.

As the example of the RSV vaccine demonstrates, there is a need in the field to provide an adjuvant when the vaccine atone is insufficient for stimulating antigen-presenting cells. Sometimes this can be provided by mixing an adjuvant with the vaccine, such as mixing the MF59 adjuvant with the vaccine for influenza. However, this approach is not suitable for all situations.

In many cases, there is a need for a method to provide the antigen and the adjuvant co-extensive in space and time. To do this, it is preferable to incorporate the adjuvant into the vaccine formulation. For example, the Yellow Fever 17D vaccine incorporates the viral antigens, the TLR agonist adjuvants, and the delivery method (cell entry mediated by viral proteins) into a single entity. As such, the antigen and adjuvant are provided co-extensive in space and time.

SUMMARY OF THE INVENTION

The present invention provides compositions and methods to enhance an immune response in order to prevent or treat infections or hyperproliferative diseases such as cancer. More particularly, the composition is an immunostimulatory intracellular signaling peptide fused directly or indirectly to a peptide that leads to multimerization into complexes of three or more units, where the intracellular signaling peptide must be present in a complex of three or more units in order to stimulate an immune response.

In one embodiment, the present invention provides an isolated protein including a multimerizing domain operatively joined to a cytoplasmic signaling domain of a receptor such that the protein assembles into a complex of three or more protein moieties. In one aspect, the protein moieties activate a desired biological effect in cells.

In one aspect, the multimerizing domain includes an N-terminus fragment or portion of latent membrane protein 1 (LMP1). In another aspect, the cytoplasmic signaling domain includes a cytoplasmic fragment or portion of a member of Tumor necrosis factor receptor superfamily (TNFRSF). In another aspect, the cytoplasmic signaling domain includes a cytoplasmic fragment or portion selected from CD40, CD27, Fas, lymphotoxin beta receptor (LTBR), nerve growth factor receptor (NGFR), Tumor necrosis factor receptor superfamily member 1A (TNFRSF1A), Tumor necrosis factor receptor superfamily member 1B (TNFRSF1B), Tumor necrosis factor receptor superfamily member 4 (TNFRSF4), Tumor necrosis factor receptor superfamily member 8 (TNFRSF8), Tumor necrosis factor receptor superfamily member 9 (TNFRSF9), Tumor necrosis factor receptor superfamily member 10A (TNFRSF10A), Tumor necrosis factor receptor superfamily member 10B (TNFRSF10B), Tumor necrosis factor receptor superfamily member lap (TNFRSF10D), Tumor necrosis factor receptor superfamily member 11A (TNFRSF11A), Tumor necrosis factor receptor superfamily member 12A (TNFRSF12A), Tumor necrosis factor receptor superfamily member 13B (TNFRSF3), Tumor necrosis factor receptor superfamily member 13C (TNFRSF13C), Tumor necrosis factor receptor superfamily member 14 (TNFRSF14), Tumor necrosis factor receptor superfamily member 17 (TNFRSF17), Tumor necrosis factor receptor superfamily member 18 (TNFRSF18), Tumor necrosis factor receptor superfamily member 19 (TNFRSF19), Tumor necrosis factor receptor superfamily member 21 (TNFRSF21), or Tumor necrosis factor receptor superfamily member 25 (TNFRSF25).

In one aspect, the cell signaling domain includes the cytoplasmic domain of a Latency Membrane Protein 1 (LMP1) of Epstein-Barr virus (EBV) CD40. In another aspect, the multimerizing domain includes at least four transmembrane regions. In another aspect, the multimerizing domain includes about four to six transmembrane regions. In another aspect, the protein includes a Latency Membrane Protein (LMP1) or LMP1-CD40 fusion protein.

In another embodiment, the present invention provides an isolated virus, microbe, or host cell. The isolated virus, microbe, or host cell includes a first expression cassette for expressing the protein as described herein, and a second expression cassette for expressing an antigen. In one aspect, the isolated virus, microbe, or host cell is with the proviso that the virus, microbe, or host cell does not include or contain an Epstein-Barr virus (EBV).

In one aspect, the antigen expressed by the virus, microbe, or host cell gains cell stimulatory activities from the cytoplasmic signaling domain. In another aspect, the protein includes (a) a multimerizing domain including an N-terminus fragment or portion of latent membrane protein 1 (LMP1); and/or (b) a cytoplasmic signaling domain including a cytoplasmic fragment or portion of a member of Tumor necrosis factor receptor superfamily (TNFRSF).

In one aspect, the protein includes a Latency Membrane Protein 1 (LMP1) or LMP1-CD40 fusion protein. In another aspect, the isolated virus, microbe, or host cell includes a DNA virus or RNA virus. In one aspect, the isolated virus, microbe, or host cell includes a microbe selected from Human immunodeficiency virus-1 (HIV-1), Simian immunodeficiency virus (SIV), influenza virus, parainfluenza virus, dengue virus, Hepatitis A virus, Hepatitis B, virus, Hepatitis C virus, Cytomegalovirus (CMV), adenovirus, adeno-associated virus, Simian virus 40 (SV40), Modified Vaccinia Ankara (MVA), Vesicular stomatitis virus (VSV), arenaviruses, bunyaviruses, flaviviruses, West Nile virus, Japanese Encephalitis virus, Venezuelan equine encephalitis virus, Eastern equine encephalitis virus, Western equine encephalitis virus, herpesviruses, measles virus, rhabdoviruses, *Listeria, Salmonella*, or combinations thereof. In another aspect, the isolated virus, microbe, or host cell includes a replication-incompetent single-cycle virus. In another aspect, the antigen includes a tumor antigen, viral antigen, or microbial antigen. In another embodiment, the present invention provides a DNA virus or RNA virus that expresses the isolated (protein of claim 1 in cells transduced by that virus.

In another embodiment, the present invention provides a vaccine composition including (a) an antigen including a tumor antigen, viral antigen, or microbial antigen; (b) an adjuvant including the protein as described herein; and (c) a delivery system including a microorganism.

In one aspect, the protein includes (a) a multimerizing domain including an N-terminus fragment or portion of latent membrane protein 1 (LMP1); and/or (b) a cytoplasmic signaling domain including a cytoplasmic fragment or portion of a member of Tumor necrosis factor receptor superfamily (TNFRSF). In another aspect, the protein includes a Latency Membrane Protein 1 (LMP1) or LMP1-CD40 fusion protein.

In one aspect, the delivery system includes a DNA virus, RNA virus, or prokaryotic organism. In another aspect, the delivery system includes a tumor-associated virus. In another aspect, the delivery system includes a virus selected from the group consisting of Human immunodeficiency virus-1 (HIV-1), Simian immunodeficiency virus (SIV), influenza virus, parainfluenza virus, dengue virus, Hepatitis A virus, Hepatitis B, virus, Hepatitis C virus, Cytomegalovirus (CMV), adenovirus, adeno-associated virus, Simian virus 40 (SV40), Modified Vaccinia Ankara (MVA), Vesicular stomatitis virus (VSV), arenaviruses, bunyaviruses, flaviviruses, West Nile virus, Japanese Encephalitis virus, Venezuelan equine encephalitis virus, Eastern equine encephalitis virus, Western equine encephalitis virus, herpesviruses, measles virus, rhabdoviruses, *Listeria, Salmonella*, or combinations thereof.

In another embodiment, the present invention provides a method for stimulating an immune response or preventing/treating cancer or an infectious disease in a subject. The method includes administering to a cell an effective amount of a polynucleotide including a first expression cassette for expressing the protein as described herein, and/or a second expression cassette for expressing an antigen. If the malignant or infected cell already expresses the targeted antigen(s), then the immune response against that antigen(s) may be stimulated by administering only the protein as described herein.

In one aspect, at least two nucleic acid sequences are administered, where a first nucleic acid sequence includes the first expression cassette for expressing the protein as described herein, and a second nucleic acid sequence includes the second expression cassette for expressing an antigen. These nucleic acid sequences may be delivered separately (e.g., in separate polynucleotide molecules or plasmids) or operatively linked (e.g., in a single polynucleotide molecule or plasmid). In another aspect, the nucleic acid includes a DNA vaccine. In another aspect, the nucleic acid includes an in vitro synthesized and optionally modified RNA molecule. In one aspect, the nucleic acid includes (a) a multimerizing domain including an N-terminus fragment or portion of latent membrane protein 1 (LMP1) and/or (b) a cytoplasmic signaling domain including a cytoplasmic fragment or portion of a member of Tumor necrosis factor receptor superfamily (TNFRSF). In another aspect, the protein includes a Latency Membrane Protein 1 (LMP1) or LMP1-CD40 fusion protein. In one aspect, the antigen includes a tumor antigen, viral antigen, or microbial antigen. In another aspect, the subject is mammalian. In an additional aspect, the subject is human.

In another embodiment, the present invention provides an avirulent, oncolytic herpes simplex virus having an intact $U_S12$ gene and an endogenous $U_S11$ gene expressed as a late gene, wherein the virus is modified from the wild-type herpes simplex virus with both $\gamma_1 34.5$ genes of the virus being deleted and $U_S11$ genes that are expressed as immediate-early (IE) genes being inserted into the $\gamma_1 34.5$ gene locus in place of both $\gamma_1 34.5$ genes; wherein the virus includes an expression cassette for expressing the protein as described herein.

In another embodiment, the present invention provides a herpes simplex virus 1 (HSV1) strain, which is modified such that it lacks one or more of a functional ICP34.5-encoding gene, a functional ICP6-encoding gene, a functional glycoprotein H-encoding gene and a functional thymidine kinase-encoding gene, and which is derived from HSV1 strain JS1 as deposited at the European Collection of Cell Cultures (ECACC) under accession number 01010209 wherein the virus includes an expression cassette for expressing the protein as described herein.

In another embodiment, the present invention provides a herpes simplex virus which: (i) includes a gene encoding an immunostimulatory protein; (ii) lacks a functional ICP34.5 encoding gene and a functional ICP47 encoding gene; (iii) is replication competent in tumor cells; and (iv) is derived from HSV1 JS1 as deposited at the European collection of cell cultures (ECAAC) under accession number 01010209; wherein the virus includes an expression cassette for expressing the protein as described herein.

In another embodiment, the present invention provides a modified, oncolytic herpes simplex virus (HSV) strain including: a modified, oncolytic herpes simplex virus (HSV) strain wherein the HSV strain is a clinical isolate from a recurrent cold sore and has a greater ability than a reference laboratory HSV strain modified in the same manner as the clinical isolate to replicate in or kill tumor cells, and wherein the reference laboratory HSV strain is selected from the group consisting of HSV1 strain 17+, HSV1 strain F and HSV1 strain KOS; wherein the virus includes an expression cassette for expressing the protein as described herein.

In another embodiment, the present invention provides a method of treating cancer in subject. The method includes administering to the subject an effective amount of an oncolytic virus wherein the virus includes an expression cassette for expressing the protein as described herein. In one aspect, the oncolytic virus is selected from a Newcastle Disease Virus, a Mumps Virus, a Measles Virus, a Vesicular Stomatitis Virus, a Parainfluenza Virus, an Influenza Virus, an Adenovirus, a Herpes 1 Virus, a Vaccinia Virus, a Reovirus, a Seneca Valley virus, an Alphavirus, Sindbis virus, or a combination thereof. In another aspect, the virus is selected from any virus described herein.

In another embodiment, the present invention provides a modified, oncolytic herpes simplex virus 1 strain (HSV1), wherein the oncolytic (HSV1) strain is a clinical isolate from a recurrent cold sore modified such that it lacks a function ICP34.5-encoding gene, wherein the modified clinical isolate has a greater ability than a reference laboratory HSV strain modified in the same manner as the clinical isolate to replicate in or kill tumor cells, and wherein the reference laboratory strain is selected from the group consisting of HSV1 strain 17+, HSV1 strain F and HSV1 strain KOS; wherein the virus includes an expression cassette for expressing the protein as described herein.

In another embodiment, the present invention provides a herpes virus which lacks a functional ICP34.5 encoding gene and which includes two or more of: (i) a heterologous gene encoding a prodrug converting enzyme; (ii) heterologous gene encoding a protein capable of causing cell to cell fusion; and (iii) a heterologous gene encoding an immunomodulatory protein; wherein the virus includes an expression cassette for expressing the protein as described herein.

In another embodiment, the present invention provides a method of treating cancer in a subject in need thereof by administering to a tumor in the subject a therapeutically effective amount of a herpes simplex virus which: (i) includes an immunostimulatory protein; (ii) lacks a functional ICP34.5 encoding gene and a functional ICP47 encoding gene; and (iii) is replication competent in infected tumor cells; wherein the virus includes an expression cassette for expressing the protein as described herein.

In another embodiment, the present invention provides a method of stimulating an immune response in a human or animal subject, which method includes administering to a subject in need thereof an effective amount of an attenuated herpes virus which: (i) lacks a functional vhs gene, or a functional equivalent thereof; (ii) lacks a functional gene encoding ICP47, or a functional equivalent thereof; and (iii) includes a functional UL43 gene, or a functional equivalent thereof such that dendritic cells are infected with the virus; wherein the virus includes an expression cassette for expressing the protein as described herein.

In another embodiment, the present invention provides a method of stimulating an immune response in a human or animal subject, which method includes administering to a subject in need thereof an effective amount of an attenuated herpes virus capable of efficiently infecting a dendritic cell without preventing antigen processing occurring within the infected cell, wherein the virus contains mutations which prevent or minimize the expression of viral immediate early genes in the infected cell; wherein the virus includes an expression cassette for expressing the protein as described herein.

In another embodiment, the present invention provides a method of stimulating an immune response in a human or animal subject, which method includes administering to a subject in need thereof an effective amount of an attenuated herpes virus which: (i) lacks a functional vhs gene, or a functional equivalent thereof; (ii) lacks a functional gene encoding ICP47, or a functional equivalent thereof; and (iii) includes a functional UL43 gene, or a functional equivalent thereof such that dendritic cells are infected with the virus; wherein the virus includes an expression cassette for expressing the protein as described herein.

In another embodiment, the present invention provides a method of stimulating an immune response in a human or animal subject, which method includes administering to a subject in need thereof an effective amount of an attenuated herpes virus which: (i) lacks a functional vhs gene, or a functional equivalent thereof; (ii) lacks a functional ICP47 gene, or a functional equivalent thereof; and (iii) is incapable of expressing a substantial amount of functional ICP22, or a functional equivalent thereof, in mammalian dendritic cells; wherein the virus includes an expression cassette for expressing the protein as described herein.

In another embodiment, the invention provides a method of preparing a self-adjuvanting vaccine using a microorganism. In one aspect, the method uses a microorganism into whose genome has been modified by the introduction of a multimerizing-intracellular signaling gene cassette into the genome of the microorganism. The method includes introducing a multimerizing-intracellular signaling gene cassette into the genome of the microorganism. In one aspect, the method further includes delivering the genome of the microorganism into a subject. In another aspect, the method further includes delivering the genetically modified microorganism into a subject. In an additional aspect, the genetic modification comprises a multimerizing-intracellular signaling gene cassette expresses LMP1 or LMP1-CD40. In another aspect, the multimerizing-intracellular signaling gene cassette expresses LMP1 or LMP1-CD40. In another aspect, the microorganism includes a virus or bacterium. In an additional aspect, the microorganism is *Listeria* or *Salmonella*. In another aspect, the microorganism includes an oncolytic virus. In another aspect, the multimerizing-intracellular signaling gene cassette includes a cytoplasmic domain of a death receptor like Fas or Trail receptor. In another aspect, the genome of the microorganism is delivered into a cell of the subject ex vivo or in vitro. In another aspect, the microorganism is a nucleic acid transferring bacterium. In another aspect, the genome of the microorganism is delivered into an arm of a human. In another aspect, the microorganism is a pathogen.

In another embodiment, the invention provides the use of the protein described above in the manufacture of a medicament for treatment or prevention of cancer or an infectious disease in a subject. In one aspect, the protein includes an N-terminus fragment or portion of latent membrane protein 1 (LMP1) fused with a cytoplasmic signaling domain. In another embodiment, the invention provides a protein as described herein for use in a method for treatment or prevention of cancer or an infectious disease in a subject.

The foregoing has outlined rather broadly the features and technical advantages of the present invention in order that the detailed description of the invention that follows may be better understood. Additional features and advantages of the invention will be described hereinafter. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing.

In LMP1, the 6 transmembrane N-terminal regions enable the formation of LMP1 clusters in the plasma membrane. This clustering is essential for LMP1 activity. In the LMP1-CD40 fusion protein, the cell signaling C-terminal region of LMP1 has been replaced with the signaling domain of the CD40 receptor.

Figure 2:
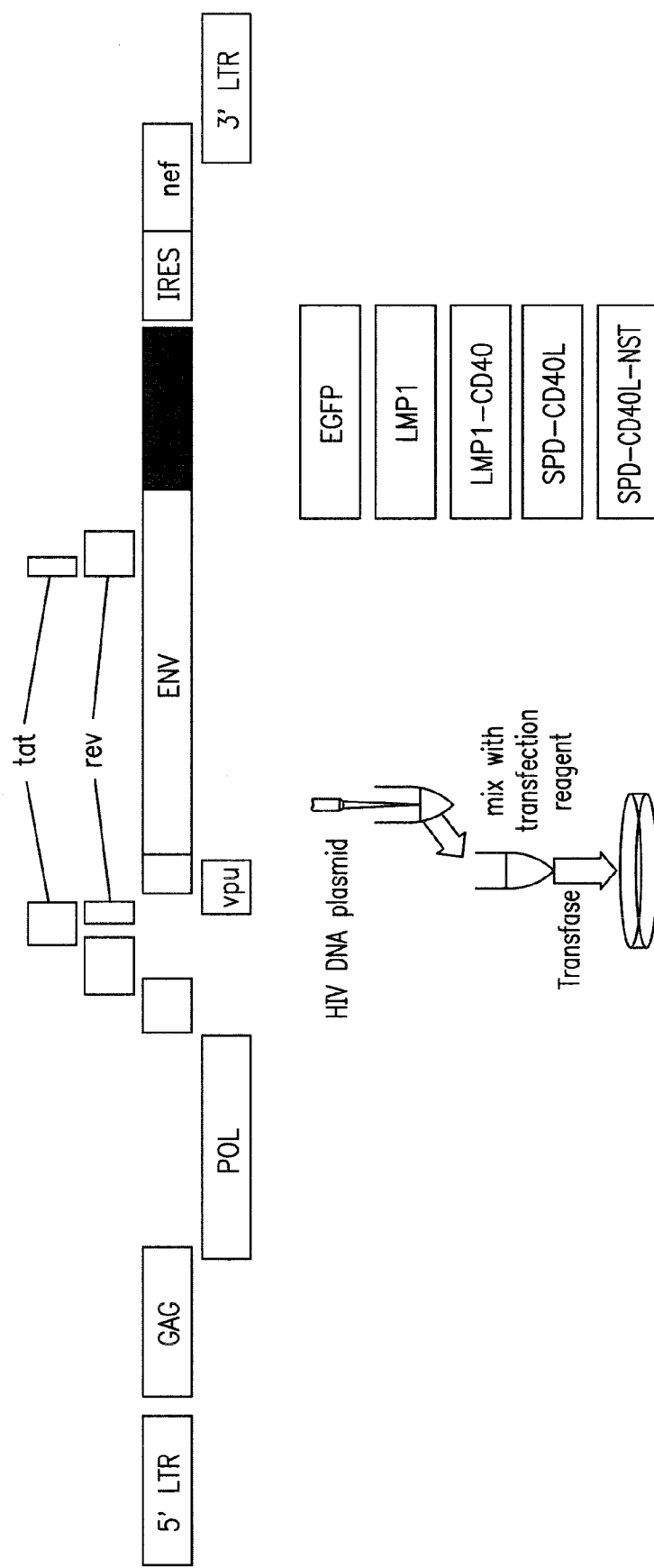

FIG. 2 shows exemplary construction of live, replicating LMP1- and LMP1-CD40-expressing HIV-1. In the proviral plasmid clone, pNL4-3BaL, a coding sequence for enhanced green fluorescent protein (EGFP) can be inserted into the HIV-1 sequence just after the env reading frame and before the nef start codon. This is followed by an internal ribosomal entry sequence (IRES) placed just before the nef sequence, such that Nef protein is also produced. As a consequence of this design, a live, replicating virus is encoded by this nucleic acid sequence (Levy et al. (2004) Proc Natl Acad Sci USA 101: 4204-9). In the present invention, the EGFP coding sequence is replaced with either LMP1 or LMP1-CD40. As controls, secreted multimeric soluble forms of CD40L formed by fusion with surfactant protein D (SP-D-CD40L), a variant termed SP-D-CD40L-NST, and a secreted multimeric soluble form of Glucocorticoid-induced tumor necrosis factor receptor ligand (GITRL) are also introduced into the EGFP site.

Figure 3:
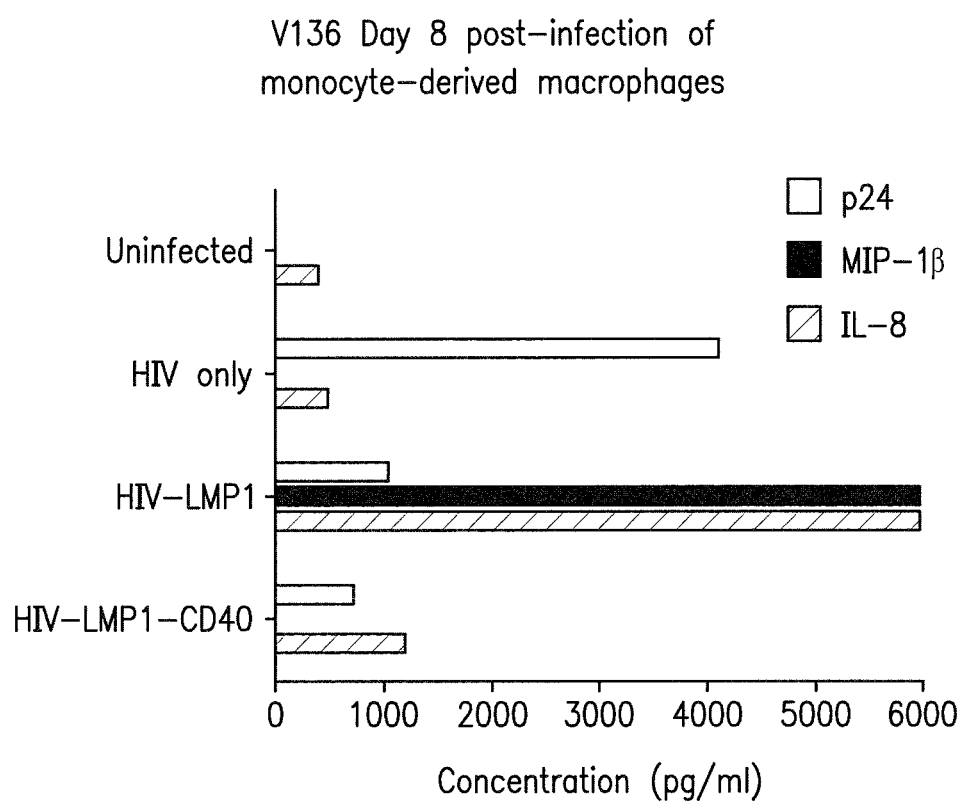

FIG. 3 shows replication in and stimulation of human monocyte-derived macrophages by LMP1- and LMP1-CD40-expressing HIV-1. Referring to FIG. 2, three plasmids are used: one for the unmodified proviral plasmid clone, pNL4-3BaL, containing the EGFP sequence just 5' to the IRES-nef portion of the sequence; the same plasmid except replacing the EGFP sequence with LMP1 just 5' to the IRES-nef portion of the sequence; and the same plasmid except replacing the EGFP sequence with LMP1-CD40 just 5' to the IRES-nef portion of the sequence. To produce live virus from these plasmids, the plasmids are transfected into 293T cells using the calcium phosphate method. Forty-eight hours later, virus containing supernatants are harvested and used to infect human monocyte-derived macrophages (MDM) in culture. By flow cytometry 48 hours post infection, about 10% of the MDM became EGFP positive, an indicator of cellular infection. At the same time, supernatants are harvested and assayed by ELISA for p24 Gag (as a measure of new progeny virus production), the chemokine macrophage inflammatory protein 1-beta (MIP-1β, also designated CCL4), and interleukin-8 (IL-8) which is a cytokine. As shown in the figure, progeny virus (p24) is best produced by macrophages infected by the original pNL4-3/BaL clone (labeled "HIV only" in the figure) and to a lesser extent by macrophages infected with the HIV-1 viruses carrying LMP1 (labeled "HIV-LMP1") or LMP1-CD40 (labeled "HIV-LMP1-CD40"). However, the original pNL4-3/BaL clone (labeled "HIV only") does not trigger the production of MIP-1β and the infected macrophages produced only small amounts of IL-8. In contrast, macrophages infected by the LMP1 containing virus (labeled "HIV-LMP1") produces large amounts of MIP-1β and IL-8 (outside the range of the ELISA) whereas macrophages infected by the LMP-CD40 containing virus (labeled "HIV-LMP1") produced no detectable MIP-1β and above background levels of IL-8. This experiment demonstrates the surprising result that a virus like HIV-1 that normally does not stimulate target cells like macrophages can be engineered to stimulate these cells if a multimerization-intracytoplasmic signaling cassette (e.g., LMP1 or LMP1-CD40) is inserted into and expressed by the virus. In this example, the resulting engineered virus can still replicate in its target cells.

FIG. 4 shows further studies on the stimulation of human monocyte-derived macrophages by LMP1- and LMP1-CD40-expressing HIV-1. In a subsequent study similar to FIG. 3 above, monocyte-derived macrophages are infected with virus and cultured for 9 days until cellular infection is well-established. Supernatants are collected and cytokines are measured. As shown, NL4-3/BaL virus engineered to express LMP1 (“NL4-Bal-LMP1”) stimulates macrophages to produce IL-8, IL-1β, IL-6, IL-12p70, and TNFα, but does not increase the production of IL-10, which is an immunosuppressive cytokine. NL4-3/BaL virus engineered to express LMP1-CD40 (“NL4-Bal-LMP1-CD40”) has a similar effect on macrophages in culture, with some fine differences noted. As controls, NL4-3/BaL virus expressing EGFP (“NL4-Bal-EGFP”) and wild-type NL4-3/BaL virus (“NL4-Bal”) have similar effects on macrophages as media alone (“Mock”).

Figure 5:
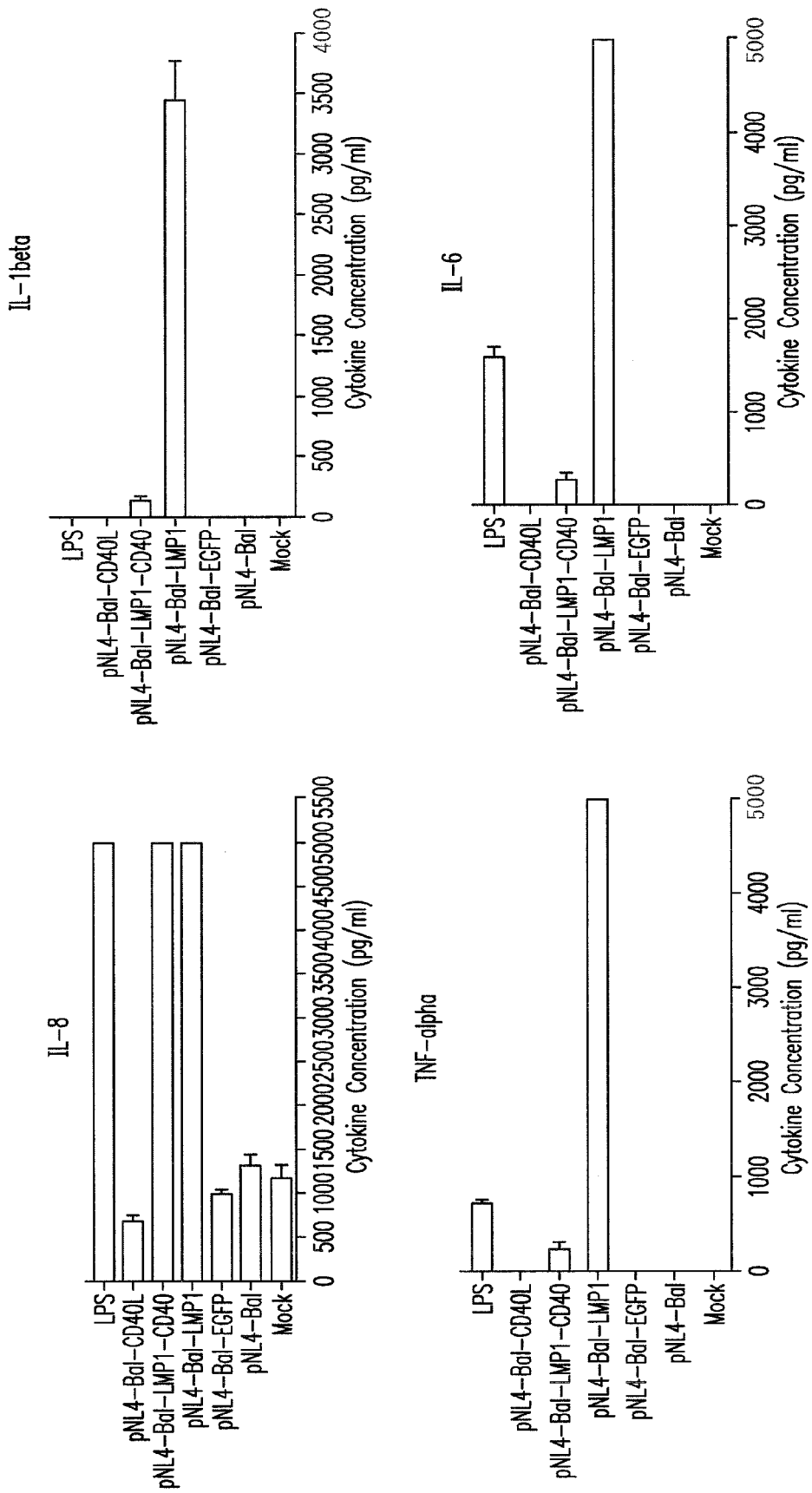

FIG. 5 shows stimulation of human monocyte-derived dendritic cells by LMP1- and LMP1-CD40-expressing HIV-1. Dendritic cells (DCs) are considered to be the primary antigen-presenting cell for T cells. To produce DCs for study, blood monocytes are isolated from human venous blood and cultured in GM-CSF/IL-4 for 6 days by standard methods by which time they have differentiated into DCs. Then the cultured DCs are infected with various forms of the NL4-3/Bat clone of HIV-1 at a multiplicity of infection (MOI) of 0.1 and the culture supernatant is collected 9 days later and assayed for the presence of cytokines. Bacterial lipopolysaccharide (LPS) from *E. coli* B011 (100 ng/ml) is used as a positive control. In human DCs, LMP1 is able to stimulate the production of IL-8, IL-1β, TNFα, and IL-6, whereas LMP1-CD40 is only able to stimulate the production of IL-8. Although the virus used here is capable of replicating in other target cells, there is little production of progeny virus as measured by the release of p24 Gag into the supernatant. The surprising result of these data is that a composition of the present invention comprised of a multimerization-intracellular signaling cassette can be used to stimulate DCs, a key type of antigen-presenting cell.

Figure 6:
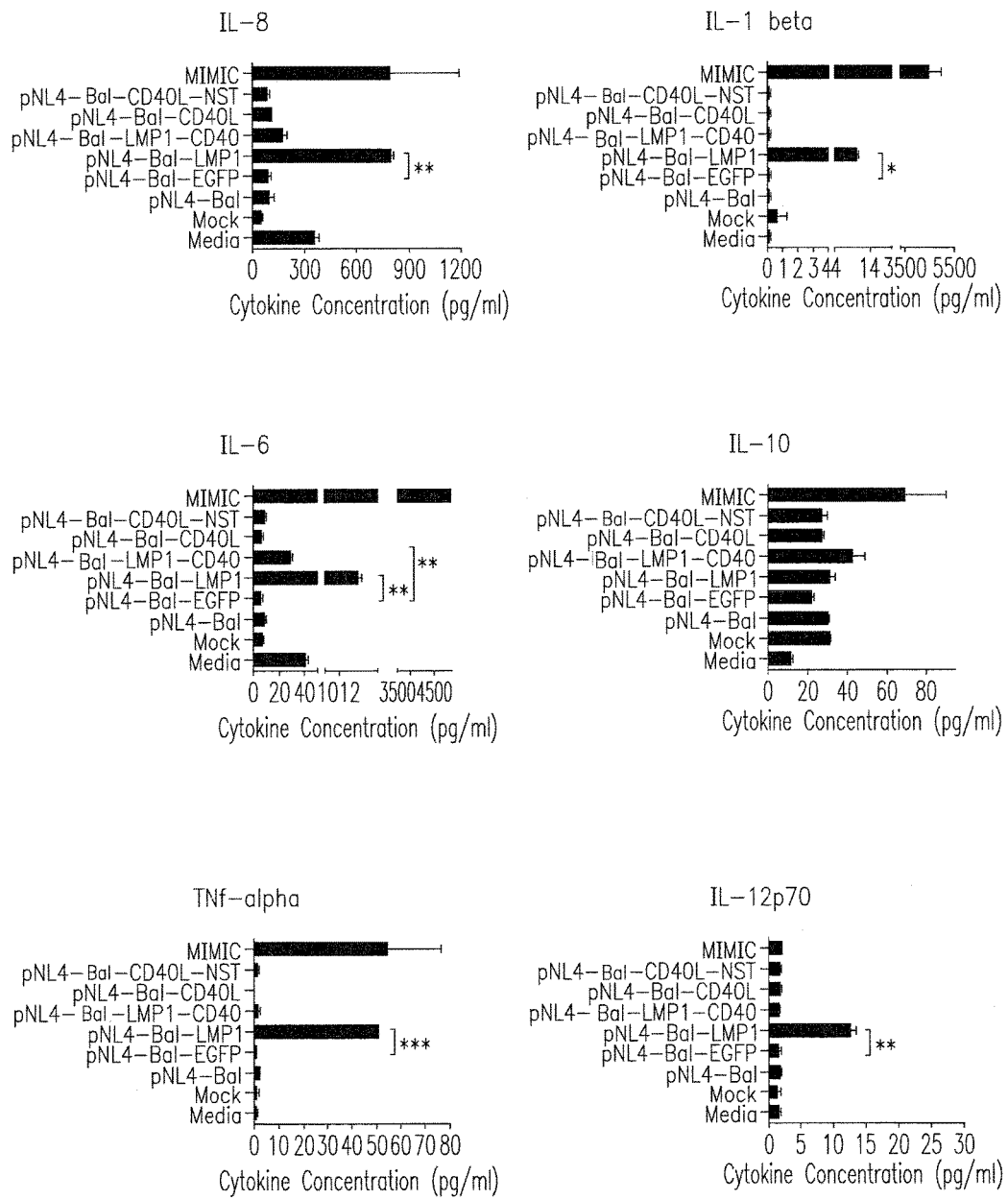

FIG. 6 shows further studies on the stimulation of human monocyte-derived dendritic cells by LMP1- and LMP1-CD40-expressing HIV-1. As in FIG. 5, DCs are infected with various NL4-3/BaL HIV-1 viral constructs. Controls include virus engineered to express the viral clone lacking EGFP ("pNL4-Bal") or a secreted form of multimeric CD40L (SP-D-CD40L) abbreviated "pNL4-BaL-CD40L" or a similar protein (SP-D-CD40L-NST wherein the stalk region of CD40L is absent and a human tPA signal sequence is used) abbreviated "pNL4-BaL-CD40L-NST". In this experiment, the positive control is MIMIC™ (Clontech, Palo Alto, Calif.), a cytokine mix designed to stimulate DCs. As shown, the LMP1-expressing virus stimulated DCs to produce IL-8, IL-1β, TNFα, IL-12p70, and IL-6. In contrast, the LMP1-CD40-expressing virus stimulates DCs to produce IL-6. Neither the LMP1-nor the LMP1-CD40-expressing virus induced DCs to produce IL-10, an immunosuppressive cytokine, at levels above background.

Figure 7:
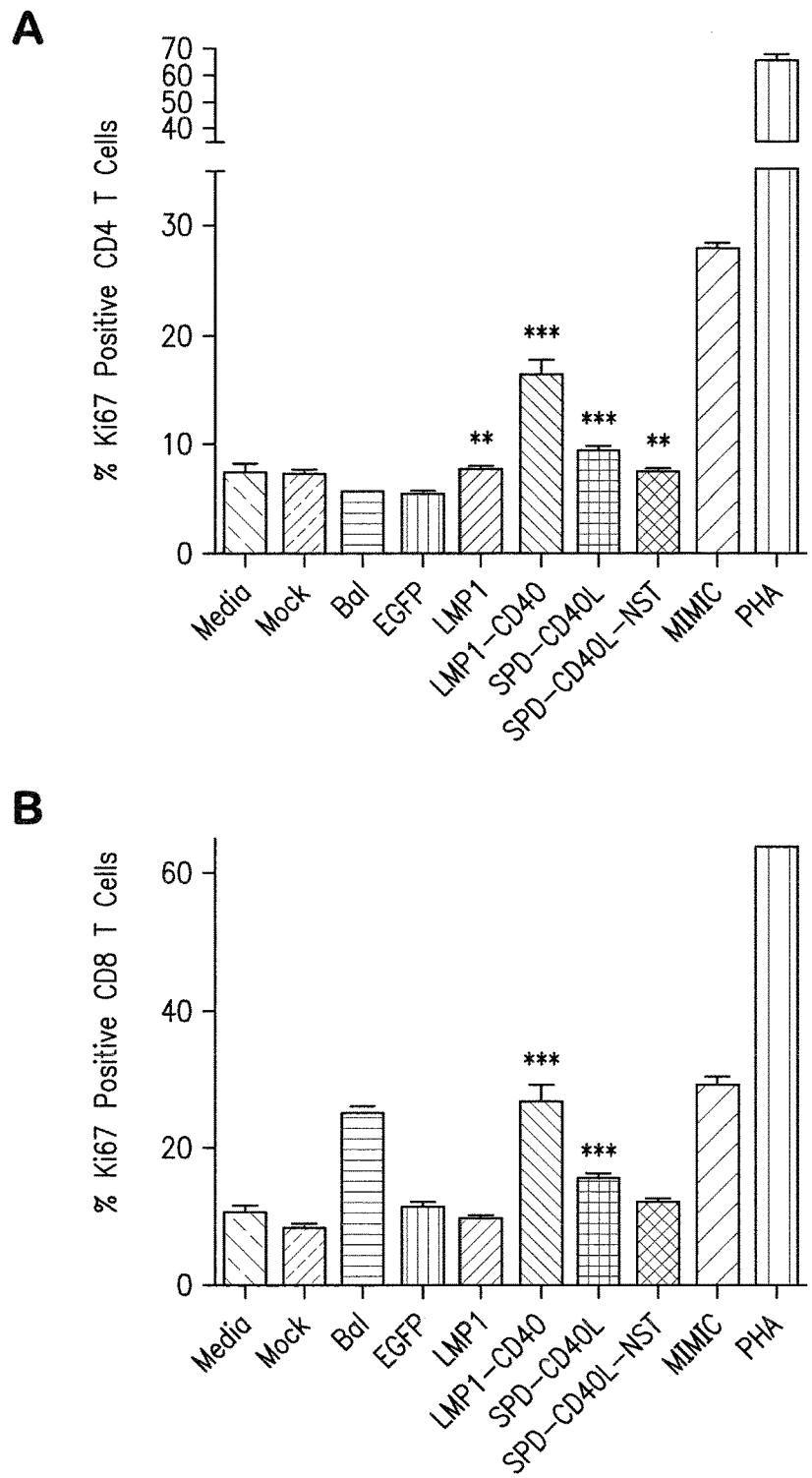

FIG. 7 shows that LMP1-CD40-expressing HIV-1 stimulates DCs to present antigen. The mixed leukocyte reaction (MLR) is a classic test of the presentation and response to foreign antigens. Consequently, dendritic cells are infected with the various HIV-1 constructs for 5 days. Then peripheral blood mononuclear cells (PBMCs) from a second donor are added along with nevirapine to prevent HIV-1 infection from spreading to the added CD4+ T cells. After 5 days of MLR culture, the T cells are stained for either CD4 (top) or CD8 (bottom) and analyzed for intracellular ki67 as a marker for entry into the cell cycle and proliferation. As shown, the most prominent effects in the MLR-responding population are in CD4+ and CD8+ T cells co-cultured with DCs exposed to the LMP1-CD40-expressing HIV-1 virus. Controls using HIV-1 that expresses soluble multimeric forms of CD40L (SP-D-CD40L and SP-D-CD40L-NST) or GITRL (SP-D-GITRL) also have some stimulatory effects. * p<0.05,  p<0.01, * p<0.001 compared to control virus NL4-3/BaL-EGFP.

Figure 8:
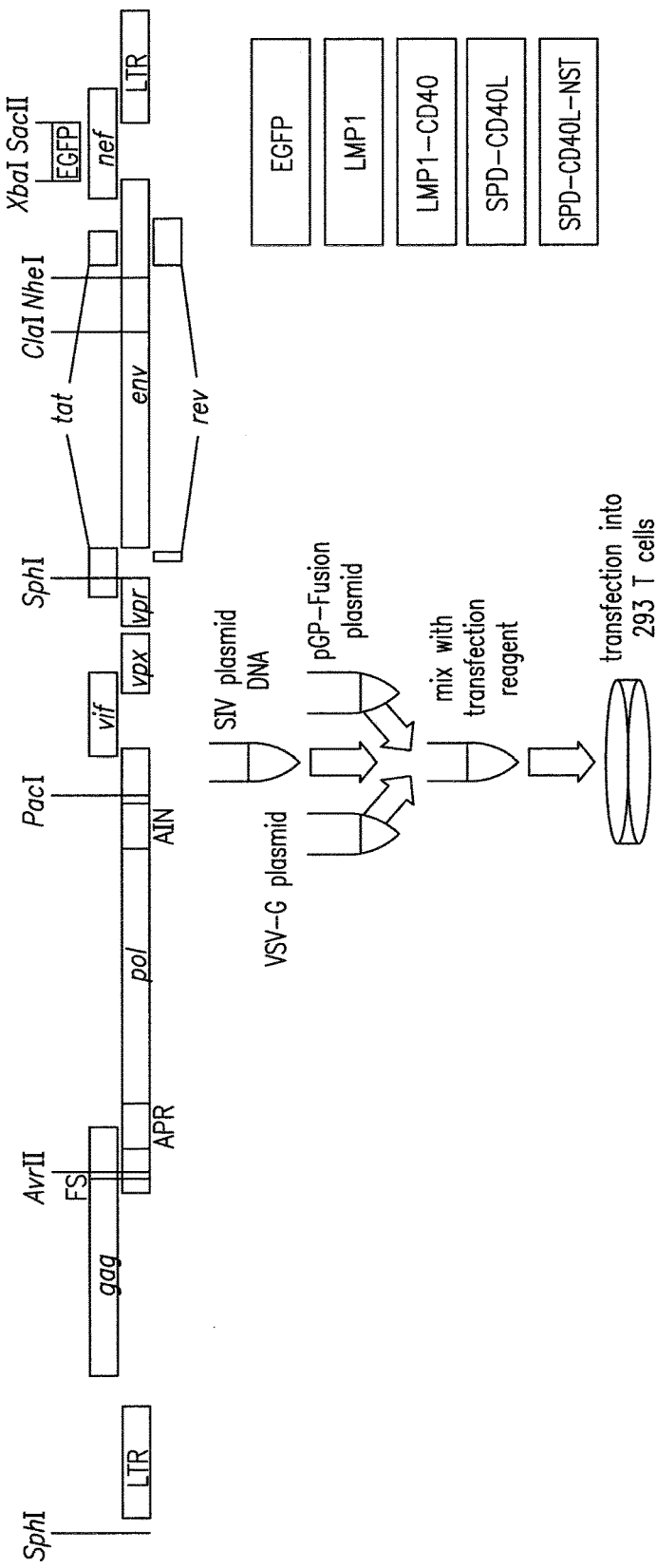

FIG. 8 shows that construction of a single-cycle SIV clone (scSIV) that expresses LMP1 or LMP1-CD40. The figure shows the design of a proviral clone of Simian Immunodeficiency Virus (SIV) in which inactivating mutations have been introduced into codons for the Protease (PR) and Integrase (IN) genes. The diagram shows how other plasmids (encoding VSV-G envelope and a Gag-Pol polyprotein) are used to prepare pseudotyped virus that in turn is used to introduce the construct into 293T cells. As a result of this process, the 293T release recombinant virus that can infect SIV-susceptible cells yet not replicate in them due to a lack of PR and IN. On the right are shown the cassettes that are introduced into the nef-spliced mRNA in place of Nef: EGFP; LMP1; LMP1-CD40; SP-D-GITRL; SP-D-CD40L; and SP-D-CD40L-NST.

Figure 9:
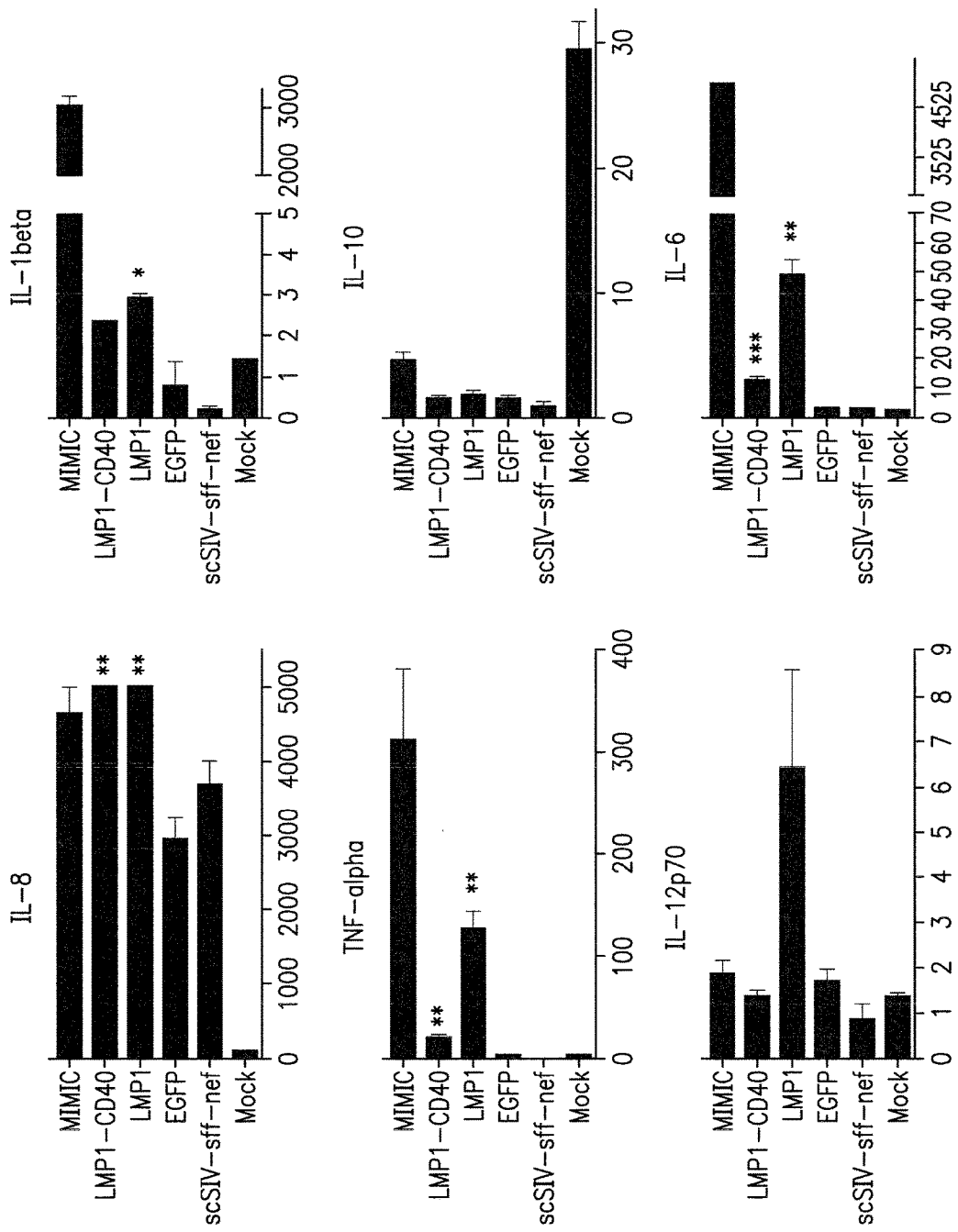

FIG. 9 shows stimulation of human dendritic cells by scSIV expressing LMP1 or LMP1-CD40. Human monocyte-derived dendritic cells (DCs) are infected with scSIV virus expressing LMP1, LMP1-CD40, or controls at 50 ng p27 Gag protein per million cells. As above, MIMIC™ is a standard cytokine cocktail used as a positive control. Supernatants are collected after 5 days and cytokines measured. As shown, the LMP1-expressing scSIV stimulates DCs to produce IL-8, IL-1β, TNFα, IL-12p70, and IL-6, but does not stimulate the production of IL-10, an immunosuppressive cytokine. LMP1-CD40-expressing scSIV stimulates DCs to produce IL-8, TNFα, and IL-6, but not TNFα, IL-12p70, or IL-10.

Figure 10:
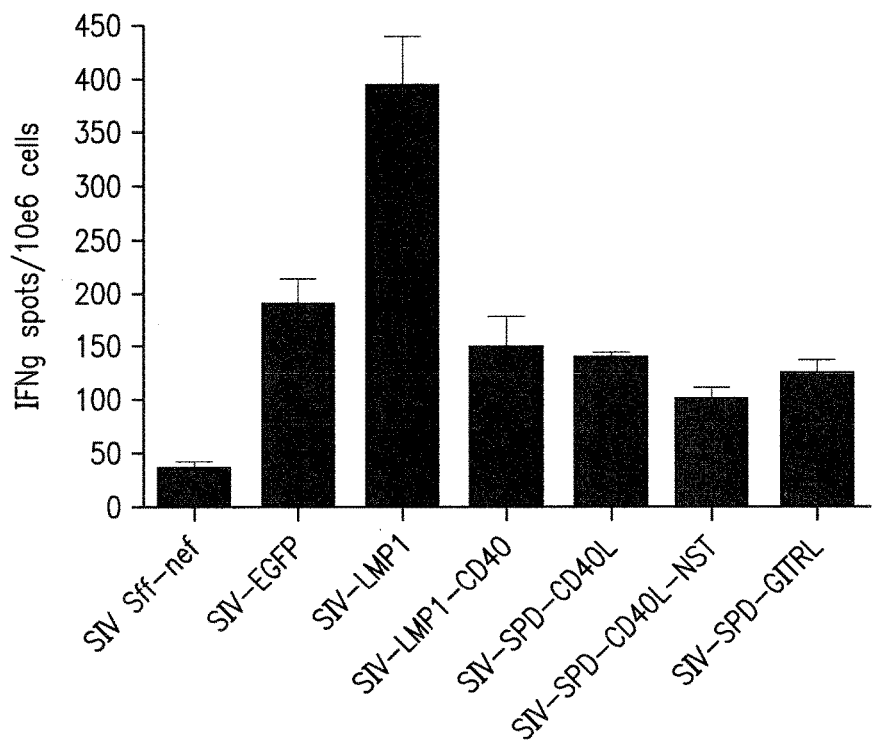

FIG. 10 shows self-adjuvanticity of a single-cycle SIV expressing the LMP1 multimerizing-intracellular signaling cassette. The present invention provides that single-cycle SIV (scSIV) can carry its own antigens into immune responses and a multimerizing-intracellular signaling cassette can act as an adjuvant for tins. Human monocyte-derived dendritic cells (DCs) are studied in vitro. The DCs are exposed to the scSIV viruses for 4 days, and then co-cultured with human T cells for another 12 days. After the co-culture period, the cells are transferred to the wells of an Enzyme Linked Immuno-Spot (ELISPOT) plate and stimulated with a pool of SIV Gag 15-mer peptides. This assay provides a rigorous evaluation of antigen-presenting function and T cell responses, given that the T cells are naïve for Gag antigen on day 0. As shown in the figure, scSIV-LMP1 induces a significant increase in Gag-specific interferon gamma responsive T cells (p<0.01 comparing scSIV-LMP1 to scSIV-EGFP). These data and similar results with HIV-LMP1 demonstrate that scSIV-LMP1 is immunostimulatory and effectively self-adjuvanting by the inclusion of the LMP1 multimerizing-intracytoplasmic signaling cassette. This surprising result is the prototype for a range of viruses, vectors, and tumor cells where the inclusion of a multimerizing-intracytoplasmic signaling cassette is predicted to induce a strong immune response to the antigens that are co-extensive in space and time.

Figure 11:
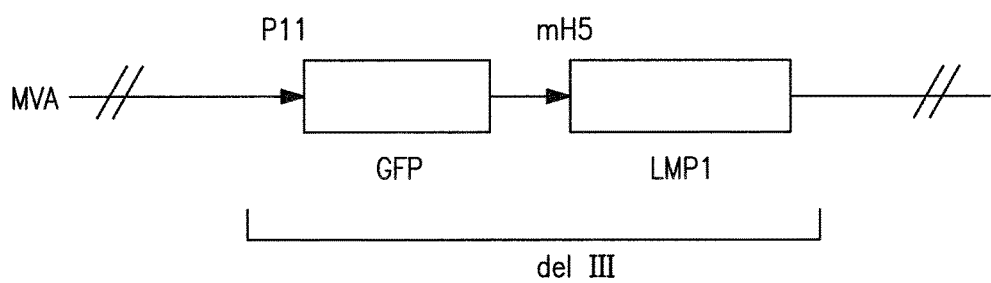

FIG. 11 shows introducing LMP1 into Modified Vaccinia Ankara by homologous recombination. The schematic shows a transfer vector modified from pLW-44 in which the Vaccinia mH5 promoter drives the expression of LMP1.

FIG. 12 shows that LMP1 or LMP1-CD40 mRNAs alone are sufficient to activate DCs. LMP1, LMP1-CD40, or control GFP mRNAs are introduced into DCs by electroporation. Other controls are DC cultures electroporated without adding mRNA (mock) and non-transfected, untreated DCs. Following 48 hours of culture, cell surface markers are analyzed by flow cytometry and cytokine production is analyzed by cytometric bead analysis (CBA). (*, P 0.05; , P 0.01; *, P 0.001 using an unpaired t-test compared to the GFP mRNA control).

Figure 12A:
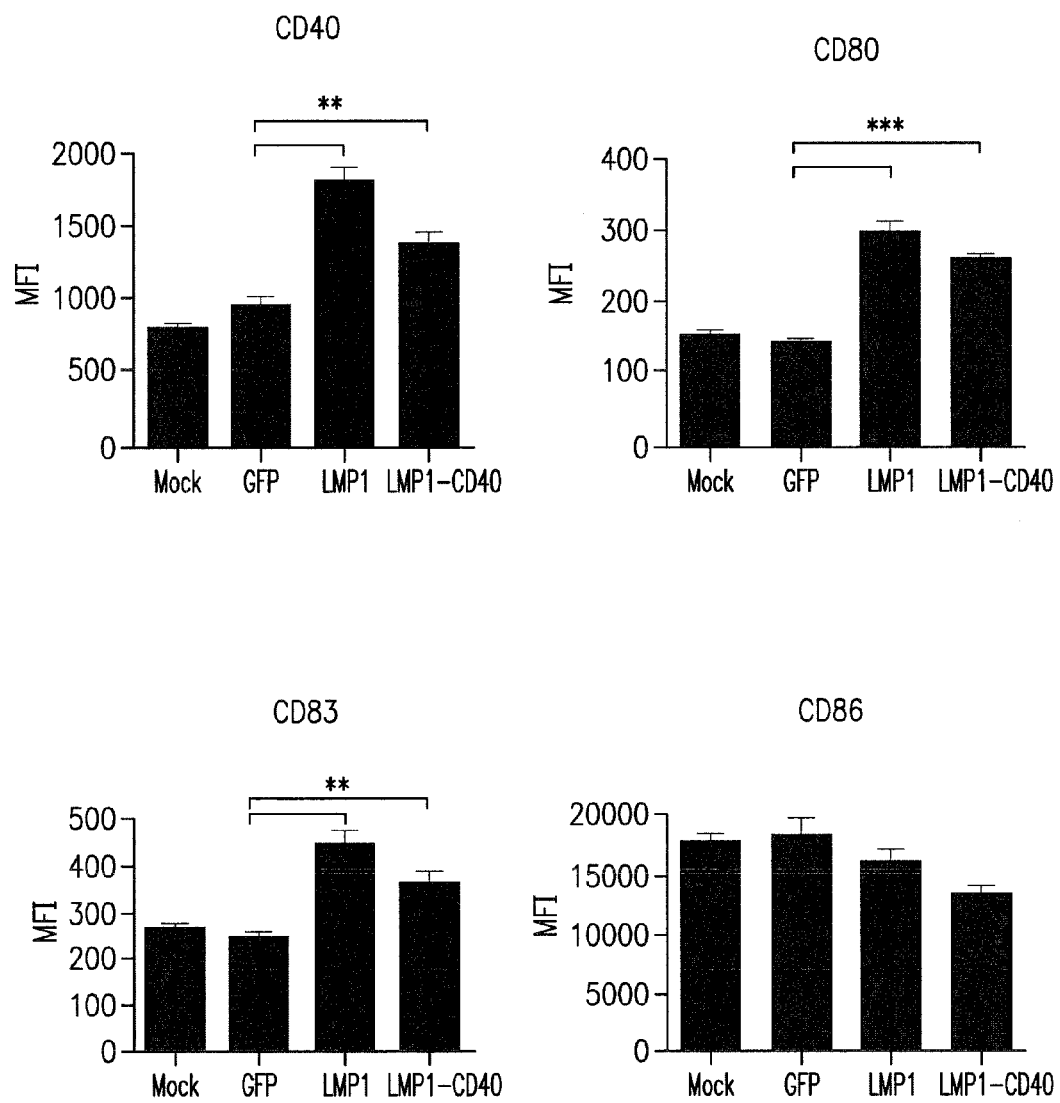

FIG. 12A shows that LMP1 or LMP1-CD40 mRNA transduction upregulates CD40 and CD83 maturation markers and CD80 and CD86 co-stimulatory molecules as measured by mean fluorescence intensity (MFI). Bars show the means and SEM of triplicate wells.

Figure 12B:
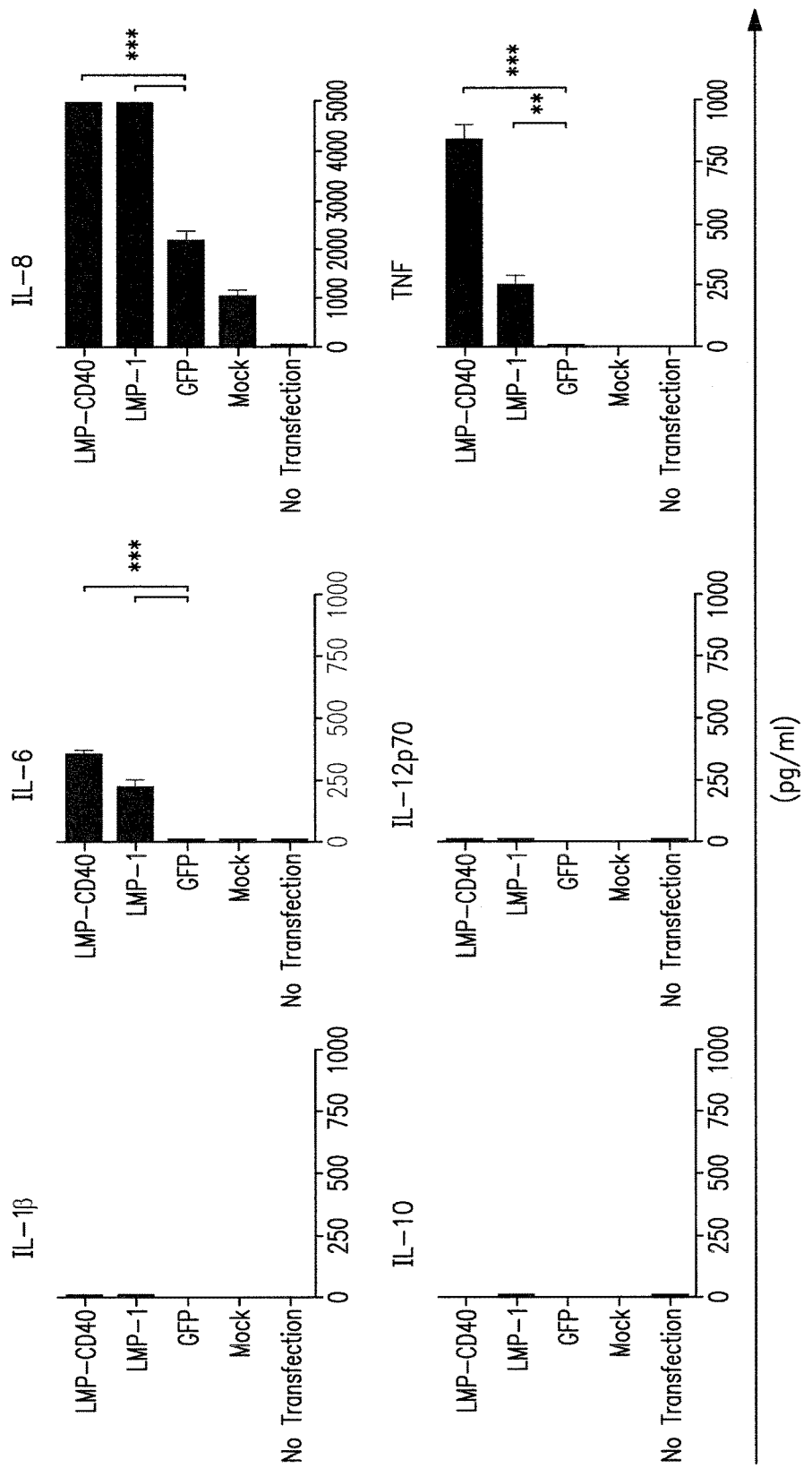

FIG. 12B shows that LMP1 or LMP1-CD40 mRNA transduction upregulates the secretion of cytokines IL-6, IL-8, and TNFα, but is unable to upregulate secretion of IL-1β, IL-10, or IL-12p70. Bars show the means and SEM of triplicate wells.

Figure 13A:
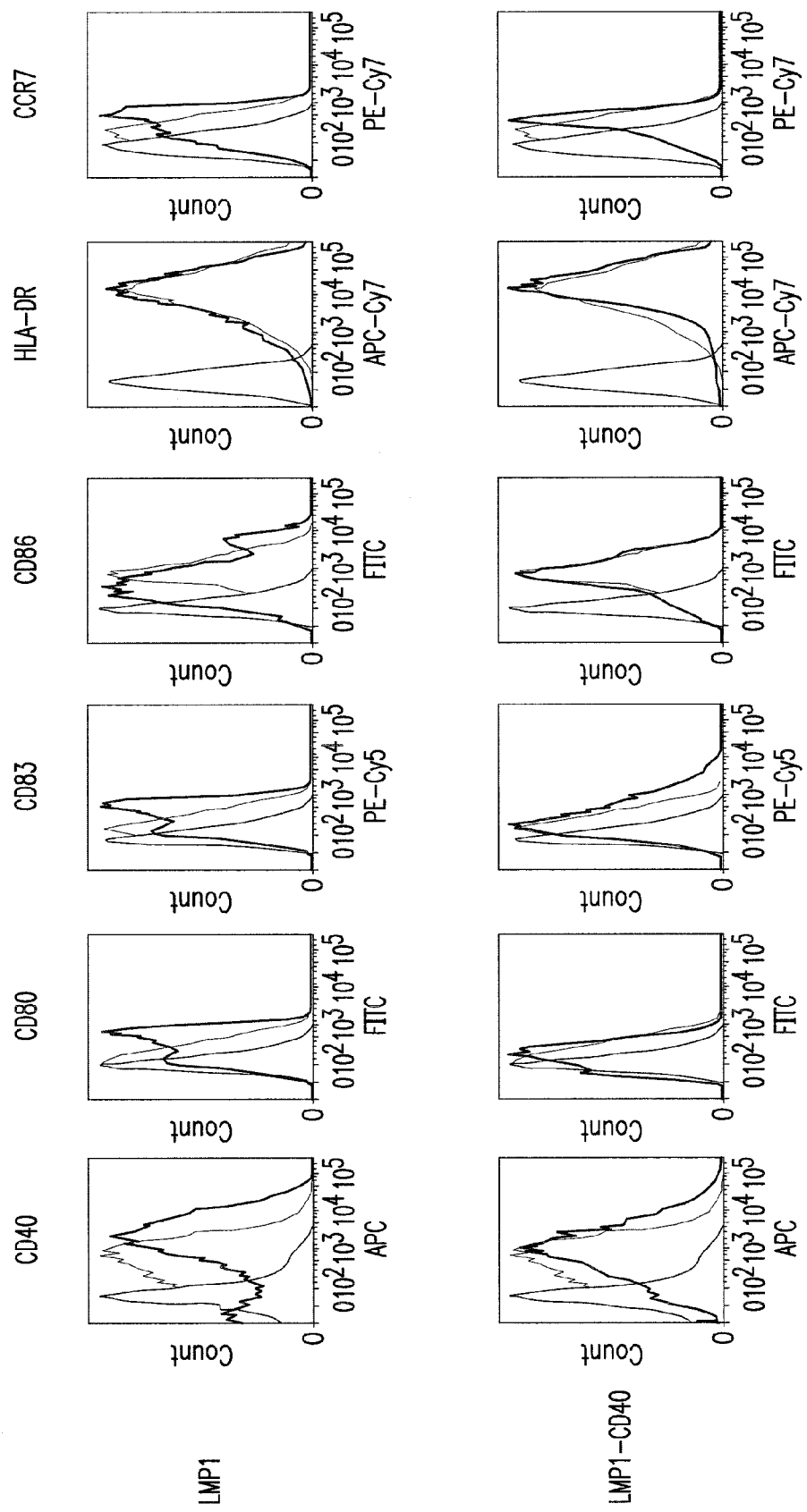

FIG. 13 shows that HIV-LMP1 or HIV-LMP1-CD40 viral transduction activates DCs and macrophages to express cell maturation- and activation-associated surface molecules. FIG. 13A shows the expression of surface markers on DCs 4 days after viral transduction. Flow cytometry events are first gated for DCs using forward scatter and side scatter. Isotype antibody control staining (grey filled histogram), HIV-GFP (thin line), or HIV-LMP1 and HIV-LMP1-CD40 (thick lines) are shown. Viral transduction with HIV-LMP1 results in dendritic cell activation and maturation as measured by increased levels of CD40, CD80, CD86, CD83, and CCR7 expression. By comparison, viral transduction with HIV-LMP1-CD40 produces a modest increase in CD40 and CD83 expression and a minimal increase in CD80 and CCR7 expression when compared to HIV-GFP transduced cells.

Figure 13B:
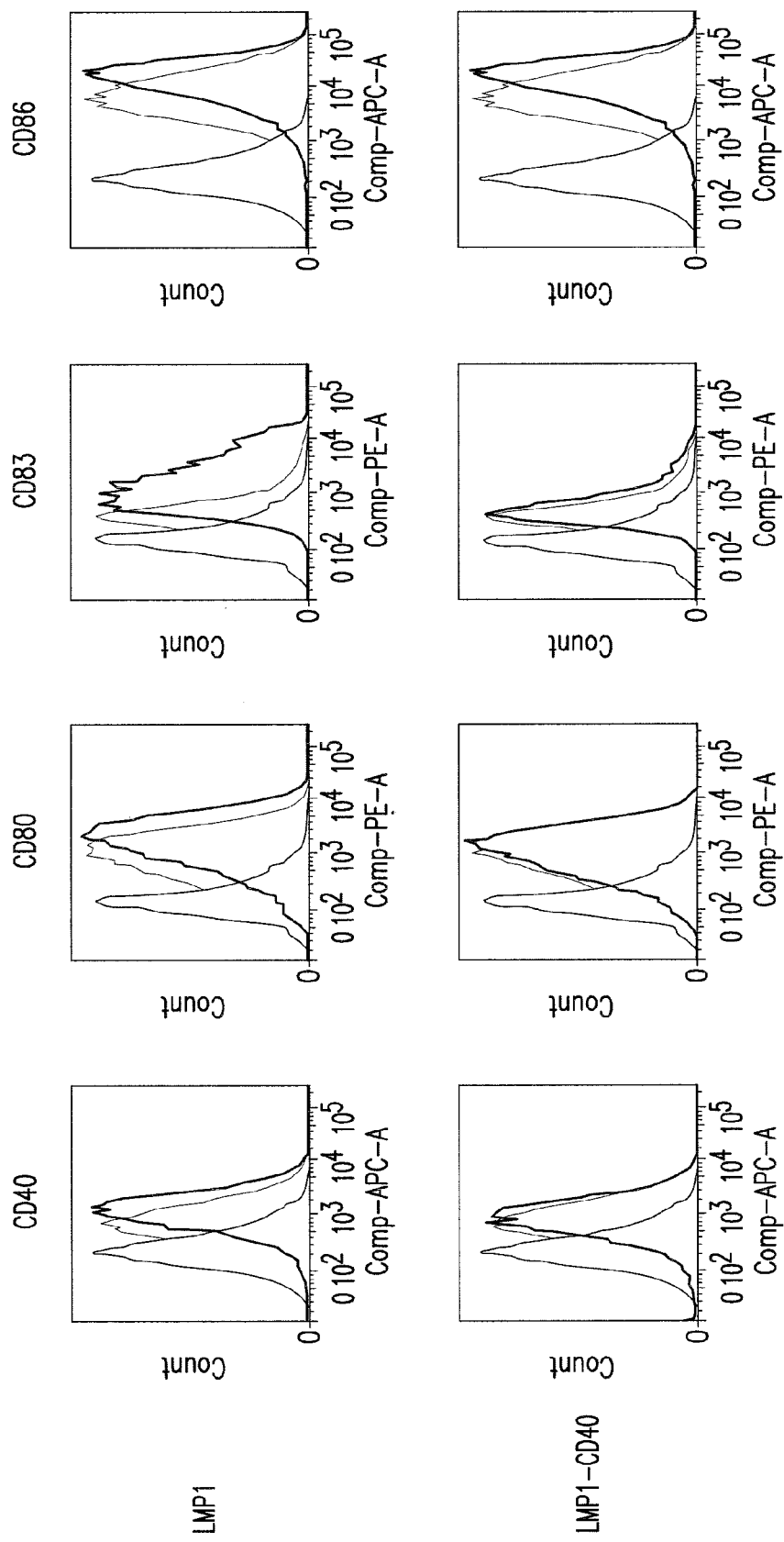

FIG. 13B shows the expression of surface markers on macrophages 4 days after viral transduction. Flow cytometry events are first gated for DCs using forward scatter and side scatter. Isotype antibody control staining (grey filled histogram), HIV-GFP (thin line), or HIV-LMP1 and HIV-LMP1-CD40 (thick lines) are shown. HIV-LMP1 transduction activated macrophages to express higher levels of CD40 and CD83 maturation markers and CD80 and CD86 co-stimulatory molecules. By comparison, viral transduction by HIV-LMP1-CD40 is less active and induced increased levels of CD83 and CD86, but not CD40 or CD80. These results are representative of three experiments on three different donors.

Figure 14A:
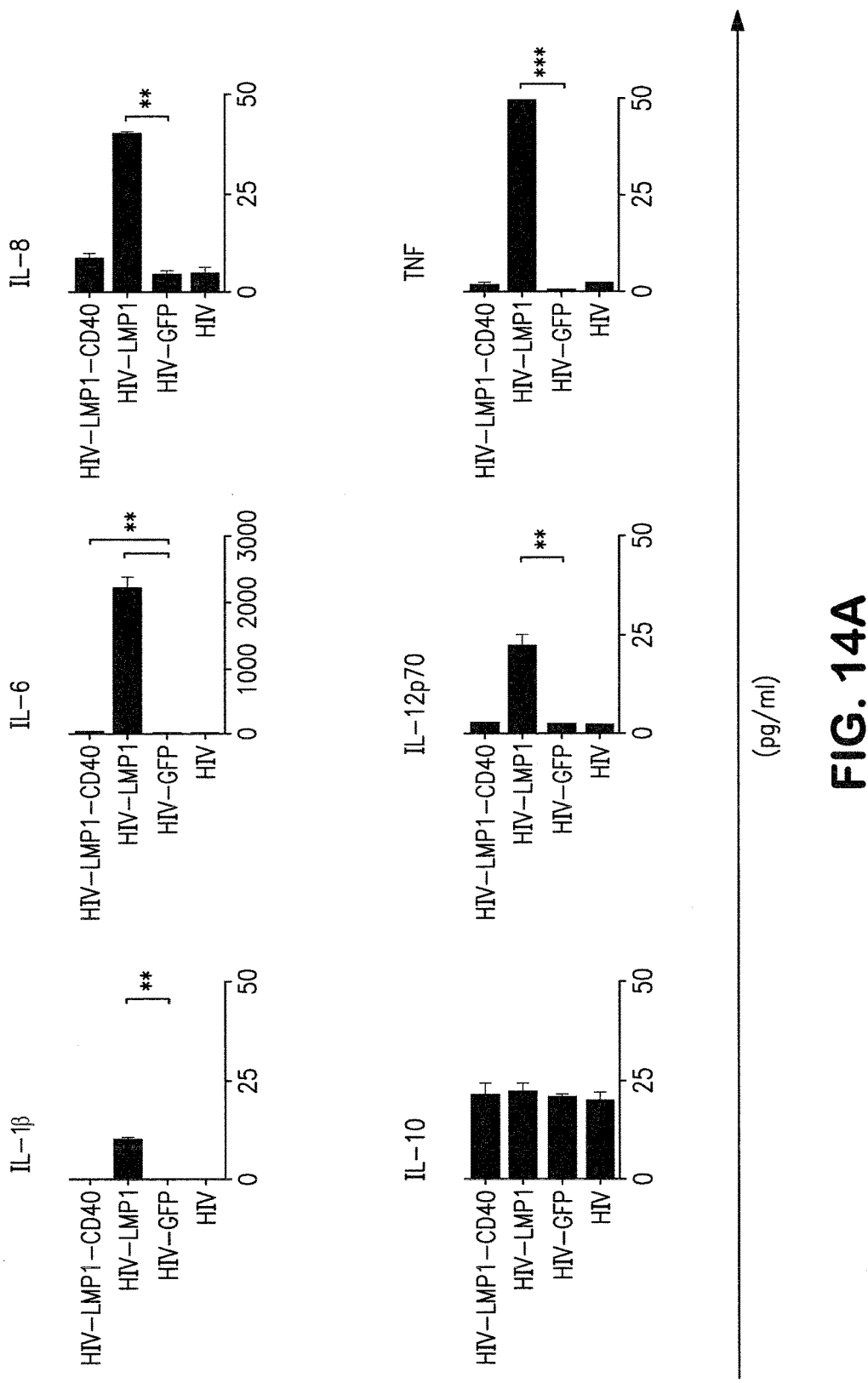

FIG. 14 shows that HIV-LMP1 or HIV-LMP1-CD40 viral transduction activates DCs and macrophages to secrete immunostimulatory cytokines. FIG. 14A shows the effects of viruses on cytokine secretion by DCs. DCs are exposed to viruses at an MOI of 0.1, cultured for 7 d, and supernatants are collected for analysis by cytokine bead array (CBA) assay. As shown, HIV-LMP1 induces significant increases in IL-6 and IL-8 secretion, modest increases in IL-1β, IL-12p70 and TNFα, secretion, and no induction of IL-10 secretion. By comparison, HIV-LMP1-CD40 induces significant increase in IL-6 secretion, reflecting fine differences in the cell signaling induced by the LMP1 vs. LMP-CD40 adjuvant cassettes in DCs. The bars show the means from three independent experiments with DCs from three different donors (*, P 0.05;  P 0.01; *, P 0.001 using an unpaired t-test compare to the HIV-GFP control virus).

Figure 14B:
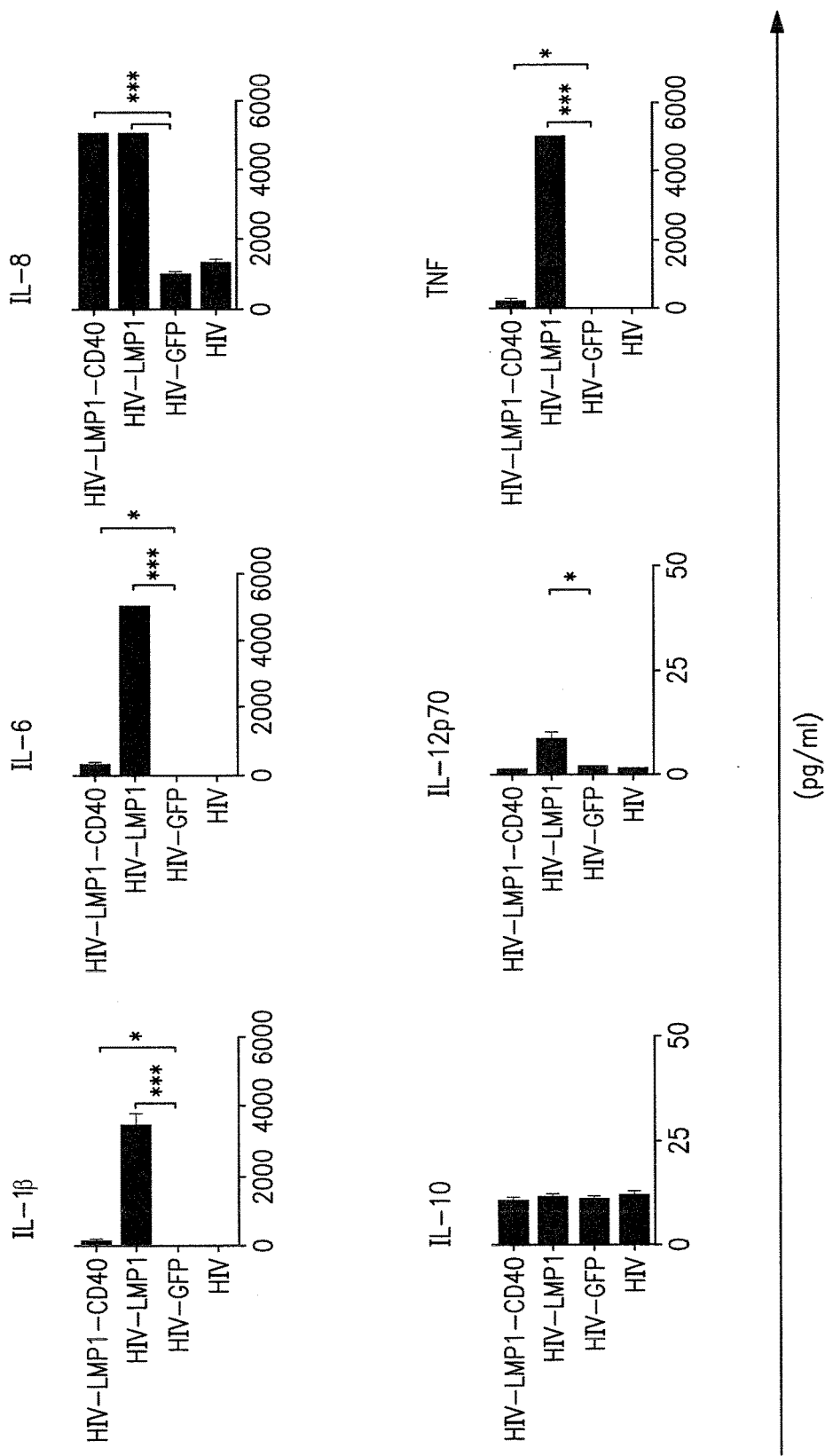

FIG. 14B shows the effects of viruses on cytokine secretion by macrophages. These cells are exposed to viruses at an MOI of 0.1 and supernatants are collected at various time points for CBA cytokine analysis. For macrophages, HIV-LMP1 induces a significant increase in secretion IL-1β, IL-6, IL-8, IL-12p70 and TNFα, but little or no increase in IL-10 production. By comparison, HIV-LMP1-CD40 induces a significant increase in IL-1β, IL-6, IL-8 and TNFα secretion. The bars show the means from three independent experiments with DCs from three different donors.

Figure 15A:
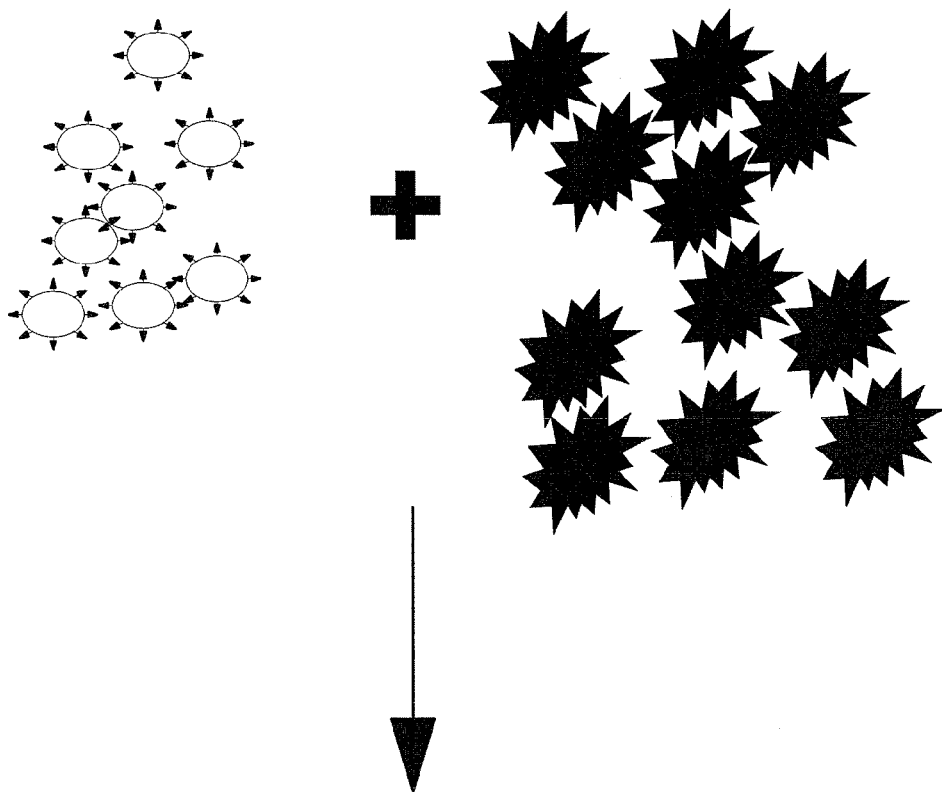
Figure 15A:
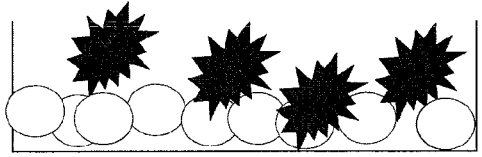

FIG. 15 shows that HIV-LMP1 enhances the ability of DCs to present HIV Gag antigen to T cells in an in vitro immunization assay. FIG. 15A shows a schematic of the experimental protocol. DCs from an HIV seronegative donor are exposed to different HIV viruses for 6 days, washed, and then incubated with autologous T cells for 12-days in the presence of nevirapine and IL-2 (5 U/ml) starting on day 3. Cultures are then restimulated with a consensus clade B 15-mer Gag peptide pool and IFN-γ ELISPOT analysis is performed 24 hours later.

Figure 15B:
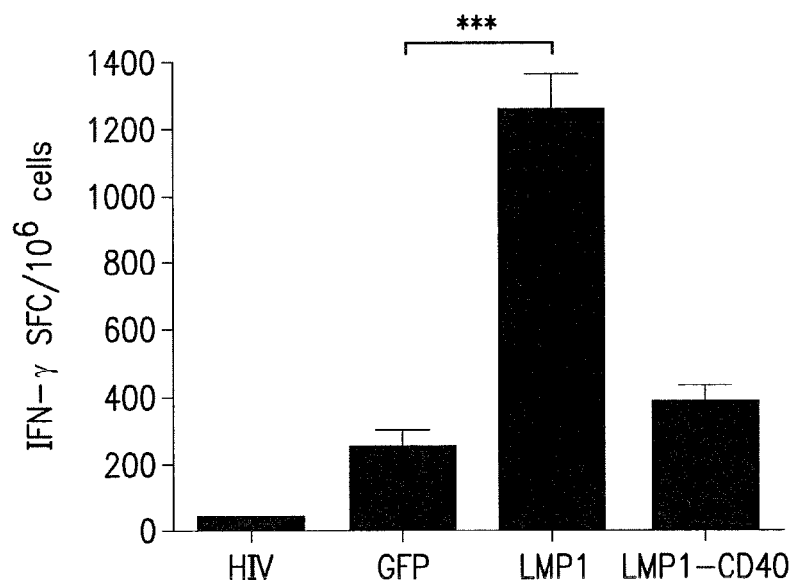

FIG. 15B shows that DCs exposed to native HIV infection do not stimulate anti-HIV HIV T cell responses. This is consistent with the known inability of HIV to stimulate strong T cell responses when compared to more effective viral vaccines for other viruses. However, HIV-LMP1 strongly enhances anti-Gag T cell responses (***, P<0.001 by unpaired t-test comparing HIV-LMP1 with the HIV-GFP control virus). This shows the ability of the LMP1 adjuvant gene cassette to convert a poorly immunogenic virus into a strongly immunogenic one. By comparison, HIV-LMP1-CD40 is much less active in this assay, consistent with the overall weaker effect of HIV-LMP1-CD40 in DCs compared to HIV-LMP1 virus. These results are representative of three experiments on three different donors.

Figure 16:
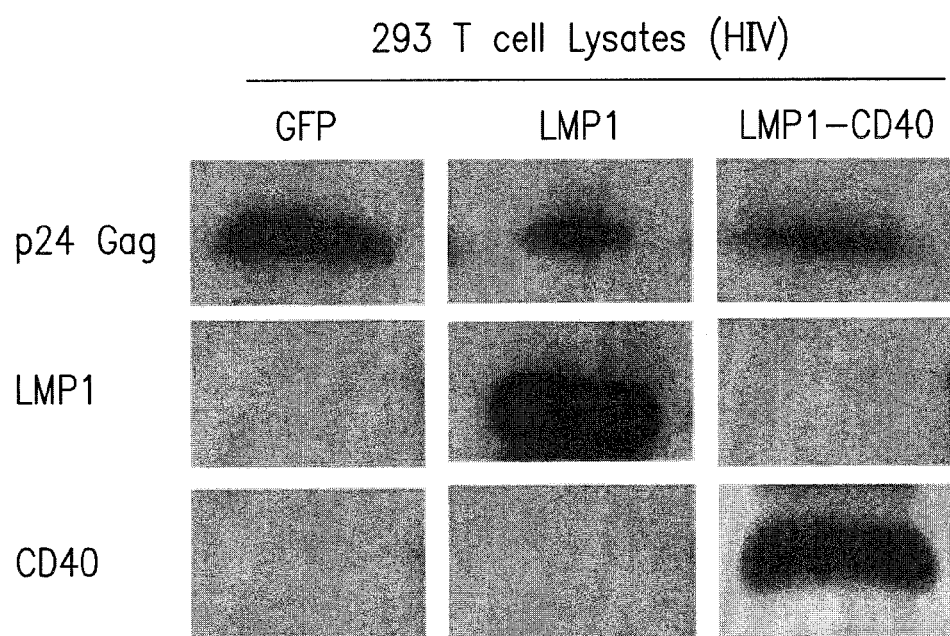

FIG. 16 shows that and LMP1-CD40 proteins are expressed by HIV-LMP1 and HIV-LMP1-CD40 constructs. To show that the insertion of LMP1 and LMP CD40 coding sequences into HIV leads to translated proteins, proviral DNA plasmids for HIV-LMP1 or HIV-LMP1-CD40 are transfected into 293 cells along with the HIV-GFP control construct. Cells are lysed 24 hours later, processed by SDS PAGE followed by transfer onto nitrocellulose membranes and staining with antibodies for Gag (upper panels), LMP1 N-terminus (middle panels), or the C-terminal intracytoplasmic domain of CD40 (lower panels). As shown, cells transfected with all three viral constructs express p24 Gag. The LMP1 protein is detected in cells transfected with the LMP1 constructs. The intracytoplasmic signaling domain of CD40 can be observed in LMP1-CD40-transfected cells.

Figure 17:
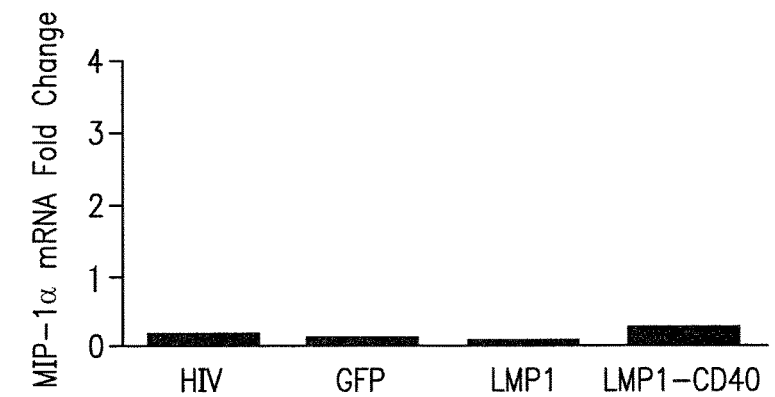
Figure 17:
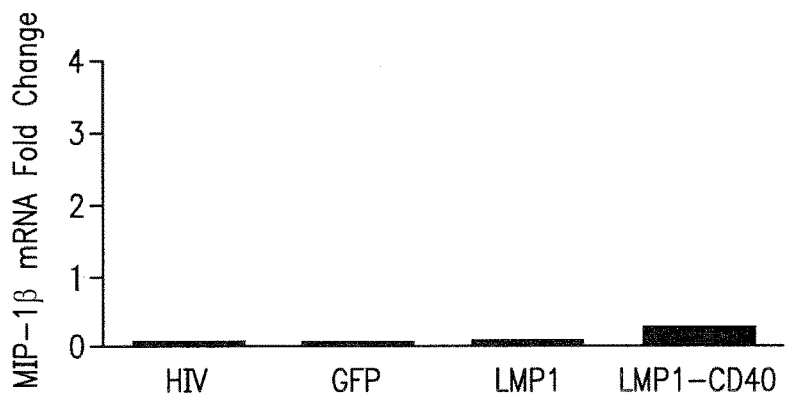
Figure 17:
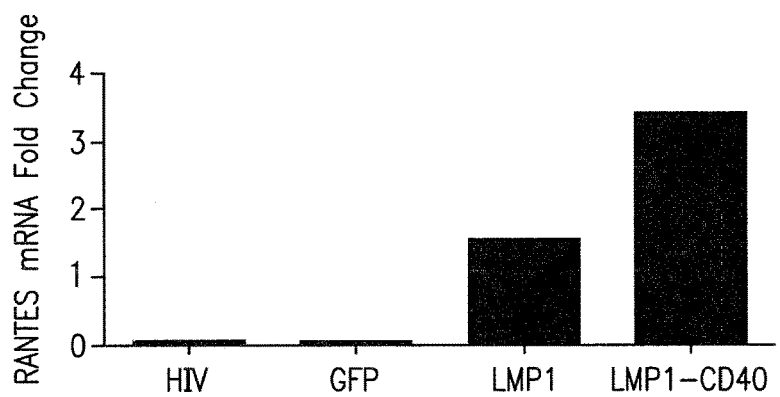

FIG. 17 shows that HIV-LMP1 or HIV-LMP1-CD40 induces chemokine production in macrophages. Macrophages are infected for 7 days and then analyzed by RT-PCR to measure steady-state levels of CCL3 (MIP-1α), CCL4 (MIP-1β), and CCL5 (RANTES). HIV infection is known to induce β (CC) chemokines under certain conditions, but HIV-LMP1-CD40 infection induced increased levels of these chemokines. By comparison, HIV-LMP1 infection is less immunostimulatory for macrophages chemokine production.

HIV-LMP1 and HIV-LMP1-CD40 infection induces activation-associated morphological changes in DCs and macrophages. DCs and macrophages are infected with HIV wild-type, HIV-EGFP, HIV-LMP1 or HIV-LMP1-CD40 at an MOI of 0.1. Four days later, the cells are photographed using an inverted phase contrast microscope. DCs infected by HIV-LMP1 or HIV-LMP1-CD40 develop elongated dendrite-like processes. Macrophages infected by these viruses, but not the control HIV or HIV-GFP viruses, undergo extensive clumping. The degree of clumping is less with HIV-LMP1-CD40 than with HIV-LMP1, suggesting that HIV-LMP1-CD40 is less active than HIV-LMP1 in macrophages.

Figure 18:
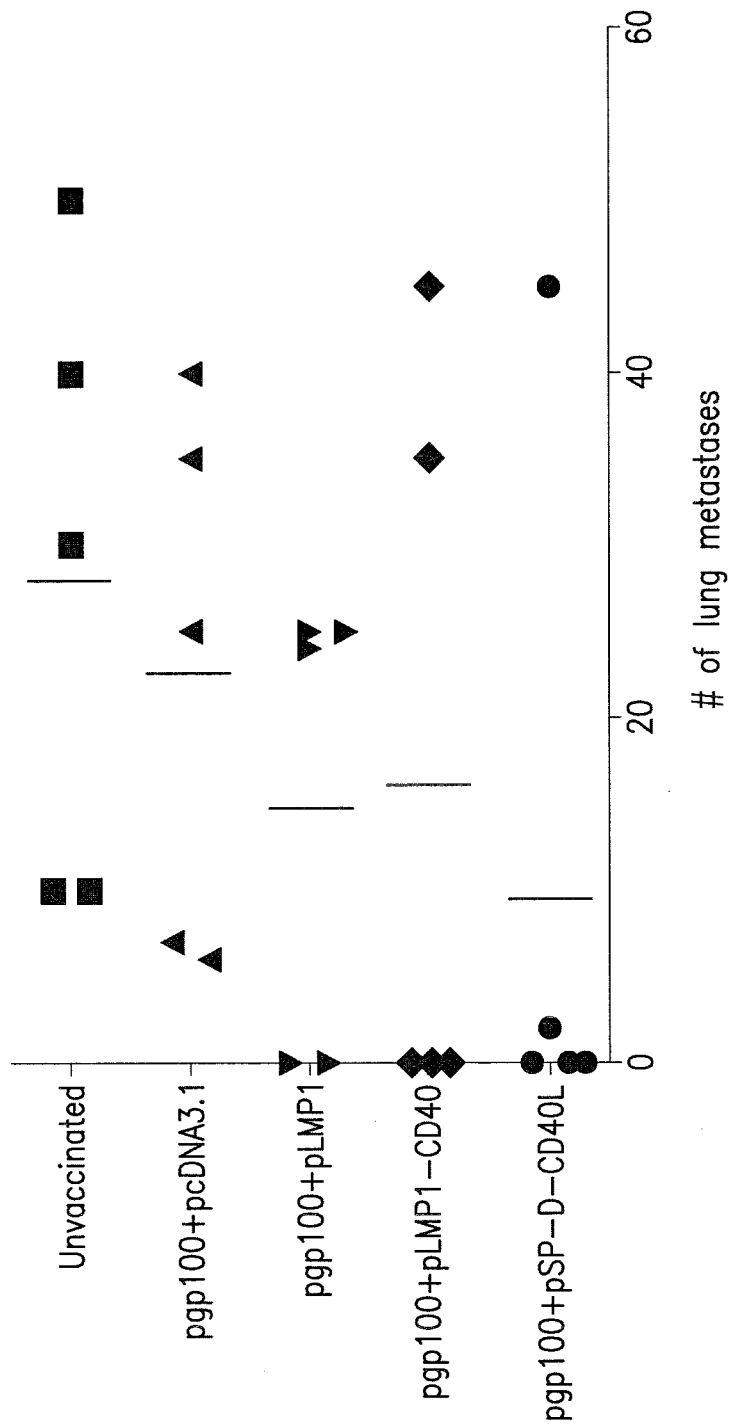

FIG. 18 shows that plasmids encoding LMP1 (pLMP1) or LMP1-CD40 (pLMP1-CD40) can be used as DNA vaccine adjuvants. As DNA vaccine adjuvants, pLMP1 and pLMP1-CD40 can help to protect mice from melanoma metastases. As shown in FIG. 18, pSP-D-CD40L is also very effective. These data show that stimulating cells from within using a clustered CD40 receptor LMP1 or LMP1-CD40) is nearly as effective as stimulating cells from without using a multimeric soluble CD40L construct.

In another aspect, C57BL/6 mice are either untreated (naïve) or DNA vaccinated intramuscularly with 50 µg plasmid DNA encoding melanoma antigen pgp100 combined with 50 µg either control empty vector plasmid (pcDNA3.1) or pLMP1, pLMP1-CD40, or pSP-D-CD40L dissolved in a total injected volume of 100 µL phosphate-buffered saline. Vaccinations are delivered every two weeks for three doses. One week after the last vaccination, the mice are injected intravenously with $1 \times 10^5$ B16F10 melanoma cells. Twenty-one (21) days later, the mice are euthanized; the lungs were removed, and examined for lung metastases. The results indicate that the pgp100+pcDNA3.1 control has no protection, where pgp100+pLMP1 and pgp100+pLMP1-CD40 completely protected 2 of 5 and 3 of 5 mice, respectively. This demonstrates that plasmids encoding LMP1 (pLMP1) or LMP1-CD40 (pLMP1-CD40) can serve as immune adjuvants for DNA vaccines, in this case a tumor DNA vaccine.

Figure 19:
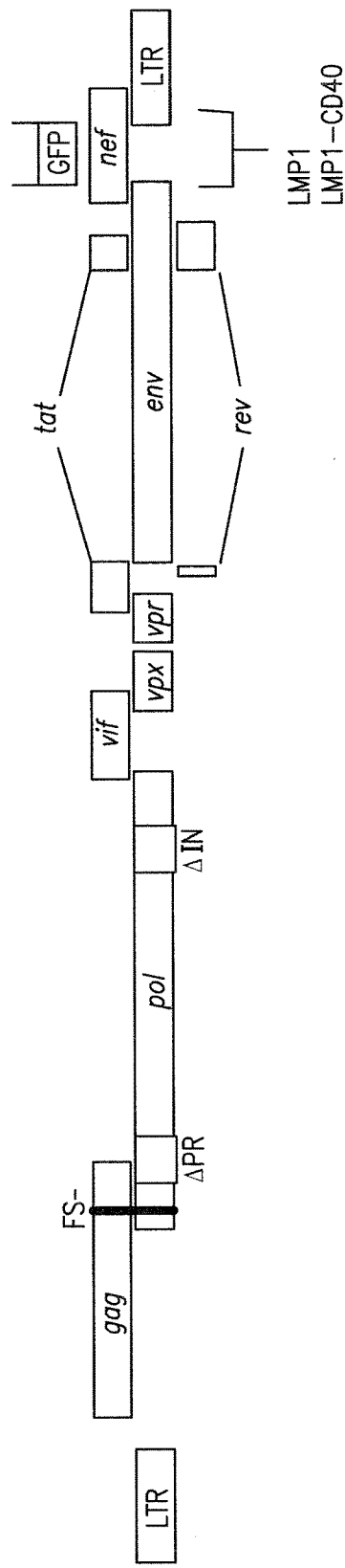

FIG. 19 shows an exemplary single cycle SIV (scSIV) viral genome of the invention. The parent vector, expressing GFP from the Nef promoter, is cloned by overlap PCR and inserted into the SIVmac239 FS-ΔPR-ΔINEGFP vector using unique XbaI and SacII sites. To create immunostimulatory forms of scSIV, LMP1 or LMP1-CD40 is inserted in place of the GFP gene as shown.

Figure 20:
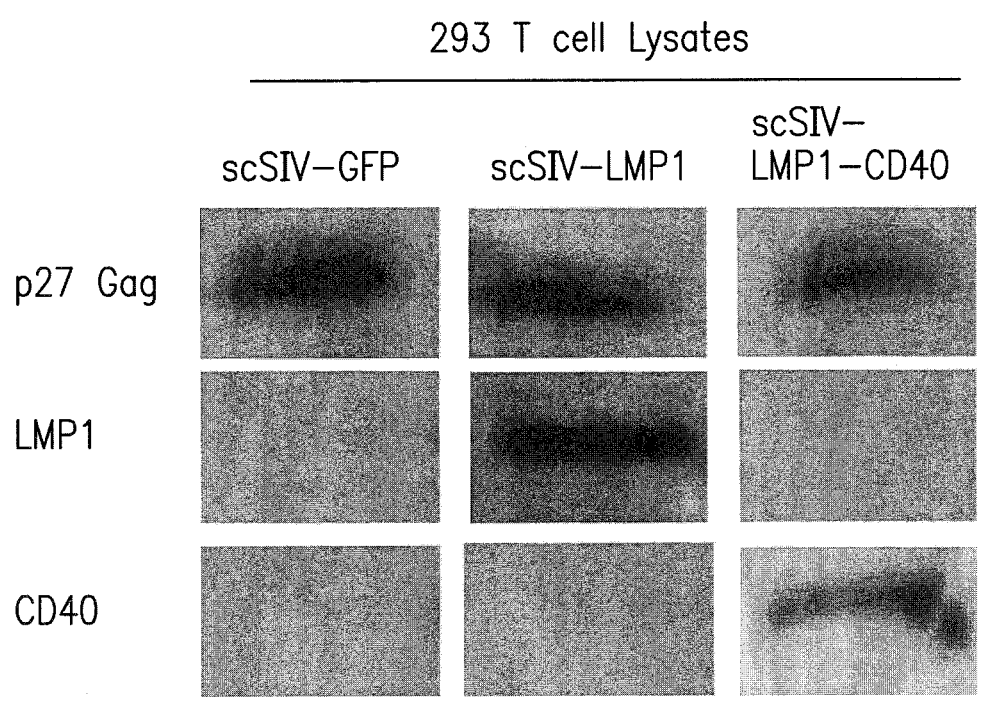

FIG. 20 shows an exemplary Western blot of 293T cell lysates transfected with SIV expressing LMP1 or LMP1-CD40, where SIV virus expressing LMP1 or LMP1-CD40 induces morphological and other changes in DCs and macrophages. Virus expressing GFP serves as a negative control. Blots are stained with anti-Gag (upper panels), anti-LMP1 intracellular domain (middle panels), or anti-CD40 intracellular domain (lower panels). Gag p27 is present in all lysates. LMP1 and CD40 intracellular domains are present only in cells transfected with LMP1 or LMP1-CD40 viral constructs respectively. Only LMP1 or LMP1-CD40 expressing viruses induce elongation of human DCs or macrophages, suggesting the activation and maturation of cells in the culture.

Figure 21A:
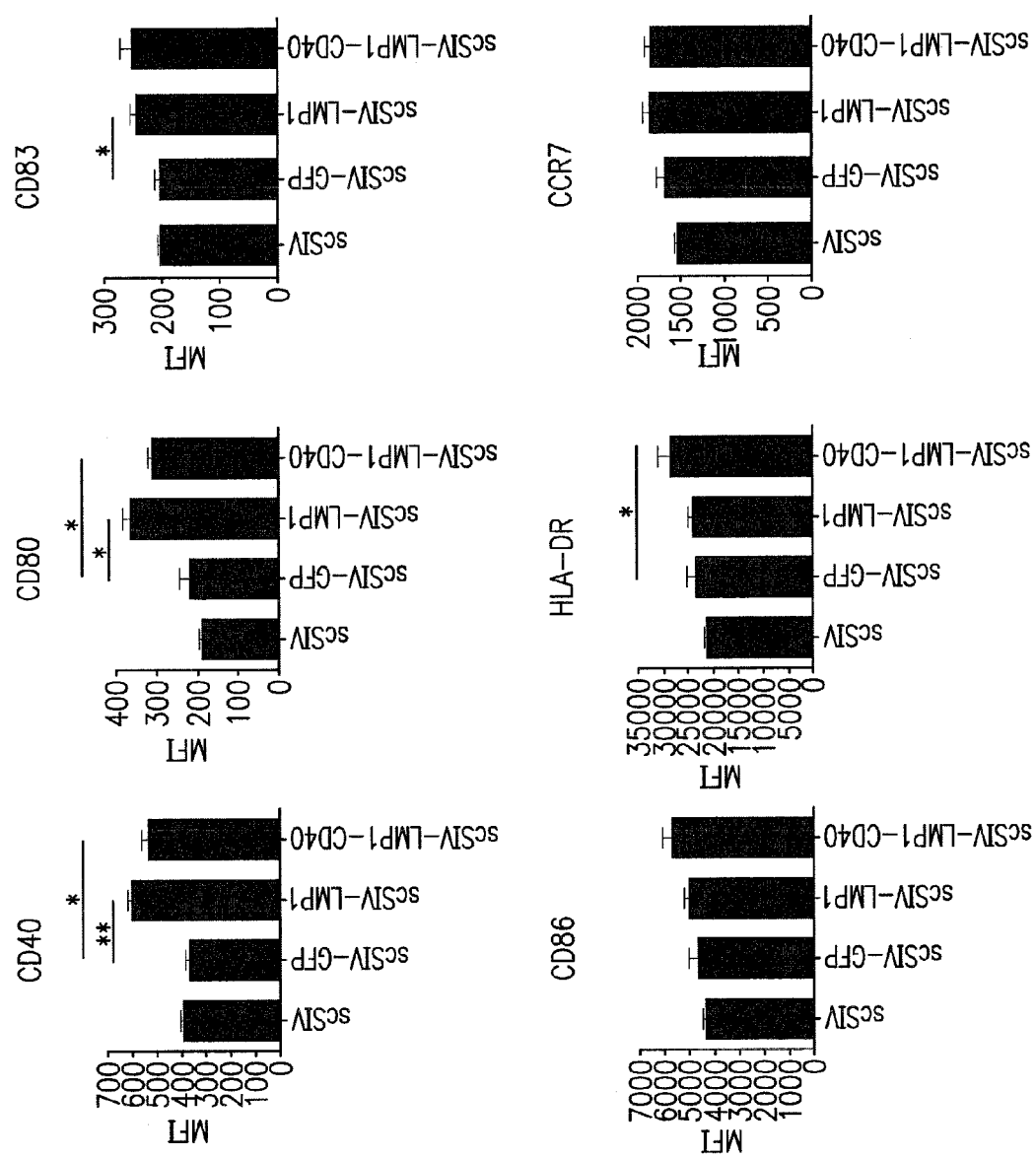
Figure 21B:
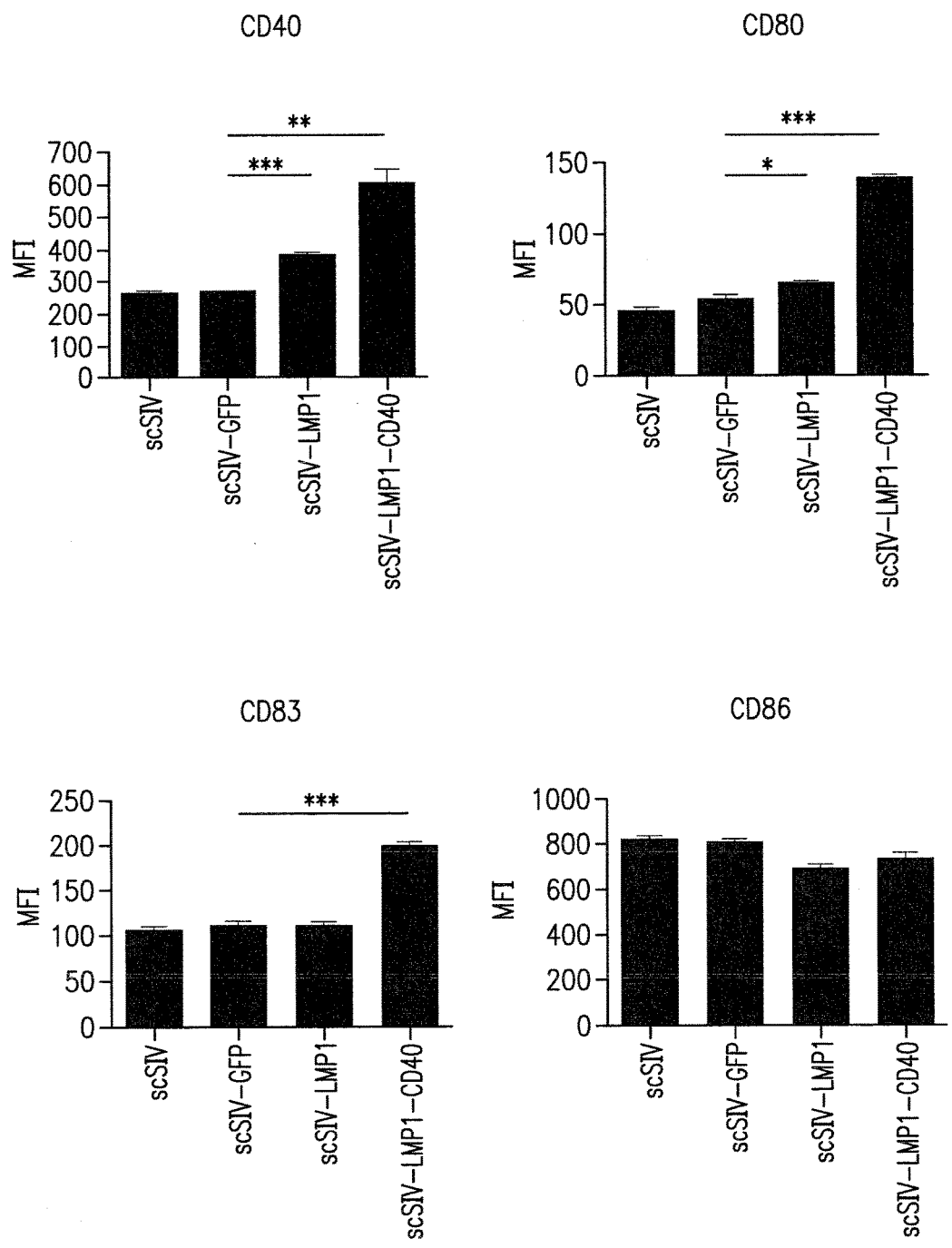

FIG. 21 shows that viral transduction of human DCs or macrophages with scSIV expressing LMP1 or LMP1-CD40 results in increased levels of maturation and activation markers. The expression levels of surface markers from three independent experiments are presented as mean fluorescence intensity (MFI). FIG. 21A shows that the expression of surface markers on SIV infected DCs is examined by flow cytometry 4 days after transduction. Transduction with scSIV-LMP1 results in dendritic cell activation and maturation as measured by significantly increased levels of CD40, CD80 and CD83 expression, while scSIV-LMP1-CD40 results in significant increased levels of CD40, CD80 and HLA-DR expression when compared to scSIV-GFP-transduced cells. FIG. 21B shows that the expression level of surface markers on scSIV virus-transduced macrophages is examined 4 days after transduction by flow cytometry from a representative donor. Transduction with scSIV-LMP1 results in increased levels of CD40 and CD80 expression, while scSIV-LMP1-CD40 results in increased levels of CD40, CD80 and CD83 expression compared to scSIV-GFP-transduced macrophages. Data are analyzed with the unpaired t test: *, $p<0.05$; , $p<0.01$; *, $p<0.001$ compared with the scSIV-GFP infected group.

Figure 22:
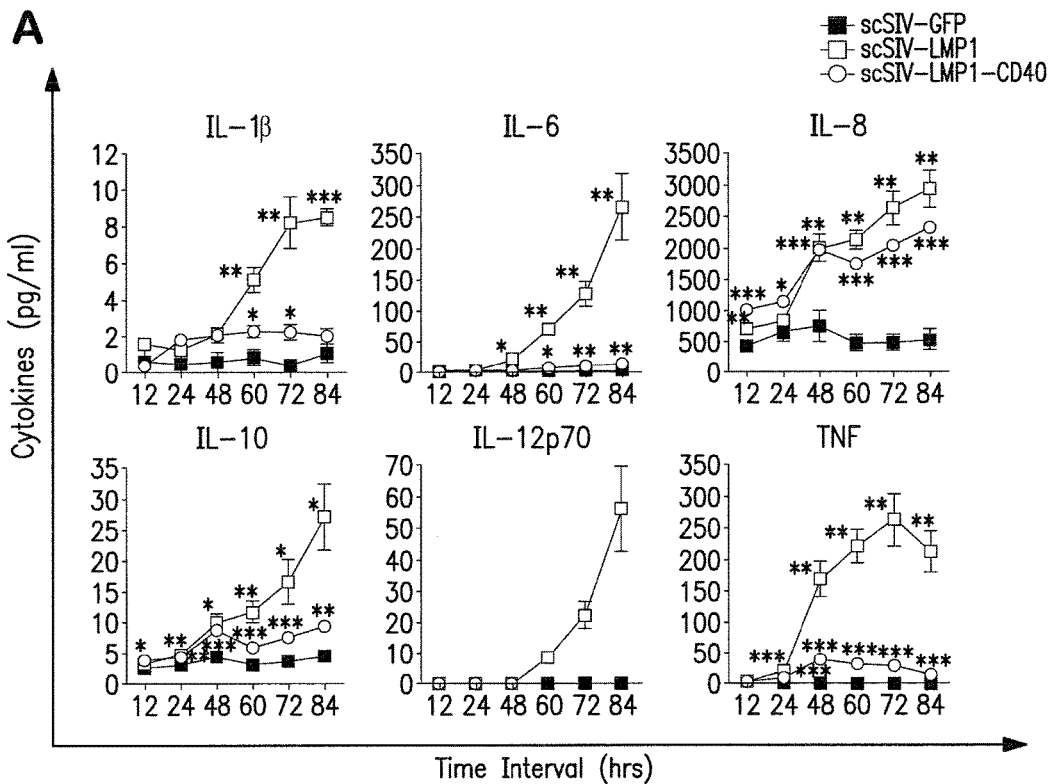
Figure 22:
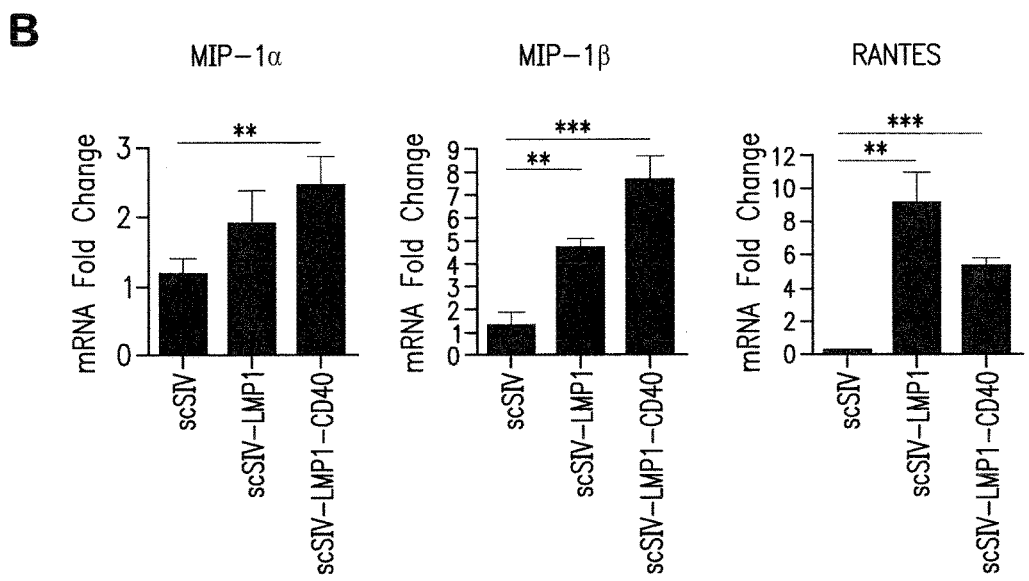

FIG. 22 shows that scSIV expressing LMP1 or LMP1-CD40 induces increased secretion of inflammatory cytokines and β-chemokines, and correspondingly increases the level of their steady-state mRNAs. Human inflammatory cytokine quantitation is performed by cytometric bead array (CBA). Cytokine concentrations are presented. Data are analyzed with the unpaired t test: *, $p<0.05$; , $p<0.01$; *, $p<0.001$ compared with the scSIV-GFP infected group. MIP-1α, MIP-1β, and RANTES mRNA expressions are analyzed by real-time RT-PCR assay. FIG. 22A shows that DCs are infected with the various SIV viruses at MOI of 0.05 and supernatants are collected at various time intervals. Virus expressing LMP1 results in a significant increase in IL-1β, IL-6, IL-8, IL-10, IL-12p70 and TNFα, while LMP1-CD40 results in an increase in IL-1β, IL-6, IL-8, IL-10 and TNFα at various time points post infection. No measurable amounts of IL-12p70 are detected in GFP and LMP1-CD40 groups. FIG. 22B shows that macrophages are infected with different scSIV viruses for 4 days. Total cellular RNA is isolated, reverse transcribed to cDNA and MIP-1α, MIP-1β, and RANTES mRNA expressions are analyzed by real-time PCR assay. Virus expressing LMP1 results in significant increase in MIP-1β and RANTES mRNA expression, whereas LMP1-CD40 results in significant increase in MIP-1α, MIP-1β and RANTES mRNA expression. Expression of GAPDH is used for normalization of samples.

Figure 23B:
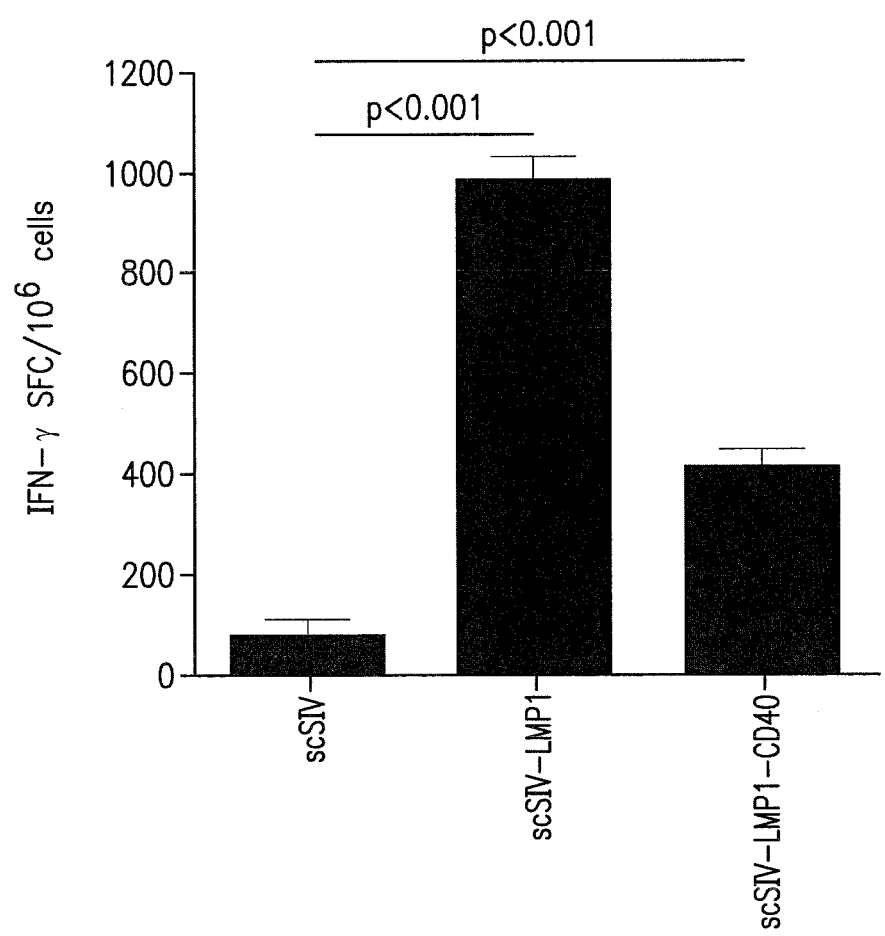

FIG. 23 shows that LMP1 induces enhanced cell responses in a Gag peptide-specific IFN-γ ELISPOT assay. FIG. 23A shows a schematic illustration of an experimental protocol of the invention. DCs from an HIV seronegative donor are transduced with scSIV viruses for 4 days, washed, and then incubated with autologous T cells for 12-days in the presence of nevirapine and IL-2 (5 U/ml) starting on day 3 of the coculture. After 12 days, cultures are restimulated with a consensus SIVmac239 15-mer Gag peptide pool and IFN-γ ELISPOT analysis is performed 24 hours later. FIG. 23B shows that DCs infected with parent scSIV are unable to stimulate anti-SIV T cell responses, while the nef-deleted virus scSIV-GFP induced a modest T cell response. DC infected with scSIV-LMP1 and LMP1-CD40 can significantly enhance anti-Gag T cell responses ($p<0.001$). Results are representative of three independent experiments using three different donor blood samples.

Figure 24:
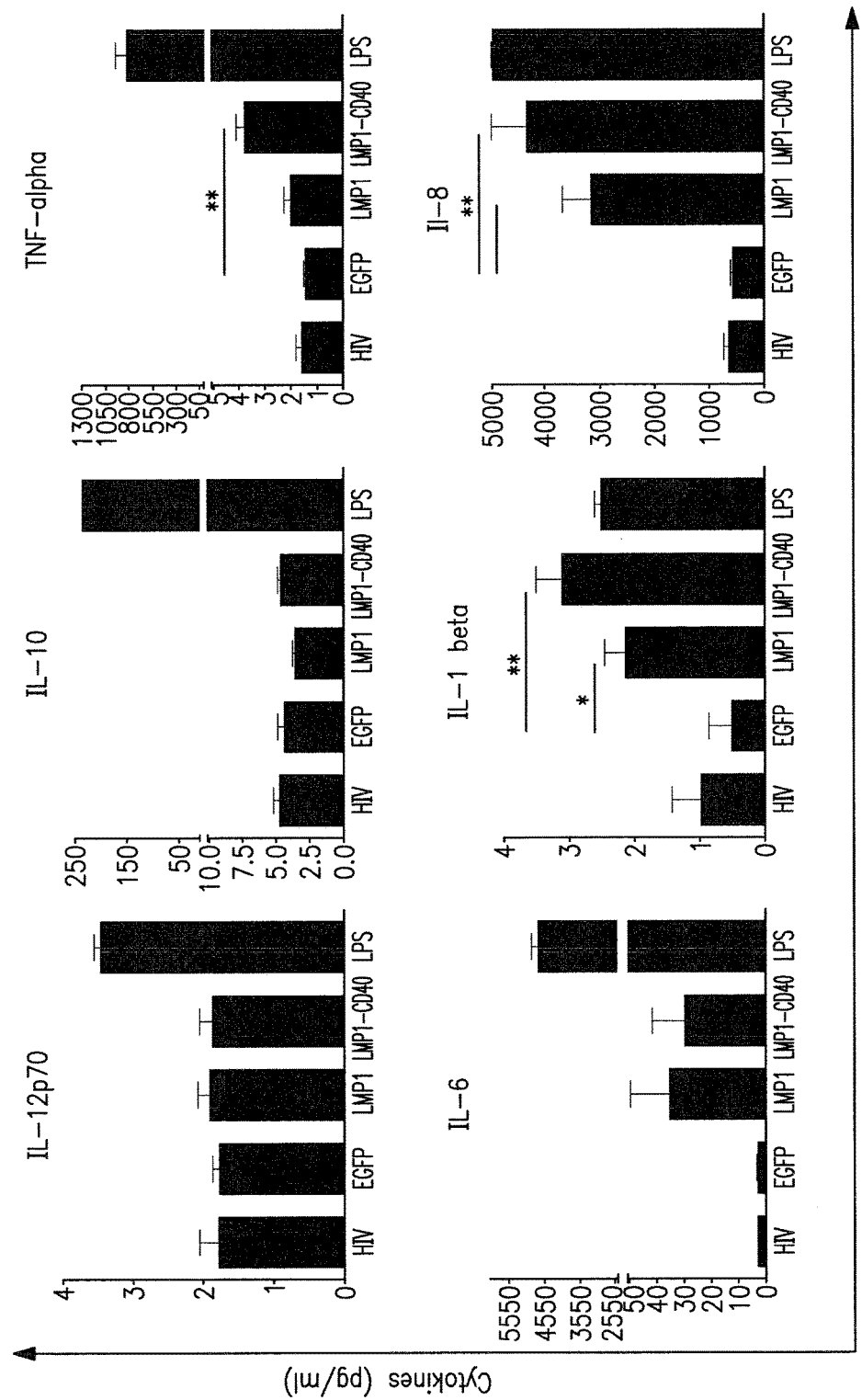

FIG. 24 shows that HIV-1 lentiviruses carrying LMP1 or LMP1-CD40 can activate human DCs in vitro. Cytokines profiles including IL-12p70, IL-10, TNFα, IL-6, IL-1β, and IL-8 are illustrated.

Figure 25:
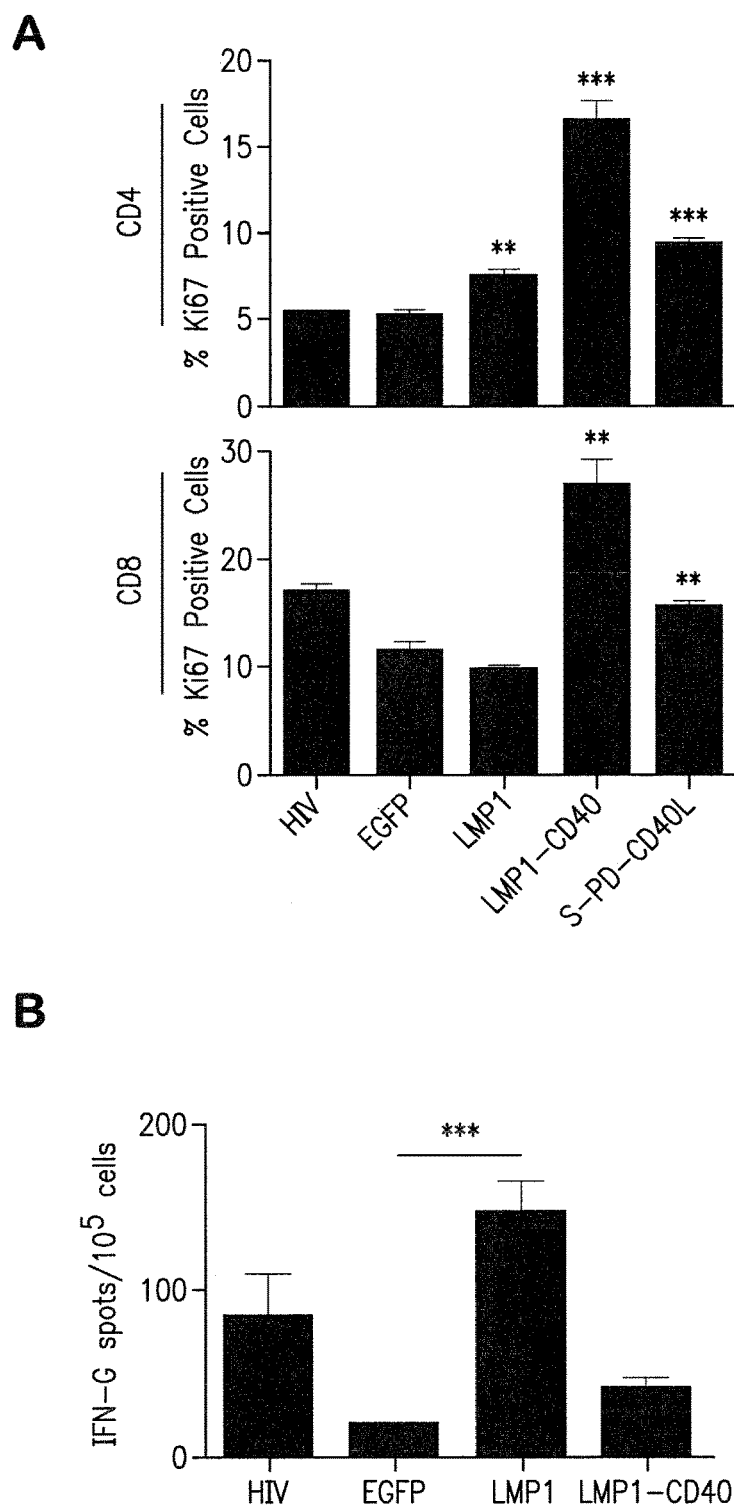

FIG. 25 shows that HIV-LMP1 and HIV-LMP1-CD40 can activate the antigen-presenting function of human DCs. FIG. 24A shows APC function measured as allopresentation in MLR. DCs are transduced with HIV alone or HIV expressing EGFP, LMP1, LMP1-CD40, or SP-D-CD40L and cultured for 6 days. In the presence of neviapine, allogeneic T cells are added (1:10) and cultured for another 5 days. APC function is measured by the proliferation of these added cells as judged by Ki67 staining. HIV-LMP1 augmented CD4+ T cell responses and HIV-LMP1-CD40 augmented both CD4+ and CD8+ T cell responses. FIG. 24B shows APC function measured in an in vitro immunization experiment. Using blood from an HIV-negative donor, DCs are transduced with HIV viruses for 6 days, washed, and then incubated with autologous T cells for 12-days in the presence of 5 U/ml of IL-2 from day 3. The cells are then transferred to ELISPOT plates and restimulated with a 15-mer Gag peptide pool and assayed for IFN-γ spots. Compared to HIV-EGFP, HIV-LMP1 induces a statistically significant increase in de novo cell responses ($p<0.001$).

Figure 26:
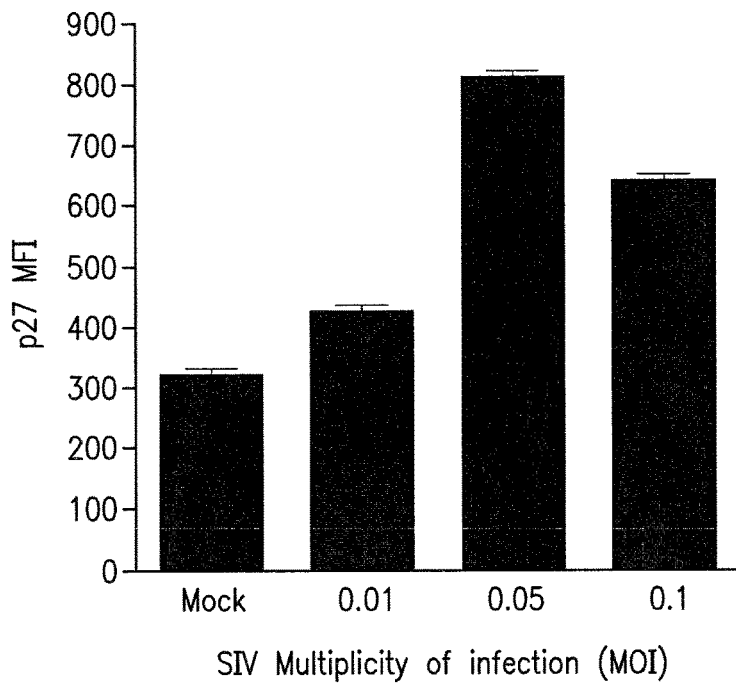

FIG. 26 shows calibrating infectivity and optimization of multiplicity of infection (MOI) of scSIV. To calculate the optimal infection dose, CEM cells are infected with a range of ng/million cells of VSV-G pseudotyped scSIV for 4 days and then stained with FITC anti-p27 antibody and analyzed by flowcytometry. Optimal infectivity can be observed at 50 ng scSIV per million cells (MOI of 0.05).

Figure 27:
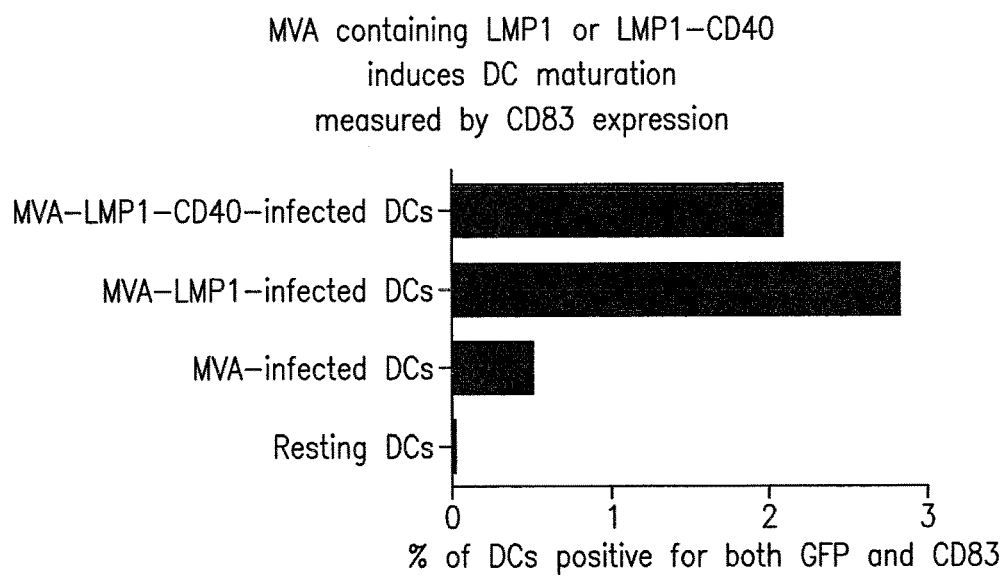

FIG. 27 shows enhanced dendritic cell (DC) maturation by Modified Vaccinia Ankara (MVA) virus containing LMP1 or LMP1-CD40 adjuvant gene cassette. Monocyte-derived dendritic cells (DCs) are prepared by culturing monocytes for 6 days in GM-CSF+IL-4 by standard methods. Recombinant MVA is prepared using the pLW-44 homologous transfer vector that expresses Green Fluorescent Protein (GFP) from the Vaccinia P11 promoter and a second gene from the Vaccinia mH5 promoter. By inserting LMP1 or LMP1-CD40 into the pLW-44 plasmid and then using homologous recombination to transfer LMP1 or LMP1-CD40 into MVA three kinds of recombinant viruses are made: MVA expresses only GFP (recombined with unmodified pLW-44), GFP+LMP1 (recombined with pLW-44 containing LMP1 as the second gene), or GFP+LMP1-CD40 (recombined with pLW-44 containing LMP1-CD40 as the second gene). DCs are transduced with these viruses at a multiplicity of infection (MOI) of 10, cultured for 48 hours, and then analyzed by flow cytometry using phycoerythrin-conjugated anti-CD83 antibody to stain for the CD83 maturation marker. Uninfected resting DCs do not express GFP and express low levels of the CD83 maturation marker. Following infection by MVA expressing only GFP, transduced DCs express both GFP and a low percentage are positive for CD83. In contrast, following infection by MVA expressing both GFP and LMP1 or LMP1-CD40, transduced DCs express both GFP and a higher percentage are positive for CD83. This demonstrates the additive effect of LMP1 or LMP1-CD40 on MVA stimulation of DCs to mature.

Figure 28:
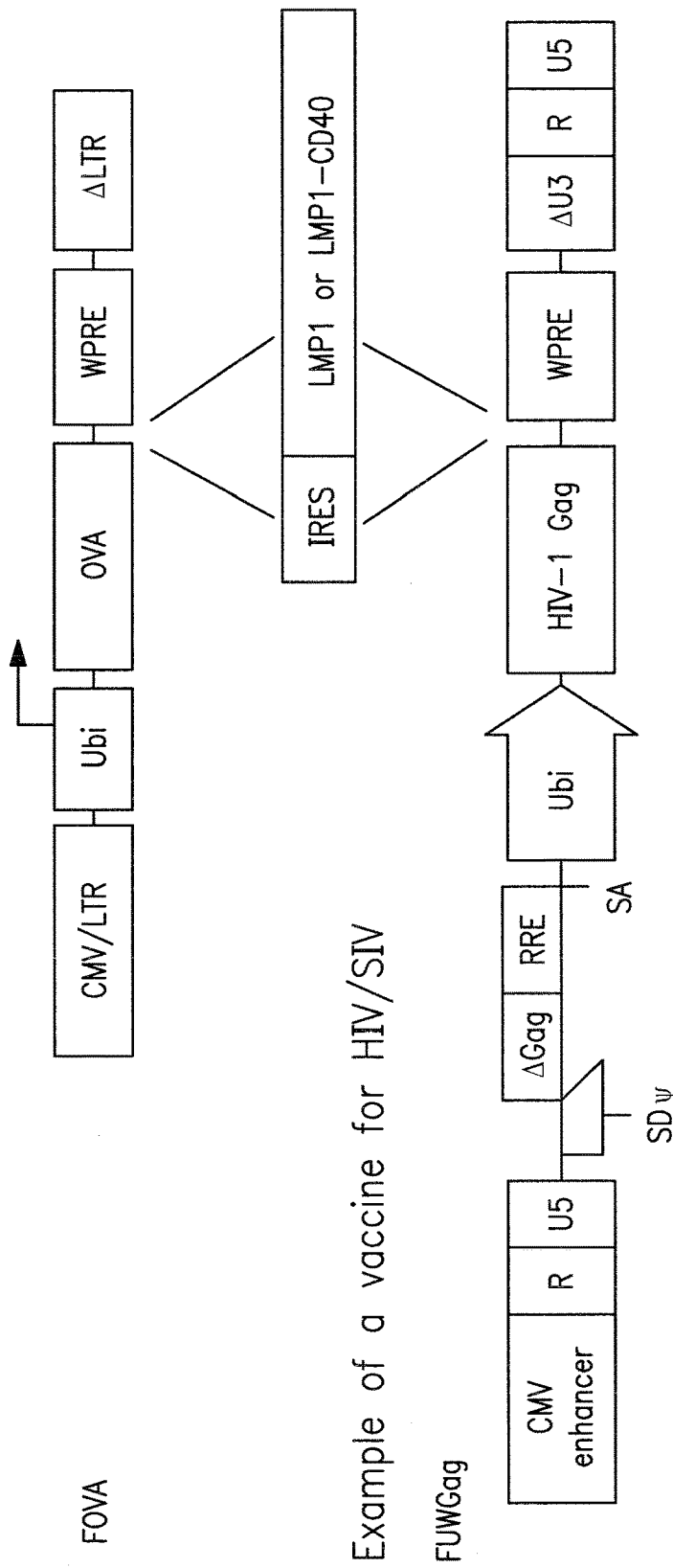

FIG. 28 shows proposed DC-NILV vaccines using LMP1 or LMP1-CD40 based on previously disclosed vaccines. The FOVA construct has been disclosed in Yang et al. (2008) Nature Biotechnology 26:326-334, and the FUWGag construct has been disclosed in Dai Bingbing et al. (2009) Proc Natl Acad Sci 106:20382-20387.

Figure 29:
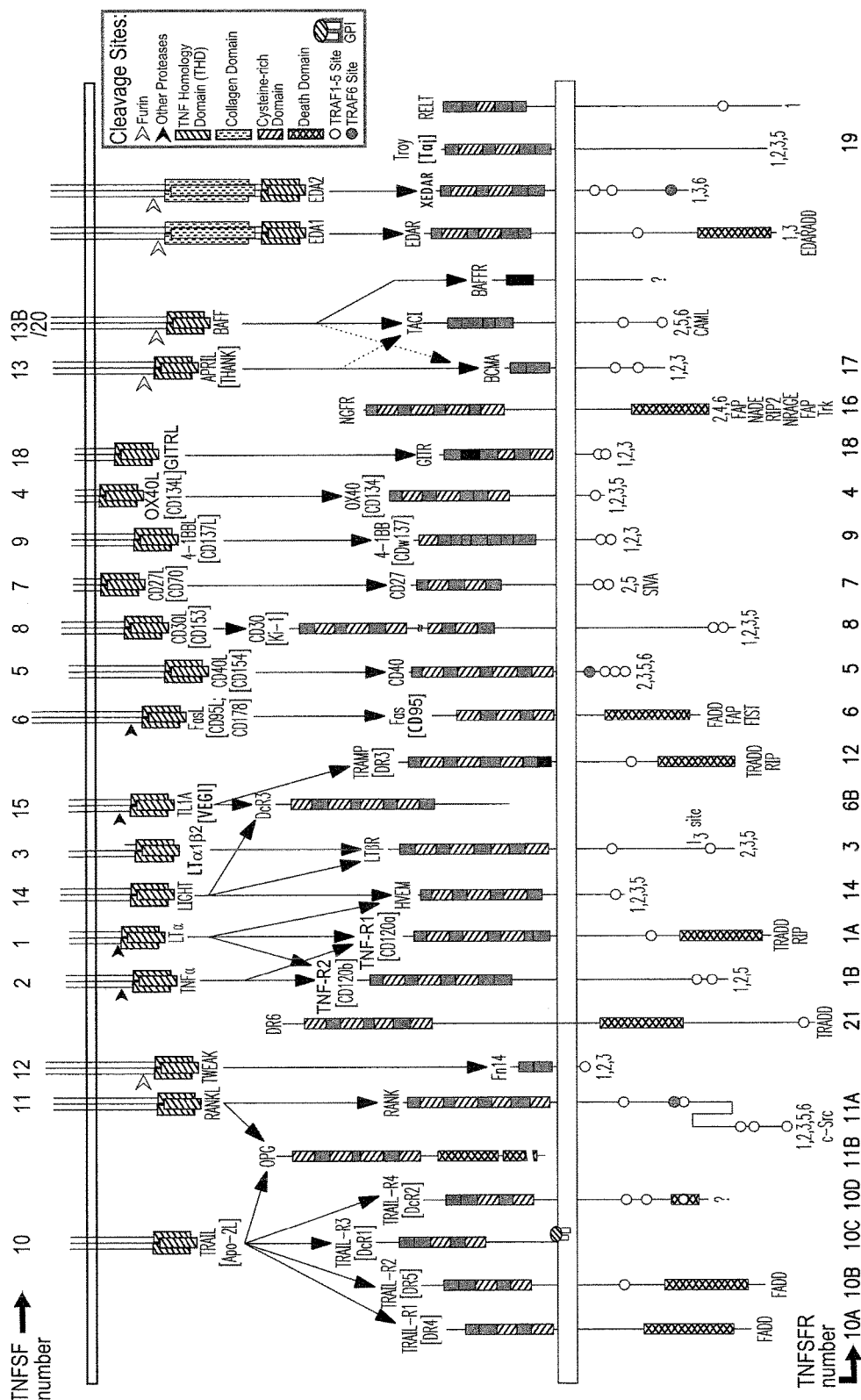

FIG. 29 shows an illustration of TNF Receptor Super-Family and common features among some of the members. Arrows indicate cleavage sites of furin or other proteases. TNF homology domains (THD; shaded boxes), collagen domains (clear boxes), cycsteine-rich domains (dark and shaded boxes), and death domains (dark boxes close to the bottom of the figure) are illustrated.

DETAILED DESCRIPTION OF THE INVENTION

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

It is readily apparent to one skilled in the art that various embodiments and modifications can be made to the invention in this application without departing from the scope and spirit of the invention.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing," and "comprising" are interchangeable and one of skill in the art is cognizant that these terms are open ended terms.

The term "adjuvant" refers to an immunostimulant that triggers activation of antigen-presenting cells such as dendritic cells, macrophages, and B cells. Adjuvants are also understood to provide a "danger" signal indicating that the immune system should go into a state of alert. Without an adjuvant, immune responses may either fail to progress or may be diverted into ineffective immunity or tolerance. Adjuvants are often needed for effective preventative or therapeutic vaccines, or for inducing an anti-tumor immune response.

The term "allogeneic" as used herein, refers to cell types or tissues that are antigenically distinct. Thus, cells or tissue transferred from the same species can be antigenically distinct.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates. Exemplary organisms include but are not limited to, *Helicobacters, Campylobacters, Clostridia, Corynebacterium diphtheriae, Bordetella pertussis,* influenza virus, parainfluenza viruses, respiratory syncytial virus, arenaviruses, bunhaviruses, flaviviruses, filoviruses, West Nile virus, Japanese Encephalitis virus, Venezuelan equine encephalitis virus, Eastern equine encephalitis virus, Western equine encephalitis virus, *Borrelia burgdorfei, Plasmodium,* herpesviruses, human immunodeficiency virus, papillomavirus, *Vibrio cholera, E. coli,* measles virus, rotavirus, mycobacteria, staphylococci, streptococci, shigella, *Salmonella typhi,* and *Neisseria gonorrhea,* Therefore, a skilled artisan realizes that any macromolecule, including virtually all proteins or peptides, can serve as antigens. Furthermore, antigens can be derived from recombinant or genomic DNA. A skilled artisan realizes that any DNA, which contains nucleotide sequences or partial nucleotide sequences of a pathogenic genome or a gene or a fragment of a gene for a protein that elicits an immune response results in synthesis of an antigen. Furthermore, one skilled in the art realizes that the present invention is not limited to the use of the entire nucleic acid sequence of a gene or genome. It is readily inherent that the present invention includes, but is not limited to, the use of partial nucleic acid sequences of more than one gene or genome and that these nucleic acid sequences are arranged in various combinations to elicit the desired immune response.

The term "antigen-presenting cell" is any of a variety of cells capable of displaying, acquiring, or presenting at least one antigen or antigenic fragment on (or at) its cell surface. In general, the term "antigen-presenting cell" can be any cell that accomplishes the goal of the invention by aiding the enhancement of an immune response (i.e., from the T-cell or B-cell arms of the immune system) against an antigen or antigenic composition. Such cells can be defined by those of skill in the art, using methods disclosed herein and in the art. As is understood by one of ordinary skill in the art, and used herein certain embodiments, a cell that displays or presents an antigen normally or preferentially with a class II major histocompatibility molecule or complex to an immune cell is an "antigen-presenting cell." In certain aspects, a cell (e.g., an APC cell) may be fused with another cell, such as a recombinant cell or a tumor cell that expresses the desired antigen. Methods for preparing a fission of two or more cells are well known in the art. In some cases, the immune cell to which an antigen-presenting cell displays or presents an antigen is a CD4+ T or a CD8+ T cell. Additional molecules expressed on the APC or other immune cells may aid or improve the enhancement of an immune response. Secreted or soluble molecules, such as for example, cytokines and adjuvants, may also aid or enhance the immune response against an antigen. Such molecules are well known to one of skill in the art, and various examples are described herein.

The term "cancer" as used herein is defined as a hyperproliferation of cells whose unique trait—loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The terms "cell," "cell line," and "cell culture" as used herein may be used interchangeably. All of these terms also include their progeny, which are any and all subsequent generations. It is understood that all progeny may not be identical due to deliberate or inadvertent mutations.

As used herein, the term "co-extensive in space and time" refers to the concordance of two functional domains in the same cellular environment at the same time. More particularly, it refers to the concordance of an antigen and an adjuvant in the same cellular environment at the same time. Most especially, it refers to a self-adjuvanting construct that associates an antigen or antigens with an adjuvant in the same cellular environment at the same time.

As used herein, the term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There are times when the full or partial genomic sequence is preferred, such as where the non-coding regions are required for optimal expression or where non-coding regions such as introns are to be targeted in an antisense strategy.

The term "dendritic cell" (DC) is an antigen-presenting cell existing in vivo, in vitro, ex vivo, or in a host or subject, or which can be derived from a hematopoietic stem cell or a monocyte. Dendritic cells and their precursors can be isolated from a variety of lymphoid organs, e.g., spleen, lymph nodes, as well as from bone marrow and peripheral blood. The DC has a characteristic morphology with thin sheets (lamellipodia) extending in multiple directions away from the dendritic cell body. Typically, dendritic cells express high levels of major histocompatibility complex (MHC) and costimulatory (e.g., B7-1 and B7-2) molecules. Dendritic cells can induce antigen specific differentiation of T cells in vitro, and are able to initiate primary T cell responses in vitro and in vivo.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are described infra.

As used herein, the term "ex vivo" refers to "outside" the body. One of skill in the art is aware that ex vivo and in vitro can be used interchangeably under certain circumstances.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular restenosis, atherosclerosis, or inflammatory bowel disease.

As used herein, the term "gene" is defined as a functional protein, polypeptide, or peptide-encoding unit. As will be understood by those in the art, this functional term includes genomic sequences, cDNA sequences, and smaller engineered gene segments that express, or is adapted to express, proteins, polypeptides, domains, peptides, fusion proteins, and mutants.

The term "immunogenic composition" or "immunogen" refers to a substance that is capable of provoking an immune response. Examples of immunogens include, e.g., antigens, autoantigens that play a role in induction of autoimmune diseases, and tumor-associated antigens expressed on cancer cells.

As used herein, the term "intracellular signaling domain" generally refers to a cytoplasmic tail of a membrane-associated receptor molecule, e.g., the cytoplasmic tail of CD40. The term also includes signaling molecules like that in the zeta chain of CD3 or adaptor molecules that engage downstream cell signaling pathways.

As used herein, the term "multimerizing" or "multimerization" refers to the complexation of three or more subunits into a single entity. As such, multimerization is distinct from "dimerizing" or "dimerization" which refers to the complexation of exactly two subunits into a single entity.

As used herein, the term "pharmaceutically or pharmacologically acceptable" refers to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

As used herein, the term "polynucleotide" is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means. Furthermore, one skilled in the art is cognizant that polynucleotides include mutations of the polynucleotides, include but are not limited to, mutation of the nucleotides, or nucleosides by methods well known in the art.

As used herein, the term "polypeptide" is defined as a chain of amino acid residues, usually having a defined sequence. As used herein the term polypeptide is interchangeable with the terms "peptides" and "proteins."

As used herein, the term "promoter" is defined as a DNA sequence recognized by the synthetic machinery of the cell, or introduced synthetic machinery, required to initiate the specific transcription of a gene.

As used herein, the term "self-adjuvanting" refers to a microbe or vector that carries with it both its own antigens and an adjuvanting moiety. The microbe may be a virus, bacterium, fungus, parasite, or protozoa. A vector construct may also be self-adjuvanting if it encodes both an antigen or antigens and an adjuvanting moiety.

In the present invention, the term "therapeutic construct" may also be used to refer to the expression construct or transgene. One skilled in the art realizes that the present invention utilizes the expression construct or transgene as a therapy to treat hyperproliferative diseases or disorders, such as cancer, thus the expression construct or transgene is a therapeutic construct or a prophylactic construct.

The term "transfection" and "transduction" refer to the process by which an exogenous DNA sequence is introduced into a eukaryotic host cell. Transfection is the non-viral delivery of nucleic acids (either DNA or RNA) and can be achieved by any one of a number of means including electroporation, microinjection, gene gun delivery, retroviral infection, lipofection, polymer-mediated delivery, and the like. Transfection refers to the delivery of nucleic acids by a virus or viral vector where the nucleic acids are typical DNA for a DNA virus and RNA for an RNA virus. Also, for bacteria that enter cells such as *Salmonella* or *Listeria*, plasmid DNA can be introduced into these bacteria which then carry that DNA into the eukaryotic host cell, a process called "bactofection."

As used herein, the term "syngeneic" refers to cells, tissues or animals that have the same genotype. For example, identical twins or animals of the same inbred strain. Syngeneic and isogeneic can be used interchangeable.

The term "subject" as used herein includes, but is not limited to, an organism or animal; a mammal, including, e.g., a human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

As used herein, the term "under transcriptional control" or "operatively linked" is defined as the promoter is in the correct location and orientation in relation to the nucleic acid to control RNA polymerase initiation and expression of the gene.

As used herein, the terms "treatment," "treat," "treated," or "treating" refer to prophylaxis and/or therapy. When used with respect to an infectious disease, for example, the term refers to a prophylactic treatment which increases the resistance of a subject to infection with a pathogen or, in other words, decreases the likelihood that the subject will become infected with the pathogen or will show signs of illness attributable to the infection, as well as a treatment after the subject has become infected in order to fight the infection, e.g., reduce or eliminate the infection or prevent it from becoming worse.

As used herein, the term "vaccine" refers to a formulation which contains the composition of the present invention and which is in a form that is capable of being administered to an animal. Typically, the vaccine includes a conventional saline or buffered aqueous solution medium in which the composition of the present invention is suspended or dissolved. In this form, a composition of the present invention can be used conveniently to prevent, ameliorate, or otherwise treat a condition. Upon introduction into a subject, the vaccine is able to provoke an immune response including, but not limited to, the production of antibodies, cytokines and/or other cellular responses.

A good example of the purposeful introduction of an adjuvant into a vaccine was reported by Ruby et al. 1995) Nature Medicine 1: 437-441. These authors studied the vaccinia virus, a live viral vaccine that nevertheless replicates very strongly in mice unless controlled by the host response. In this case, the coding sequence for CD40 ligand (CD40L) was genetically introduced into recombinant vaccinia virus and tested in mice. When the vaccinia virus also led to the expression of CD40L, the replication of the virus was severely curtained by host responses.

Another example was the report of Lin et al. (2009) J Virol 83: 1216-1227. They found that incorporating CD40L onto the surface of a simian immunodeficiency virus (SIV) could lead to enhanced antibody and cellular immune responses. In this case, the SIV was further engineered so that it could only undergo one round of infection ("single-cycle" virus), which ensured that it could not by itself lead to persistent SIV infection.

CD40L is normally a membrane molecule. Consequently, the CD40L adjuvant molecule appears on the surface of these enveloped (i.e., membrane-bearing) viruses. To activate immune cells, these vaccines must engage the extracellular portion of the CD40 receptor. The resulting CD40L-mediated stimulation of the CD40 receptor can occur on either the same cells infected by the vaccinia-CD40L or SIV-CD40L constructs or on adjacent cells. The risk of activating an adjacent cell is that the adjacent cell might not be an antigen-presenting cell or, if it is an antigen-presenting cell, it might not have the proper antigen (e.g., vaccinia antigens in the case of vaccinia-CD40L or SIV antigens in the case of SIV-CD40L). Thus, expressing CD40L as a membrane protein on a virus or microbe does not ensure that the antigen and adjuvant are co-extensive in space and time.

As a way of solving this problem, gene therapy approaches has been developed to target dendritic and activate them through the CD40 pathway. The method relies on the cytoplasmic tale of CD40 which contains amino acid sequences that engage signal transduction molecules, chiefly the TNF-Receptor Activation Factors or TRAFs of which TRAF6 is one of the most important. The CD40 intracellular signaling domain can be fused with a myristylation sequence that permitted the fusion protein to attach itself to the inner leaflet of the plasma membrane. As a further step, the fusion construct includes a sequence taken from the FK506 binding protein (FKBP12) that allowed the fusion protein to be dimerized by a drug composed of two FK506 moieties joined together (e.g., AP20187). The result is a chemically induced dimerization system (CID). When the entire genetic construct is expressed under the control of the CD11c promoter that is preferentially activated in myeloid dendritic cells and introduced into these cells, then the entire system mimics CD40 activation of dendritic cells once the chemical dimerizer (e.g., AP20187) is added. The drawbacks to this system include: (1) the myristylation-FK506 binding domain-CD40 cytoplasmic region fusion construct requires a genetic vector to introduce it into cells or else stable transgenic cells must be produced; (2) the chemical dimerizer must be added and its pharmacology must be separately controlled; (3) if the expression of the activated CD40 signaling domain inside CD11c dendritic cells is considered to be an adjuvant, no method was provided to couple this system to an antigen such that the antigen and adjuvant are co-extensive in space and time; and (4) the description of the CID system infers that it works by dimerization. The last point is important because the intracellular domain of CD40 signals best when it is present as a trimer, yet the description of Hanks et al. (2005) Nat Med 11: 130-137, teaches away from this by implying that a dimer is sufficient.

Consequently, what is needed is a more general way to ensure that an antigen and adjuvant are co-extensive in space and time. In one aspect, this is performed without the need for a chemical crosslinker, e.g., through a self-assembling intracellular complex. Using CD40 as an example, such a self-assembling complex should lead to multimers of three or more CD40 intracellular cytoplasmic domains as an adjuvant and this complex would need to be operatively linked to the antigen in order that the antigen and adjuvant be co-extensive in space and time.

Concerning a self-assembling intracellular complex that leads to signaling through the CD40 pathway, this is naturally present in the Epstein-Barr virus (EBV) in the form of the latent membrane protein 1 (LMP1). LMP1 has an N-terminus containing six transmembrane regions some of which interact with others to form a multimeric patch in the plane of the membrane. The C-terminal region of LMP1 contains TRAF-binding motifs that signal in a similar manner to those from the CD40 intracellular region.

Related to LMP1 is an artificial fusion protein containing the multimerizing, membrane-associated N-terminus of LMP1 conjoined with the intracytoplasmic domain of CD40, LMP1-CD40. This membrane-associated intracellular fusion protein mimics the constitutive signaling of CD40 without the need for an external ligand.

LMP1 and LMP1-CD40 exemplify defined amino acid sequences that carry with them the ability to activate the CD40 signaling pathway. CD40 signaling is known to activate dendritic cells to present antigen to T cells. CD40 signaling is known to activate B cells to present antigen to T cells. CD40 signaling is known to mature B cells into antibody-producing cells. In particular, CD40 activated B cells undergo "class switching" of their antibody production from IgM to IgG or in some circumstances to IgA, and this can be replicated by LMP1.

However, prior to the present invention, it was not recognized that LMP1 or LMP1-CD40 could be used as adjuvants and there was no suggestion as to how this might be accomplished. One of the central, non-obvious, and inventive aspects of the present invention is that it envisions LMP1 or LMP1-CD40 as portable adjuvant compositions that can be introduced into microbes, most preferably viruses, or tumor cells. These microbes or tumor cells carry their own antigens with them. By placing LMP1 or LMP1-CD40 directly into them, the antigen and adjuvant become co-extensive in space and time, which is an important feature of the present invention.

While the above discussion relates to the CD40 signaling pathway, the application of the present invention extends to other similar receptor molecules. These receptors are collectively known as the TNF Receptor SuperFamily (TNFRSF). As a general rule, signaling by each and any of these receptors requires that their cytoplasmic domains be multimerized into complexes of three or more amino acid strands. Just as LMP1-CD40 combines the multimerizing domain of LMP1 with the intracellular signaling domain of the CD40 receptor into an amino acid sequence cassette, so too the present invention anticipates fusions of LMP1 with the intracellular signaling domains of other TNFRSFs. Examples include LMP1-4-1BB, LMP1-OX40, LMP1-CD27, LMP1-RANK, LMP1-BAFF-R, etc. Significantly, these other TNFRSFs are expressed on a different range of cells than is CD40 and their stimulation has different effects. For example, the receptors for a proliferation-inducing ligand (APRIL) mediate cell growth such that their activation could be used to promote wound healing.

In the above discussion, note is made of fusing the LMP1 N-terminal domain to the intracellular signaling domains of TNFRSFs such that the fusion protein self-assembles into a multimeric complex of three or more chains. While exemplary, the LMP1 N-terminal domain is not the only amino acid sequence that can be used in this manner.

The present invention provides compositions and methods which stimulate the immune system to defend the host from microbes and hyperproliferative diseases including cancer. More particularly, the present invention provides compositions in which an amino acid sequence of a multimerizing domain is fused to an intracytoplasmic signaling domain that must be multimerized into a complex of three or more identical chains in order to provide an activating signal to a cell. The compositions of the present invention can be used as an adjuvant to bolster the immune response to a microbe or a tumor cell. In some embodiments, the composition of the present invention can be used to make more effective preventative or therapeutic vaccines or to elicit the immune control of tumors.

Certain embodiments of the present invention include an expression construct comprising a polynucleotide promoter sequence, a polynucleotide sequence encoding the multimerization-intracellular signaling fusion cassette, all operatively linked. It is envisioned that the expression construct is comprised within a vector forming an expression vector; the vector is selected from the group consisting of a viral vector, a bacterial vector, and a mammalian vector. The multimerization-intracellular signaling cassette can be comprised of any combination of a multimerization domain with an intracellular signaling domain where the multimerization domain leads to the complexation of three or more of the intracellular signaling domains.

Certain embodiments of the present invention are comprised of a virus or vector into which the multimerization-intracellular signaling cassette has been inserted. There are at least two methods for determining where in the virus or vector this cassette should be inserted: (1) if the codons of a viral or vector gene can be deleted or mutated into a non-functional condition, then this location in the virus or vector is a candidate location for inserting the cassette. Most preferably, but not essentially, number of nucleic acid bases encoding the deleted or mutated viral or vector gene should be similar to the number of nucleic bases of the cassette being inserted (e.g., a dispensable viral or vector gene of about 400 bp can be replaced by cassette of 150 to 600 bp); or (2) reports in the literature may already describe how foreign genes can be inserted into a virus or vector. For example, enhanced green fluorescent protein (EGFP), beta-galactosidase, thymidine kinase, the neo gene for resistance to the toxicity G418, beta-lactamase, and other enzymes have already been inserted into many viruses and vectors such that the viruses and vectors retain their functions of interest. Other examples of inserts that may already be described in the literature include affinity tags for example calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin. Thus, those skilled in the art can readily determine how to replace the enzyme or affinity tag insert with a multimerization-intracellular signaling cassette of the present invention.

Other embodiments of the present invention include a transduced cell, in which the cell is transduced with an expression vector containing the multimerization-intracellular signaling cassette. In one aspect, an antigen-presenting cell, for example a dendritic cell, can be loaded with antigen and transduced with latent membrane protein 1 (LMP1) or LMP1-CD40 and then delivered to the host to initiate an immune response.

In another embodiment, a multimerization-intracellular signaling cassette can be transduced with an expression vector into a tumor cell. In another aspect where LMP1 or LMP1-CD40 is used, the tumor cell membrane can carry the cassette. Since tumor cells are known to shed microvesicles that transfer membrane molecules including MHC Class I with antigen to other cells by a process known as trogocytosis or transfer by small membrane fragments known as exosomes, this is a mechanism whereby a tumor cell carrying the multimerization-intracellular signaling adjuvant cassette can donate antigen and adjuvant to antigen-presenting cells.

Another embodiment of the present invention is a pharmaceutical composition including the virus or expression vector or a cell transduced with same, wherein the virus or expression vector leads to the expression of the multimerization-intracellular signaling cassette. The virus or expression vector used for this pharmaceutical composition includes a polynucleotide promoter sequence, a first polynucleotide sequence encoding a multimerizing domain, and a second polynucleotide sequence encoding an intracellular signaling domain such that the second domain is in the correct reading frame with the multimerizing domain. These sequences may be followed by either a transcriptional termination signal and polyadenylation domain, or followed by an internal ribosome entry sequence (IRES) followed by another separate coding sequence. The result is an operatively linked construct that leads to the transcription and translation of the multimerization-intracellular signaling cassette in a cell transfected by the pharmaceutical composition.

As a further modification, a spacer or linker can be inserted between the multimerization domain and the intracellular signaling domain of the multimerization-intracellular signaling cassette. Exemplary of such spacers or linkers are nucleic acid sequences encoding the amino acid sequences GlyGlyGlyGlySerGlyGlyGlyGlySerGlyGly-GlyGlySer (SEQ ID NO: 3), the hinge sequence from IgG-GluProLysSerCysAspLysThrHisThrCys-ProPro-CysProAlaProGluLeuLeuGlyGlyPro (SEQ ID NO: 4), or one or more Gly or Ala residues. Without undue effort or experimentation, those skilled in the art can prepare variants of the basic multimerization-intracellular signaling cassette containing such linkers and test them for their functional effects, choosing the most efficacious construct for further application according to the present invention.

A further embodiment of the present invention includes a method for modulating an immune response in a subject. The method includes the step of administering to the subject a virus or vector of the present invention. The virus or vector is expressed in an antigen-presenting cell, for example a dendritic cell or B cell. The virus or expression vector used for this pharmaceutical composition includes a polynucleotide promoter sequence, a first polynucleotide sequence encoding a multimerizing domain, and a second polynucleotide sequence encoding an intracellular signaling domain such that the second domain is in the correct translational reading frame with the multimerizing domain, all operatively linked.

Another embodiment includes a method of modulating an immune response in a subject. The method includes the steps of: transducing or transfecting an antigen-presenting cell with a virus or expression vector, wherein the virus or expression vector includes a polynucleotide promoter sequence, a polynucleotide sequence encoding the multimerizing-intracellular signaling cassette (with or without a spacer or linker), and a transcriptional terminator or IRES, all operatively linked; and administering to the subject transduced antigen-presenting cells. Of note, if the method uses transduction of mRNA, no promoter sequence is needed. In one aspect, the transduced or transfected antigen-presenting cells enhance the immune response in the subject. In another aspect, the transduced or transfected antigen-presenting cells are administered to the subject simultaneously to administration of an antigen or that the antigen is already encoded by the virus or expression vector or already present in the host subject.

Another embodiment of the present invention is a method of inducing a regulated immune response against an antigen in a subject. The method includes the steps of: transducing or transfecting an antigen-presenting cell with a virus or expression vector, wherein the virus or expression vector includes a polynucleotide promoter sequence, a polynucleotide sequence encoding the multimerizing-intracellular signaling cassette (with or without a spacer or linker), and a transcriptional terminator or IRES, all operatively linked; loading transduced or transfected antigen-presenting cells with the antigen; and administering transduced or transfected, loaded antigen-presenting cells to the subject thereby effecting a cytotoxic T lymphocyte and natural killer cell anti-tumor antigen immune response. In one aspect, the transduced or transfected, loaded antigen-presenting cells are administered to the subject intradermally, subcutaneously, intranodally or intralymphatically. In another aspect, the antigen-presenting cells are transduced or transfected with the virus or expression vector in vitro or ex vivo prior to administering to the subject.

Loading the antigen-presenting cells with an antigen can be accomplished utilizing standard methods, for example, pulsing, transducing, transfecting, and/or electrofusing. In one aspect, the antigen can be nucleic acids (DNA or RNA), proteins, protein lysate, whole cell lysate, or antigen proteins linked to other proteins, e.g., heat shock proteins.

In various embodiments, the antigens can be derived or isolated from a pathogenic microorganism for example viruses including Human immunodeficiency virus (HIV), influenza, Herpes simplex, human papilloma virus, Hepatitis B, Hepatitis C, Cytomegalovirus (CMV) and the like. The antigen may be derived or isolated from pathogenic bacteria such as from *Chlamydia, Mycobacteria, Legionella, Meningiococcus*, Group A *Streptococcus, Salmonella, Listeria*,

*Hemophilus influenzae*, and the like. In one aspect, the antigen may be derived or isolated from pathogenic yeast including *Aspergillus*, invasive *Candida, Nocardia, Histoplasmosis, Cryptosporidia* and the like. The antigen may be derived or isolated from a pathogenic protozoan and pathogenic parasites including, but not limited to *Pneumocystis carinii, Trypanosoma, Leishmania, Plasmodium* and *Toxoplasma gondii*.

In certain embodiments, the antigen includes an antigen associated with a preneoplastic or hyperplastic state. Antigens may also be associated with, or causative of cancer. In one aspect, such antigens include tumor specific antigen, tumor associated antigen (TAA) or tissue specific antigen, epitope thereof, and epitope agonist thereof. In another aspect, such antigens include but are not limited to carcinoembryonic antigen (CEA) and epitopes thereof such as CAP-1, CAP-1-6D and the like, MART-1, MAGE-1, MAGE-3, GAGE, GP-100, MUC-1, MUC-2, point mutated ras oncogene, normal and point mutated p53 oncogenes, PSMA, tyrosinase, TRP-1 (gp75), NY-ESO-1, TRP-2, TAG72, KSA, CA-125, PSA, HER-2/neu/c-erb/B2, BRC-I, BRC-II, bet-abl, pax3-fkhr, ews-fli-1, modifications of TAAs and tissue specific antigen, splice variants of TAAs, epitope agonists, and the like.

Another embodiment is a method of treating and/or preventing a disease and/or disorder. The method includes administering to a subject an effective amount of a virus or expression vector of the present invention to treat and/or prevent the disease and/or disorder, wherein the expression vector includes a polynucleotide promoter sequence, a polynucleotide sequence encoding the multimerizing-intracellular signaling cassette (with) or without a spacer or linker), a transcriptional terminator or IRES, all operatively linked. Of note, if the method uses transduction of mRNA, no promoter sequence is needed. An exemplary multimerizing-intracellular signaling cassette is LMP1 or LMP1-CD40.

In certain embodiments, the disease is a hyperproliferative disease, which can also be further defined as cancer. In still further embodiments, the cancer is melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder. The cancer may include a tumor comprised of tumor cells. For example, tumor cells may include, but are not limited to melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In other embodiments, the hyperproliferative diseases include rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, psoriasis, or combinations thereof.

Yet further, another embodiment is a method of treating a disease and/or disorder. The method includes administering to a subject an effective amount of a transduced or transfected antigen-presenting cell to treat the disease and/or disorder, wherein the transduced transfected antigen-presenting cell is transduced or transfected with an expression vector including a polynucleotide promoter sequence, a polynucleotide sequence encoding the multimerizing-intracellular signaling cassette (with or without a spacer or linker), and a transcriptional terminator or IRES, all operatively linked. In one aspect, the multimerizing-intracellular signaling cassette includes a multimerization domain operatively linked to the intracellular signaling domain of a TNFRSF, more specifically the CD40 cytoplasmic domain. In another aspect, the transduced or transfected antigen-presenting cells can be administered to the subject intradermally, subcutaneously, or intranodally. The antigen-presenting cells can be transduced or transfected with the virus or expression vector in vitro prior to administering to the subject. The method may further include electrofusing the transduced or transfected antigen-presenting cell to a tumor cell. In certain embodiments, the tumor cell is syngeneic, or allogeneic. The method may also further includes transfecting the transduced or transfected antigen-presenting cell with tumor cell mRNA and/or pulsing the transduced or transfected antigen-presenting cell with tumor cell protein lysates and/or pulsing the transduced or transfected antigen-presenting cell with heat shock proteins linked to tumor cell polypeptides.

Another embodiment is a method of treating a subject with cancer. The method includes administering to the patient an effective amount of a transduced or transfected antigen-presenting cell to treat the cancer. In one aspect, the transduced or transfected antigen-presenting cell is transduced with an expression vector or viral construct including a polynucleotide promoter sequence, a polynucleotide sequence encoding the multimerizing-intracellular signaling cassette (with or without a spacer or linker), and a transcriptional terminator or IRES, all operatively linked; and administering at least one other anticancer treatment. Of note, if the method uses transduction of mRNA, no promoter sequence is needed. In another aspect, the anticancer treatment is selected from the group consisting of chemotherapy, immunotherapy, surgery, radiotherapy, gene therapy and biotherapy.

In another embodiment, the multimerizing-intracellular signaling cassette (with or without a spacer or linker) can be delivered to a tumor in vivo using a microbe or virus. *Listeria* is an example of a bacterium that preferentially targets tumors and can transfer plasmid DNA to eukaryotic cells ("bactofection"). Oncolytic viruses are those that preferentially infect tumor cells in vivo. Examples of oncolytic viruses include adenoviruses, reoviruses, alphaviruses, Herpes Simplex virus, Newcastle disease virus, Coxsackie B virus, Coxsackie A21 virus, Sindbis virus, measles virus, poliovirus, vesicular stomatitis virus, myxoma virus, vaccinia virus and other poxviruses, Sendai virus, and influenza virus. In this embodiment, the microbe or oncolytic virus containing the multimerizing-intracelluar signaling cassette is injected either intravenously, subcutaneously, or directly into the tumor or tumor bed. In one aspect, the composition is injected into the space left after a tumor has been surgically removed, e.g., the space in the brain tissue following surgical removal of glioblastoma.

Intracellular signaling domains of the TNF Receptor SuperFamily (TNFRSF): The official nomenclature of the TNFRSFs is maintained by the Human Genome Organization (HUGO) at following URL that was accessed on Mar. 22, 2010 at would wide web genenames.org/genefamily/tnfrsf.php. While definitive information on the human proteins follow below, the skilled artisan would be able to determine similar information on TNFRSFs from non-human mammals, birds, and fish, as well as allelic variants of the reference sequences.

CD27 is GenBank Accession # M63928. It is UniProtKB/SwissProt reference # P26842, which gives its intracytoplasmic signaling domain as amino acids 213-260.

CD40 is GenBank Accession # X60592. It is UniProtKB/SwissProt reference # P25942, which gives its intracytoplasmic signaling domain as amino acids 216-277. However, for the constructs reported here, amino acids 220-277 were used to provide an extra distance from the plasma membrane.

Fas is GenBank Accession # M67454 it is UniProtKB/SwissProt reference # P25445, which gives its intracytoplasmic signaling domain as amino acids 191-335.

Lymphotoxin beta receptor (LTBR) is GenBank Accession # L04270. It is UniProtKB/SwissProt reference # P36941, which gives its intracytoplasmic signaling domain as amino acids 239-435.

Nerve growth factor receptor (NGFR) is GenBank Accession # M14764. It is UniProtKB/SwissProt reference # P08138, which gives its intracytoplasmic signaling domain as amino acids 273-427.

Tumor necrosis factor receptor superfamily member 1A (TNFRSF1A) is GenBank Accession # M75866. It is UniProtKB/SwissProt reference # P19438, which gives its intracytoplasmic signaling domain as amino acids 235-455.

Tumor necrosis factor receptor superfamily member 1B (TNFRSF1B) is GenBank Accession # M32315. It is UniProtKB/SwissProt reference # P20333, which gives its intracytoplasmic signaling domain as amino acids 288-461.

Tumor necrosis factor receptor superfamily member 4 (TNFRSF4 or OX40) is GenBank Accession # X75962. It is UniProtKB/SwissProt reference # P43489, which gives its intracytoplasmic signaling domain as amino acids 236-277.

Tumor necrosis factor receptor superfamily member 8 (TNFRSF8 or CD30) is GenBank Accession # M83554. It is UniProtKB/SwissProt reference # P28908, which gives its intracytoplasmic signaling domain as amino acids 408-595.

Tumor necrosis factor receptor superfamily member 9 (TNFRSF9, CD137, or 4-1BB) is GenBank Accession # L12964. It is UniProtKB/SwissProt reference # Q07011, which gives its intracytoplasmic signaling domain as amino acids 214-255.

Tumor necrosis factor receptor superfamily member 10A (TNFRSF10A, DR4, Apo2, or TRAILR-1) is GenBank Accession # U90875. It is UniProtKB/SwissProt reference # O00220, which gives its intracytoplasmic signaling domain as amino acids 263-468.

Tumor necrosis factor receptor superfamily member 10B (TNFRSF10B, DR5, or TRAIL-R2) is GenBank Accession # AF012628. It is UniProtKB/SwissProt reference # O14763, which gives its intracytoplasmic signaling domain as amino acids 232-440.

Tumor necrosis factor receptor superfamily member 10D (TNFRSF10D, R5, or TRAIL-R2) is GenBank Accession # AF029761. It is UniProtKB/SwissProt reference # Q9UBF6, which gives its intracytoplasmic signaling domain as amino acids 233-386.

Tumor necrosis factor receptor superfamily member 11A (TNFRSF11A or RANK) is GenBank Accession # AF018253. It is UniProtKB/SwissProt reference Q9Y6Q6, which gives its intracytoplasmic signaling, domain as amino acids 234-616.

Tumor necrosis factor receptor superfamily member 12A (TNFRSF12A, FN14, or TweakR) is GenBank Accession # AB035480. It is UniProtKB/SwissProt reference Q9NP84, which gives its intracytoplasmic signaling domain as amino acids 102-129.

Tumor necrosis factor receptor superfamily member 13B (TNFRSF13B or TACI) is GenBank Accession # AF023614. It is UniProtKB/SwissProt reference # O14836, which gives its intracytoplasmic signaling domain as amino acids 187-293.

Tumor necrosis factor receptor superfamily member 13C (TNFRSF13C or BAFFR) is GenBank Accession # AF373846. It is UniProtKB/SwissProt reference Q96RJ3, which gives its intracytoplasmic signaling domain as amino acids 100-184.

Tumor necrosis factor receptor superfamily member 14 (TNFRST14, HVEM, or LIGHTR) is GenBank Accession # U70321. It is UniProtKB/SwissProt reference # Q92956, which gives its intracytoplasmic signaling domain as amino acids 224-283.

Tumor necrosis factor receptor superfamily member 17 (TNFRSF17 or BCMA) is GenBank Accession # Z29574. It is UniProtKB/SwissProt reference # Q02223, which gives its intracytoplasmic signaling domain as amino acids 78-184.

Tumor necrosis factor receptor superfamily member 18 (TNFRSF18 or GITR) is GenBank Accession # AF125304. It is UniProtKB/SwissProt reference # Q9Y5U5, which gives its intracytoplasmic signaling domain as amino acids 184-241.

Tumor necrosis factor receptor superfamily member 19 (TNFRSF19 or TROY) is GenBank Accession # AB040434. It is UniProtKB/SwissProt reference # Q9NS68, which gives its intracytoplasmic signaling domain as amino acids 192-423.

Tumor necrosis factor receptor superfamily member 21 (TNFRST21 or DR6) is GenBank Accession # AF068868. It is UniProtKB/SwissProt reference # Q9E8U5, which gives its intracytoplasmic signaling domain as amino acids 371-655.

Tumor necrosis factor receptor superfamily member 25 (TNFRSF25 or DR3) is GenBank Accession # U72763. It is UniProtKB/SwissProt reference # Q93038, which gives its intracytoplasmic signaling domain as amino acids 221-417.

Latent membrane protein 1 (LMP1) is not strictly a member of the TNF Receptor SuperFamily. However, we note here that the prototypic RAJI cell LMP1 is GenBank Accession # HS4LMP1. It is UniProtKB/SwissProt reference # P13198, which gives its intracytoplasmic signaling domain as amino acids 187-386.

Multimerizing domains: As described above, the prototypic multimerizing domain for a multimerizing-intracellular signaling cassette is the LMP1 protein of the RAJI strain of the Epstein-Barr Virus (EBV). It is GenBank Accession # HS4LMP1. It is UniProtKB/SwissProt reference # P13198, which gives its N-terminal domain containing 6 transmembrane regions as amino acids 1-186. However, to provide distance from the inner leaflet of the plasma membrane, amino acids 1-190 were used (4 extra amino acids retained).

Design principles of a multimerizing-intracellular signaling cassette: For many members of the TNF Receptor SuperFamily (TNFRSF), clustering in the plane of the cell membrane is required to generate an intracellular signaling event. In order to produce a constitutively activated TNFRSF, it is necessary to mimic this clustering by fusing the intracytoplasmic domain of the TNFRSF with a multimerizing motif. As noted above, the N-terminus of LMP1 is a very suitable multimerizing domain that effectively activates either its own intracytoplasmic (=intracellular) domain (which has activities in common with that of CD40) or the heterologous intracytoplasmic domain of CD40. As described herein, LMP1 is a complete multimerizing-intracellular signaling domain in and of itself. LMP1-CD40 refers to the fusion of RAJI EBV LMP1 amino acids 1-186 in frame with the intracytoplasmic domain of CD40 amino acids 216-277.

As noted above, a spacer or linker can be inserted between the multimerizing domain and the intracellular signaling domain.

By analogy with LMP1-CD40, we predict that the fusion of the LMP1 N-terminus with the intracytoplasmic signaling domains of each and any of the TNFRSFs listed above will yield useful cassettes.

Insertion of a multimerizing-intracellular signaling cassette into HIV-1 and other lentiviruses: a design prototype: As described above, the nef reading frame is ideal for the insertion of or LMP1-CD40. Numerous proviral constructs have been made in which novel coding regions have been inserted into the nef region. Importantly, HIV-1 can replicate if EGFP is placed in the nef-spliced message followed by an IRES directing the translation of NEF protein. This sets a design precedent that is the prototype for the present invention: if a virus or virus vector has a region that can be deleted entirely like nef or has been used to express a heterologous coding sequence (e.g., EGFP or other markers described above), then this site is likely to be suitable for replacement by a multimerizing-intracytoplasmic signaling cassette. Performing this replacement will yield a virus with new properties depending upon the cells infected by the virus and the nature of the intracytoplasmic signaling domain.

Lentiviruses have also been used as the basis for gene therapy. One example is the use of lentiviruses to transduce dendritic cells for use in vaccines. From the description therein, one skilled in the art will know how to insert a multimerizing-intracellular signaling cassette such as LMP1 or LMP1-CD40 in order to improve the strength of this DC-based vaccine strategy.

Insertion of a multimerizing-intracellular signaling cassette into poxviruses: A prototypic poxvirus is Modified Vaccinia Ankara (MVA) which has been chosen as a vaccine to prevent small pox and as a vaccine vector. Other viruses in the poxvirus family that have been promoted for use in humans include vaccinia (dryvax), NYVAC, and avipox (ALVAC). To introduce a multimerizing-intracellular signaling cassette into MVA, tools involving cloning LMP1 into the transfer vector, pLW-44, can be used (Wyatt L S, Shors S T, Murphy B R, Moss B. 1996. Development of a replication-deficient recombinant vaccinia virus vaccine effective against parainfluenza virus 3 infection in an animal model. *Vaccine* 14: 1451-8). This transfer vector is a plasmid that contains green fluorescent protein (GFP) and space for a second gene, here LMP1. Flanking regions homologous to MVA permit recombination of the construct into the del III region of MVA. Recombinant viruses are generated in chicken embryo fibroblasts (CEF) and selected by EGFP fluorescence or immunostaining with anti-EGFP antibody.

Insertion of a multimerizing-intracellular signaling cassette into an oncolytic virus: Viruses that target tumors are being studied for their anti-tumor effects. Typically, these "oncolytic" viruses lead to tumor cell death. One exemplary oncolytic virus is measles virus. For example, use of Edmonston-NSe vaccine strain has been developed, by displaying human IL-13 at the C-terminus of the H protein, and introducing CD46 and signaling lymphocyte activation molecule (SLAM)-ablating mutations in H. The skilled artisan would readily know how to replace the IL-13 coding sequence in this virus with LMP1, LMP1-CD40, or another multimerizing-intracellular signaling cassette. For example, LMP1-Fas, LMP1-TRAIL-R1, LMP1-TRAIT-R2, and LMP1-TNF-R1 are all examples where the cytoplasmic tail of the listed receptors can be multimerized by the LMP1 N-terminal domain. The present invention provides that such engineered viruses will be highly cytolytic for tumor cells and therefore useful for local therapy, e.g., treatment of brain tumors. Likewise, LMP1, LMP1-4-1BB, LMP1-CD27, LMP1-OX40, LMP1-RANK, or LMP1-BAFFR could be similarly introduced into measles virus and used to augment the immune response to tumors. A similar approach could be taken using any of the oncolytic viruses well known in the art.

Various oncolytic viruses have been disclosed in U.S. Pat. Nos. 7,811,582, 7,731,952, 7,638,318, 7,595,042, 7,537,924, 7,459,154, 7,262,033, 7,223,593, 7,122,182, 7,118,755, 7,063,851, 7,063,835, 7,030,099, 6,821,753, 6,719,982, 6,713,067, 6,641,817, 6,544,770, 6,428,968, and 6,316,185; the contents of which are incorporated by reference in their entireties. Additional oncolytic viruses have also been disclosed in U.S. Patent Publication Nos. 2009/0220460, 2007/0264282, 2006/0188480, 2006/0121522, 2005/0249707, 2004/0219167, 2004/0063094, 2004/0022812, and 2003/0219409; the contents of which are incorporated by reference in their entireties. The present invention provides that these oncolytic viruses can be modified to include an expression cassette for expressing the protein of the invention, for example, LPM1 or LMP1-CD40, to stimulate immune responses. The present invention provides that the modified oncolytic viruses can be used in various vaccine compositions.

The present invention provides that DCs can be transfected ex vivo with mRNA encoding LMP1 or LMP1-CD40. These DCs can become activated to be better antigen-presenting cells. These antigen-pulsed DCs in culture can then be administered to a subject, similar to the Dendreon Provenge™ vaccine for prostate cancer.

The present invention also provides the use of plasmids expressing LMP1 (pLMP1) or LMP1-CD40 (pMLP1-CD40) as DNA vaccine adjuvants. Such DNA vaccine can be used, for example, to prevent melanoma metastases.

The present invention also provides the use of multimerizing-intracellular signaling gene cassettes where the signaling portion is not from CD40. For example, some TNF receptor superfamily members (shown in FIG. 29) can be used to mediate growth. A LMP1 version (fusion protein) with any of these TNF receptor superfamily members can be used for various indications, for example would healing and/or regenerative medicine.

Cis- versus Trans-effects of a multimerizing-intracellular signaling cassette: The expression of LMP1 in cells has been shown to induce patched of the cell membrane to bleb off as microvesicles called exosomes. LMP1-induced exosomes can then fuse with nearby cells bringing with them both LMP1 and cellular RNAs (Meckes D G, Jr., Shair K J, Marquitz A R, Kung C P, Edwards R H, Raab-Traub N. 2010. Human tumor virus utilizes exosomes for intercellular communication. *Proc Natl Acad Sci USA* 107: 20370-5). This process is a variation on a phenomenon known as "trogocytosis." Alternative forms of trogocytosis have been reported. By this mechanism, tumor cells transduced or transfected to express LMP1 or the multimerizing-intracellular signaling cassette can produce exosomes that are then taken up by antigen-presenting cells. It is predicted that this will both activate such antigen-presenting cells (e.g., dendritic cells) and cause them to present tumor cell-derived antigens to the immune system. This is called a trans effect because it affects cells other than those in which the multimerizing-intracellular signaling cassette was introduced by transfection or transduction. This allows the introduction of a multimerizing-intracellular signaling cassette to have more widespread effects than those due to just the cells that originally receive the construct (which is said to act in cis in such cells). In particular, a multimerizing-intracellular signaling cassette carried into a tumor cell by an oncolytic virus or microbe is predicted to induce the formation of exosomes that are taken up by DCs and other antigen-presenting cells, leading to a stronger antitumor immune response than would otherwise occur. This in turn wilt increase the therapeutic effectiveness of oncolytic viruses or microbes.

Methods of Gene Transfer: In order to mediate the effect of the transgene expression in a cell, it will be necessary to transfer the expression constructs of the present invention into a cell. Such transfer may employ viral or non-viral methods of gene transfer. This section provides a discussion of methods and compositions of gene transfer.

A transformed cell including an expression vector is generated by introducing into the cell the expression vector. Suitable methods for polynucleotide delivery for transformation of an organelle, a cell, a tissue or an organism for use with the current invention include virtually any method by which a polynucleotide DNA or RNA) can be introduced into an organelle, a cell, a tissue or an organism, as described herein or as would be known to one of ordinary skill in the art.

A host cell can, and has been, used as a recipient for vectors. Host cells may be derived from prokaryotes or eukaryotes, depending upon whether the desired result is replication of the vector or expression of part or all of the vector-encoded polynucleotide sequences. Numerous cell lines and cultures are available for use as a host cell, and they can be obtained through the American Type Culture Collection (ATCC), which is an organization that serves as an archive for living cultures and genetic materials. In specific embodiments, the host cell is a dendritic cell, which is an antigen-presenting cell.

It is well within the knowledge and skill of a skilled artisan to determine an appropriate host. Generally this is based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE™, Competent Cells and SOLOPACK™ Gold Cells (Stratagene, La Jolla, Calif.). Alternatively, bacterial cells such as E. coli LE392 could be used as host cells for phage viruses. Eukaryotic cells that can be used as host cells include, but are not limited to yeast, insects and mammals. Examples of mammalian eukatyotic host cells for replication and/or expression of a vector include, but are not limited to, HeLa, NIH3T3, Jurkat, 293, COS, CHO, Saos, and PC12. Examples of yeast strains include, but are not limited to, YPH499, YPH500 and YPH501.

Non-Viral Transfer—Ex Vivo Transformation: Methods for transfecting cells and tissues removed from an organism in an ex vivo setting are known to those of skill in the art. For example, canine endothelial cells have been genetically altered by retroviral gene transfer in vitro and transplanted into a canine. In another example, Yucatan minipig endothelial cells were transfected by retrovirus in vitro and transplanted into an artery using a double-balloon catheter. Thus, it is contemplated that cells or tissues may be removed and transfected ex vivo using the polynucleotides of the present invention. In particular aspects, the transplanted cells or tissues may be placed into an organism. Thus, it is well within the knowledge of one skilled in the art to isolate dendritic cells from an animal, transfect the cells with the expression vector and then administer the transfected or transformed cells back to the animal.

Injection: In certain embodiments, a polynucleotide may be delivered to an organelle, a cell, a tissue or an organism via one or more injections (i.e., a needle injection), such as, for example, subcutaneously, intradermally, intramuscularly, intravenously, intraperitoneally, etc. Methods of injection of vaccines are well known to those of ordinary skill in the art (e.g., injection of a composition comprising a saline solution). Further embodiments of the present invention include the introduction of a polynucleotide by direct microinjection. The amount of the expression vector used may vary upon the nature of the antigen as well as the organelle, cell, tissue or organism used.

Intradermal, intranodal, or intralymphatic injections are some of the more commonly used methods of DC administration. Intradermal injection is characterized by a low rate of absorption into the bloodstream but rapid uptake into the lymphatic system. The presence of large numbers of Langerhans dendritic cells in the dermis will transport intact as well as processed antigen to draining lymph nodes. Proper site preparation is necessary to perform this correctly (i.e., hair must be clipped in order to observe proper needle placement). Intranodal injection allows for direct delivery of antigen to lymphoid tissues. Intralymphatic injection allows direct administration of DCs.

Electroporation: In certain embodiments of the present invention, a polynucleotide is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes are employed to render the target recipient cells more susceptible to transformation by electroporation than untreated cells (U.S. Pat. No. 5,384,253, incorporated herein by reference).

Transfection of eukaryotic cells using electroporation has been quite successful. Mouse pre-B lymphocytes have been transfected with human kappa-immunoglobulin genes, and rat hepatocytes have been transfected with the chloramphenicol acetyltransferase gene.

Calcium Phosphate: In other embodiments of the present invention, a polynucleotide is introduced to the cells using calcium phosphate precipitation. Human K B cells have been transfected with adenovirus 5 DNA. Also in this manner, mouse L(A9), mouse C127, CHO, CV-1, BHK, NIH3T3 and HeLa cells were transfected with a neomycin marker gene, and rat hepatocytes were transfected with a variety of marker genes.

DEAE-Dextran: In another embodiment, a polynucleotide is delivered into a cell using DEAE-dextran followed by polyethylene glycol. In this manner, reporter plasmids were introduced into mouse myeloma and erythroleukemia cells.

Sonication Loading: Additional embodiments of the present invention include the introduction of a polynucleotide by direct sonic loading. LTK-fibroblasts have been transfected with the thymidine kinase gene by sonication loading.

Liposome-Mediated Transfection: In a further embodiment of the invention, a polynucleotide may be entrapped in a lipid complex, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. Also contemplated is a polynucleotide complexed with Lipofectamine (Gibco BRL) or Superfect (Qiagen).

Receptor Mediated Transfection: Still further, a polynucleotide may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles include a cell receptor-specific ligand and a polynucleotide-binding agent. Another embodiment includes a cell receptor-specific ligand to which the polynucleotide to be delivered has been operatively attached. Several ligands have been used for receptor-mediated gene transfer (EP 0273085), which establishes the operability of the technique. Specific delivery in the context of another mammalian cell type has been described. In certain aspects of the present invention, a ligand is chosen to correspond to a receptor specifically expressed on the target cell population.

In other embodiments, a polynucleotide delivery vehicle component of a cell-specific polynucleotide-targeting vehicle may include a specific binding ligand in combination with a liposome. The polynucleotide(s) to be delivered can be housed within the liposome and the specific binding ligand can be functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a polynucleotide to cells that exhibit upregulation of the EGF receptor.

In still further embodiments, the polynucleotide delivery vehicle component of a targeted delivery vehicle may be a liposome itself, which can include one or more lipids or glycoproteins that direct cell-specific binding. For example, lactosyl-ceramide, a galactose-terminal asialoganglioside, have been incorporated into liposomes and observed an increase in the uptake of the insulin gene by hepatocytes. The present invention provides that the tissue-specific transforming constructs of the present invention can be specifically delivered into a target cell in a similar manner.

Microprojectile Bombardment: Microprojectile bombardment techniques can be used to introduce a polynucleotide into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA-coated microprojectiles to a high velocity allowing them to pierce cell membranes and enter cells without killing them. There are a wide variety of microprojectile bombardment techniques known in the art, many of which are applicable to the invention.

In this microprojectile bombardment, one or more particles may be coated with at least one polynucleotide and delivered into cells by a propelling force. Several devices for accelerating small particles have been developed. One such device relies on a high voltage discharge to generate an electrical current, which in turn provides the motive force. The microprojectiles used have consisted of biologically inert substances for example tungsten or gold particles or beads. Exemplary particles include those comprised of tungsten, platinum, and preferably, gold. The present invention provides that in some embodiments DNA precipitation onto metal particles would not be necessary for DNA delivery to a recipient cell using microprojectile bombardment. However, the present invention provides that particles may contain DNA rather than be coated with DNA. DNA-coated particles may increase the level of DNA delivery via particle bombardment but are not, in and of themselves, necessary.

Viral Vector-Mediated Transfer: In certain embodiments, transgene is incorporated into a viral particle to mediate gene transfer to a cell. Typically, the virus simply will be exposed to the appropriate host cell under physiologic conditions, permitting uptake of the virus. The present methods can be advantageously employed using a variety of viral vectors.

Adenovirus: Adenovirus is particularly suitable for use as a gene transfer vector because of its mid-sized DNA genome, ease of manipulation, high titer, wide target-cell range, and high infectivity. The roughly 36 kb viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off. The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence, which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with-relative ease.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus. Therefore, inclusion of these elements in an adenoviral vector can permit replication.

In addition, the packaging signal for viral encapsulation is localized between 194-385 bp (0.5-1.1 map units) at the left end of the viral genome. This signal mimics the protein recognition site in bacteriophage lamda DNA where a specific sequence dose to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells.

It has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map. Later studies showed that a mutant with a deletion in the E1A (194-358 bp) region of the genome grew poorly even in a cell line that complemented the early (E1A) function. When a compensating adenoviral DNA (0-353 bp) was recombined into the right end of the mutant, the virus was packaged normally. Further mutational analysis identified a short, repeated, position-dependent element in the left end of the adenovirus type 5 (Ad5) genome. One copy of the repeat was found to be sufficient for efficient packaging if present at either end of the genome, but not when moved towards the interior of the Ad5 DNA molecule.

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals is packaged selectively when compared to the helpers. If the preference is great enough, stocks approaching homogeneity can be achieved.

Retrovirus: The retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains at least three genes—gag, pot and env—that code for capsid proteins, polymerase enzyme, and envelope components, respectively. A sequence found upstream from the gag gene, termed PSI (Ψ), functions as a signal for packaging of the genome into virions. Two long terminal repeat (LTR) sequences are present at the 5' and 3' ends of the viral genome. These contain strong promoter and enhancer sequences and also are required for integration in the host cell genome.

In order to construct a retroviral vector, a nucleic acid encoding a promoter is inserted into the viral genome in the place of certain viral sequences to produce a virus that is replication-defective. In order to produce virions, a packaging cell line containing the gag, pot and env genes but without the LTR and PSI (Ψ) components is constructed. When a recombinant plasmid containing a human cDNA, together with the retroviral and PSI (Ψ) sequences is introduced into this cell line (by calcium phosphate precipitation for example), the PSI (Ψ) sequence allows the RNA transcript of the recombinant plasmid to be packaged into viral particles, which are then secreted into the culture media. The media containing the recombinant retroviruses is collected, optionally concentrated, and used for gene transfer. Retroviral vectors are able to infect a broad variety of cell types. However, integration and stable expression of many types of retroviruses require the division of host cells.

An approach designed to allow specific targeting of retrovirus vectors has been developed based on the chemical modification of a retrovirus by the chemical addition of galactose residues to the viral envelope. This modification can permit the specific infection of cells such as hepatocytes via asialoglycoprotein receptors.

A different approach to targeting of recombinant retroviruses was designed in which biotinylated antibodies against a retroviral envelope protein and against a specific cell receptor were used. The antibodies can be coupled via the biotin components by using streptavidin. Using antibodies against major histocompatibility complex class I and class II antigens, the infection of a variety of human cells that bore those surface antigens has been demonstrated with an ecotropic virus in vitro.

Adeno-Associated Virus (AAV) utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The most well-characterized helpers can be adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome, or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo.

AAV-mediated efficient gene transfer and expression in the lung has led to clinical trials for the treatment of cystic fibrosis. Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient.

Other Viral Vectors: Other viral vectors are employed as expression constructs in the present invention. Vectors derived from viruses such as vaccinia virus canary pox virus, and herpes viruses are employed. These viruses offer several features for use in gene transfer into various mammalian cells.

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

Formulations and Routes for Administration to Patients: Where clinical applications are contemplated, it will be necessary to prepare pharmaceutical compositions-expression constructs, expression vectors, fused proteins, transduced or transfected activated DCs, transduced or transfected and loaded DCs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention include an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. A pharmaceutically acceptable carrier includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For oral administration, the compositions of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, Remington's Pharmaceutical Sciences 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by FDA Office of Biologics standards.

Methods for Treating a Disease: The present invention also encompasses methods of treatment or prevention of a disease caused by pathogenic microorganisms and/or a hyperproliferative disease.

Diseases may be treated or prevented by use of the present invention include diseases caused by viruses, bacteria, yeast, parasites, protozoa, cancer cells and the like. The pharmaceutical composition of the present invention (transduced or transfected DCs, expression vector, expression construct, etc.) of the present invention may be used as a generalized immune enhancer (DC activating composition or system) and as such has utility in treating diseases. Exemplary diseases that can be treated and/or prevented utilizing the pharmaceutical composition of the present invention include, hut are not limited to infections of viral etiology such as HIV, influenza, Herpes, viral hepatitis, Epstein Barr, polio, viral encephalitis, measles, chicken pox, Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

Preneoplastic or hyperplastic states which may be treated or prevented using pharmaceutical composition of the present invention (transduced or transfected DCs, expression vector, expression construct, etc.) of the present invention include but are not limited to preneoplastic or hyperplastic states such as colon polyps, Crohn's disease, ulcerative colitis, breast lesions and the like.

Cancers which may be treated using the pharmaceutical composition of the present invention of the present invention include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

Other hyperproliferative diseases that may be treated using DC activation system of the present invention include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

In the method of treatment, the administration of the pharmaceutical composition (expression construct, expression vector, fused protein, transduced or transfected activated DCs, transduced or transfected and loaded DCs) of the invention may be for either "prophylactic" or "therapeutic" purpose. When provided prophylactically, the pharmaceutical composition of the present invention is provided in advance of any symptom. The prophylactic administration of pharmaceutical composition serves to prevent or ameliorate any subsequent infection or disease. When provided therapeutically, the pharmaceutical composition is provided at or after the onset of a symptom of infection or disease. Thus the present invention may be provided either prior to the anticipated exposure to a disease-causing agent or disease state or after the initiation of the infection or disease.

The term "unit dose" as it pertains to the inoculum refers to physically discrete units suitable as unitary dosages for mammals, each unit containing a predetermined quantity of pharmaceutical composition calculated to produce the desired immunogenic effect in association with the required diluent. The specifications for the novel unit dose of an inoculum of this invention are dictated by and are dependent upon the unique characteristics of the pharmaceutical composition and the particular immunologic effect to be achieved.

An effective amount of the pharmaceutical composition would be the amount that achieves this selected result of enhancing the immune response, and such an amount could be determined as a matter of routine by a person skilled in the art. For example, an effective amount of for treating an immune system deficiency could be that amount necessary to cause activation of the immune system, resulting in the development of an antigen specific immune response upon exposure to antigen. The term is also synonymous with "sufficient amount."

The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

Genetic Based Therapies: Specifically, the present inventors intend to provide, to a cell, an expression construct capable of providing a co-stimulatory polypeptide, such as LMP1 LMP1-CD40 to the cell, such as an antigen-presenting cell. The lengthy discussion of expression vectors and the genetic elements employed therein is incorporated into this section by reference. Particularly preferred expression vectors are viral vectors such as adenovirus, adeno-associated virus, herpes virus, vaccinia virus and retrovirus. Also preferred is lysosomal-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1\times10^4$, $1\times10^5$, $1\times10^6$, $1\times10^7$, $1\times10^8$, $1\times10^9$, $1\times10^{10}$, $1\times10^{11}$ or $1\times10^{12}$ infectious particles to the patient. Similar figures may be extrapolated for liposomal or other non-viral formulations by comparing relative uptake efficiencies. Formulation as a pharmaceutically acceptable composition is discussed below.

Cell Based Therapy: Another therapy that is contemplated is the administration of transduced or transfected antigen-presenting cells. The antigen-presenting cells may be transduced or transfected in vitro. Formulation as a pharmaceutically acceptable composition is discussed above.

In cell based therapies, the transduced or transfected antigen-presenting cells may be transduced or transfected with target antigen nucleic acids, such as mRNA or DNA or proteins; pulsed with cell lysates, proteins or nucleic acids; or electrofused with cells. The cells, proteins, cell lysates, or nucleic acid may derive from cells, such as tumor cells or other pathogenic microorganism, for example, viruses, bacteria, protozoa, etc.

Combination Therapies: In order to increase the effectiveness of the expression vector of the present invention, it may be desirable to combine these compositions and methods of the invention with an agent effective in the treatment of the disease.

In certain embodiments, anti-cancer agents may be used in combination with the present invention. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor or one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

In further embodiments antibiotics can be used in combination with the pharmaceutical composition of the present invention to treat and/or prevent an infectious disease. Such antibiotics include, but are not limited to, amikacin, aminoglycosides e.g., gentamycin), amoxicillin, amphotericin B, ampicillin, antimonials, atovaquone sodium stibogluconate, azithromycin, capreomycin, cefotaxime, cefoxitin, ceftriaxone, chloramphenicol, clarithromycin, clindamycin, clofazimine, cycloserine, dapsone, doxycycline, ethambutol, ethionamide, fluconazole, fluoroquinolones, isoniazid, itraconazole, kanamycin, ketoconazole, minocycline, ofloxacin), para-aminosalicylic acid, pentamidine, polymixin definsins, prothionamide, pyrazinamide, pyrimethamine sulfadiazine, quinolones ciprofloxacin), rifabutin, rifampin, sparfloxacin, streptomycin, sulfonamides, tetracyclines, thiacetazone, trimethaprim-sulfamethoxazole, viomycin or combinations thereof.

More generally, such an agent would be provided in a combined amount with the expression vector effective to kill or inhibit proliferation of a cancer cell and/or microorganism. This process may involve contacting the cell(s) with an agent(s) and the pharmaceutical composition of the present invention at the same time or within a period of time wherein separate administration of the pharmaceutical composition of the present invention and an agent to a cell, tissue or organism produces a desired therapeutic benefit. This may be achieved by contacting the cell, tissue or organism with a single composition or pharmacological formulation that includes both the pharmaceutical composition of the present invention and one or more agents, or by contacting the cell with two or more distinct compositions or formulations, wherein one composition includes the pharmaceutical composition of the present invention and the other includes one or more agents.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing.

The administration of the pharmaceutical composition may precede, be co-current with and/or follow the other agent(s) by intervals ranging from minutes to weeks. In embodiments where the pharmaceutical composition of the present invention, and other agent(s) are applied separately to a cell, tissue or organism, one would generally ensure that a significant period of time did not expire between the times of each delivery, such that the pharmaceutical composition of the present invention and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) as the pharmaceutical composition of the present invention. In other aspects, one or more agents may be administered within of from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition of the present invention and one or more agents may be employed.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Construction of a Replicating HIV-1 Virus Expressing LMP1 or LMP1-CD40

Using recombinant DNA techniques, the coding sequence of LMP1 (1,161 bp encoding 387 amino acids, shown schematically in FIG. 1) is cloned into the pNL4-3/BaL construct. The resulting plasmid clone is shown schematically in FIG. 2 and is named "NL4-3-BAL-LMP1-IRES" (SEQ ID NO: 1). Similarly, LMP1-CD40 (shown schematically in FIG. 1) is cloned into pNL4-3/BaL to create the plasmid shown schematically in FIG. 2 and named "NL4-3-BAL-LMP1-CD40-IRES" (SEQ ID NO: 2). This construct contains the N-terminus of Raji EBV LMP1 (amino acids 1-190) fused in frame with the C-terminus from human CD40 (amino acids 220-277). The sequence of LMP1 is provided in SEQ ID NO: 11 and the cytoplasmic fragment or portion of human CD44 is provided in SEQ ID NO: 12.

Following plasmid purification and confirmation by sequencing, the plasmids are used to create live virus by transfecting them into 293T cells using lipofectamine. 48 hours later, the supernatants are collected, aliquoted, and stored frozen at −80° C. until use. Infectious titers are determined using a CD4/LTR-beta-galactosidase HeLa indicator cell line.

Example 2

Macrophages Infected by LMP1- and LMP1-CD40-expressing HIV-1 are Stimulated to Make Cytokines Human blood monocytes are isolated using anti-CD14 immunomagnetic beads (Miltenyi Biotech) and cultured in 48-well plates for 10 days in RPMI1640 supplemented with 10% autologous serum and 2 mM L-glutamine. At the end of this period, the non-adherent cells are removed by washing and HIV-1 is added to each well for 4 hours. Following 5 washes with media, the cultures are incubated for an additional 8 days, following which the supernatants are assayed for cytokines by enzyme-linked immunosorbent assay (ELISA) (R&D Systems) and viral p24 Gag ELISA (Coulter).

As shown in FIG. 3, LMP-expressing HIV-1 strongly stimulates the production of MIP-1β and IL-8 by macrophages. LMP-CD40-expressing HIV-1 does not stimulate MIP-1beta production but does stimulate a small amount of IL-8 production, as shown in FIG. 3. Both viruses replicate less well than unmodified NL4-3/BaL, as judged by the release of p24 Gag antigen.

Example 3

Macrophages Infected by LMP1- and LMP1-CD40-Expressing Virus Release Higher Levels of Immunostimulatory Cytokines but Did not Produce Higher Levels of Immunosuppressive IL-10

Figure 4:
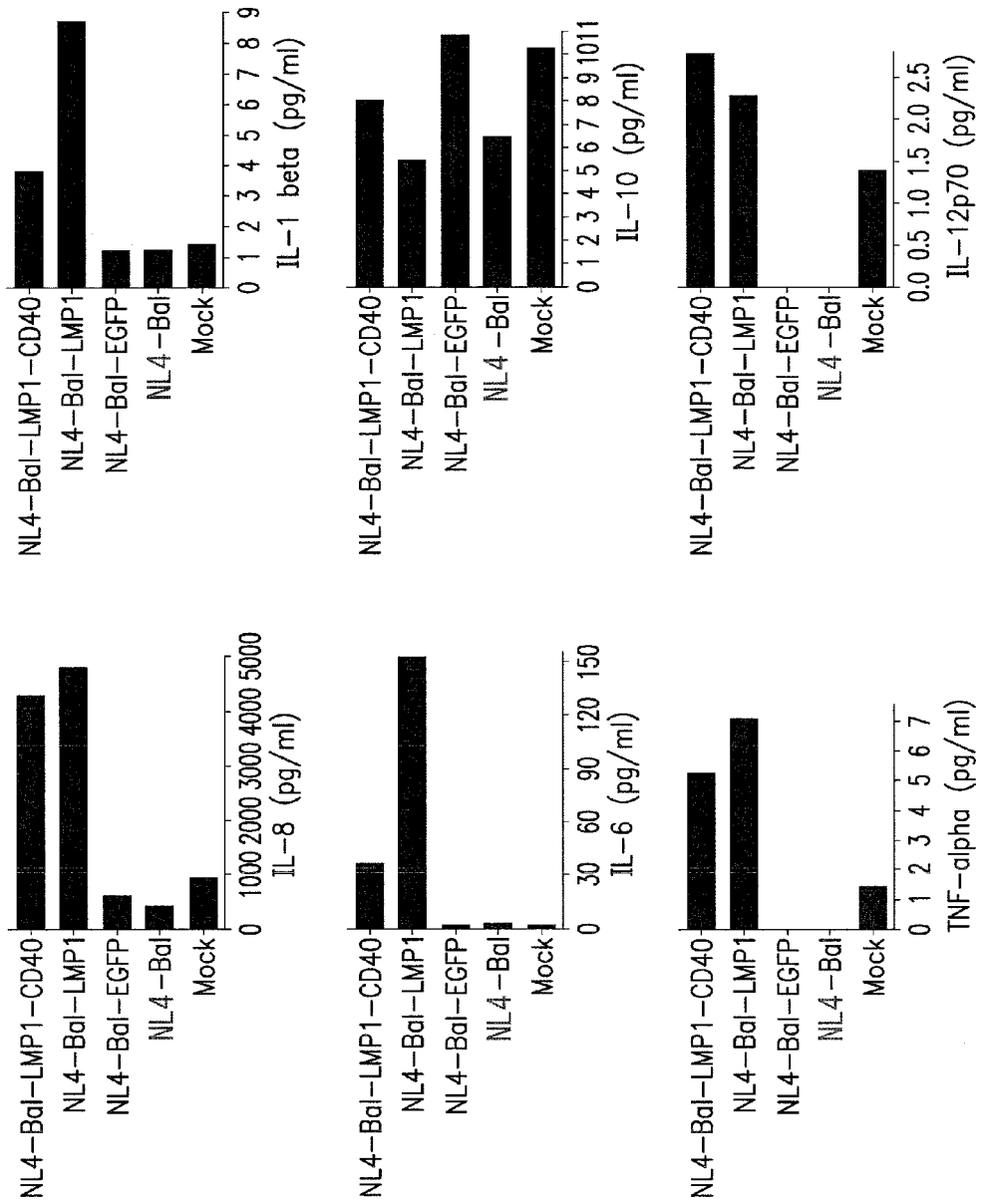

In an experiment similar to Example 2, infected macrophages are cultured for 9 days after infection before having their supernatants assayed for IL-8, IL-1β, IL-6, IL-12p70, and TNFα. As shown in FIG. 4, the LMP-1-expressing HIV-1 strongly stimulates the production of all of these immunostimulatory cytokines. Importantly, however, there is no increase in the production of the immunosuppressive cytokine, IL-10. Macrophage infection by LMP1-CD40-expressing HIV-1 leads to a similar profile of cytokine production. These results are gratifying because they show for the first time that LMP1 and LMP1-CD40 have effects on macrophages. Overall, these data indicate that the LMP1 and LMP1-CD40 multimerizing-cytoplasmic signaling cassettes promote immunostimulation rather than immunosuppression.

Example 4

Dendritic Cells are Also Stimulated by Infection with LMP1- and LMP1-CD40-Expressing Monocyte-derived dendritic cells (DCs) are prepared from CD14+ monocytes by culture in GM-CSF and IL-4 containing media for 6 days. Then the DCs are exposed to virus. As shown in FIG. 5, LMP1-expressing stimulates DCs to produce IL-8, IL-1β, TNFα, and IL-6. In contrast, LMP1-CD40-expressing only stimulates DCs to produce IL-8. These results are gratifying because they show for the first time that LMP1 and LMP1-CD40 have effects on DCs. Furthermore, these data show that HIV-1 can be engineered to express these multimerizing-cytoplasmic signaling cassettes in a functional manner.

Example 5

Dendritic Cells Produce a Range of Cytokines Following Infection by LMP1- and LMP1-CD40-Expressing HIV-1

Monocyte-derived dendritic cells (DCs) are exposed to viruses similarly to Example 4. As a positive control, a cytokine mix MIMIC™ (Clontech, Palo Alto, Calif.) is used. The MIMIC™ used includes a DC maturation cocktail composed of IL-1β+IL-6+TNF-α+PGE$_2$. As shown in FIG. 6, assays of supernatants by ELISA (R&D Systems) 4 days after infection showed that LMP1-expressing HIV-1 stimulates DCs almost as well as the MIMIC™ used with respect to IL-8, IL-1β, IL-6, and TNFα production. Surprisingly, LMP1-expressing HIV-1 stimulated DCs to make IL-12p70 bioactive heterodimer, which even the MIMIC™ used is unable to stimulate. Importantly, whereas the MIMIC™ used also stimulates the production of IL-10, an immunosuppressive cytokine, IL-10 production is not increased by LMP1-expressing HIV-1 infection. This indicates that LMP1-expressing HIV-1 is a better DC stimulus than the MIMIC™ used, the standard for DC stimulation in vitro. Note that LMP1-CD40-expressing HIV-1 is less active in this regard.

Example 6

LMP1-CD40-Expressing HIV-1 Stimulates the Antigen-Presenting Ability of Human DCs The mixed leukocyte reaction (MLR) is a classic test of alloantigen presentation. By measuring the expression of ki67, a cell cycle marker, in CD4+ and CD8+ T cells, LMP1-CD40-expressing HIV-1 is found to stimulate DCs to increase both CD4+ and CD8+ responses (see FIG. 7). This indicates that LMP1-CD40-expressing HIV-1 is an immunostimulatory virus that promotes immune responses by T cells.

Example 7

Dendritic Cells can Also be Stimulated by a Single-Cycle SIV (scSIV) Expressing LMP1 or LMP1-CD40

In preparation for a trial in rhesus macaques, the LMP1 and LMP1-CD40 cassettes are cloned into Simian immunodeficiency virus (SIV). For added safety, the SIV used contained mutations in the protease and integrase genes (see FIG. 8), which prevents the production of progeny virus. This single-cycle SIV (scSIV) is still surprisingly stimulatory for human DCs when it included a LMP1 or LMP1-CD40 expression cassette (see FIG. 9). This type of single-cycle virus serves as the prototype for a new kind of Human immunodeficiency virus (HIV) vaccine. Similar replication-defective viruses can be constructed in many viral systems leading a new series of live, attenuated, but highly immunostimulatory viral vaccines.

Example 8

LMP1-Expressing Single-Cycle SIV is a Self-Adjuvanting Virus for Anti-SIV Immune Responses The present invention provides that single-cycle SIV (scSIV) can carry its own antigens into immune responses and a multimerizing-intracellular signaling cassette can act as an adjuvant for enhancing immune responses. Human monocyte-derived dendritic cells (PCs) are studied in vitro, where the DCs are exposed to the scSIV viruses for 4 days, and then co-cultured with human T cells for another 12 days. After the co-culture period, the cells are transferred to the wells of an Enzyme Linked immuno-Spot (ELISPOT) plate and stimulated with a pool of SIV Gag 15-mer peptides. This assay provides a rigorous evaluation of antigen-presenting function and T cell responses, given that the T cells are naïve for Gag antigen on day 0. Thus, scSIV-LMP1 induces a significant increase in Gag-specific interferon gamma responsive T cells ($p<0.01$ comparing scSIV-LMP1 to scSIV-EGFP). These data and similar results with HIV-LMP1 demonstrate that scSIV-LMP1 is immunostimulatory and effectively self-adjuvanting by the inclusion of the LMP1 multimerizing-intracytoplasmic signaling cassette. This surprising result is the prototype for a range of viruses, vectors, and tumor cells where the inclusion of a multimerizing-intracytoplasmic signaling cassette can be used to induce a strong immune response to the antigens that are co-extensive in space and time—i.e. self-adjuvanting microbial and/or tumor vaccines.

Example 9

LMP1 and LMP1-CD40 can Also be Introduced into Modified Vaccinia Ankara (MVA)

MVA is a widely studied viral vector. As shown in FIG. 11, LMP1 is cloned into the pLW-44 transfer plasmid under the control of the mH5 promoter. The P11 promoter drives the expression of GFP. The sequence of pLW-44 LMP1 is provided in SEQ ID NO: 13 and the sequence of pLW-44 LMP1_CD44 is provided in SEQ ID NO: 14.

Chicken embryo fibroblasts (CEF) are infected with wild-type MVA at an MOI of 0.05 (1 well of a 6 well plate). Then, 1 and half hours later, each well is transfected with 2 μg of transfer plasmid using 10 μl of Lipofectamine 2000 (Gibco) in Optimem (Gibco) per manufacturer's instructions, and incubated at room temperature for 20 minutes.

The cultures are incubated for three days using two media changes and finally the infected cells are collected by scraping and freeze-thawed to release viruses. To identify the recombinant viruses, the stock is diluted and used to infect fresh CEF cells which are covered with a methylcellulose overlay, and GFP-containing plaques are identified using a fluorescent microscope.

The recombinant viruses are plaque purified 3 times, and then expanded by growth in CEF bulk cultures. Polymerase chain reaction (PCR) confirms that LMP1 and LMP1-CD40 have been successfully introduced into the replicating viruses. However, MVA containing LMP1-CD40 grows poorly and is unstable, perhaps reflecting an activity of this construct on CEF cells that antagonizes the growth of MVA.

FIG. 28 shows enhanced dendritic cell (DC) maturation by Modified Vaccinia Ankara (MVA) virus containing LMP1 or LMP1-CD40 adjuvant gene cassette.

Overall, this example illustrates that the LMP1 and LMP1-CD40 cassettes can be successfully transferred to a wide range of viruses and microbes, or inserted into viral vectors. This makes these adjuvant-like sequences valuable as a means of enhancing the immunogenicity of these agents.

Example 10

Construction of LMP1 and LMP-1CD40 Adjuvant Gene Cassettes

LMP1, a constitutively active analog of CD40, is herein provided to function as a molecular activator of dendritic cells and macrophages that can be used as a powerful vaccine adjuvant.

HIV-1 does not significantly activate cellular immunity, which has made it difficult to use attenuated forms of HIV-1 as a vaccine. In contrast, Epstein-Barr Virus (EBV) induces robust T cell responses in most infected individuals, perhaps because this virus contains Latent Membrane Protein-1 (LMP1), a viral mimic of CD40 which is a key activating molecule for dendritic cells (DCs) and macrophages. Consequently, studies have been conducted using LMP1 and LMP1-CD40, a related construct formed by replacing the intracellular signaling domain of LMP1 with that of CD40. Upon electroporation into DCs, LMP1 and LMP1-CD40 mRNAs are sufficient to upregulate costimulatory molecules and proinflammatory cytokines, indicating that these molecules can function in isolation as adjuvant-like molecules. As a first step toward an improved HIV vaccine, LMP1 and LMP1-CD40 are introduced into an HIV-1 construct to produce virions encoding these proteins. Transduction of DCs and macrophages with these viruses induced morphological changes and upregulated costimulatory molecules and cytokine production by these cells. HIV-LMP1 enhances the antigen-presenting function of DCs as measured in an in vitro immunization assay. The present invention provides that LMP1 and LMP1-CD40 are portable gene cassettes with strong adjuvant properties that can be introduced into viruses like HIV that by themselves are insufficient to induce protective cellular immunity.

Since Jenner's original description of vaccinia, an attenuated form of the smallpox virus, there has been continued interest in using viruses as vaccines. However, whereas viral vaccines like yellow fever 17D induce strong protective immunity; viral vaccines for other viruses like RSV do not. This difference has been explained by the presence or absence of virus-encoded immunostimulators: yellow fever 17D strongly activates toll-like receptors (TLRs) whereas RSV fails to do so. These examples suggest that viral vaccines are more likely to be effective if they carry within them their own adjuvant-like immunostimulatory molecules.

In this regard, it is notable that HIV-1 is largely deficient in direct immunostimulatory qualities. HIV-1 infection of cultured myeloid dendritic cells DCs), for example, does not induce DC immunostimulatory functions. Instead, HIV-exposed DCs require exogenous stimuli like CD40 ligand (CD40L) to become activated. CD40L is normally expressed by activated CD4+ T cells and provides DCs with the strong CD40 stimulation needed to generate effective CD8+ cell responses.

Given the importance of including immune-activating molecules in viral vaccines, it has been demonstrated the existence of strong CD8+ T cell immunity engendered by infection with Epstein-Barr virus (EBV), a gamma herpesvirus (HHV4). EBV infection is very common and is often manifested clinically as infectious mononucleosis (AIM), a generally self-limiting disease. Notably, AIM is characterized by an explosion of CD8+ T cells that recognize EBV antigens. These anti-EBV CD8+ T cells contribute to the resolution of EBV viremia and persist as memory cells at remarkably high levels for years. For example, in healthy EBV-seropositive subjects, up to 5.5% of circulating CD8+ cells are identified as EBV-reactive using tetramers for just a single peptide epitope. While it has not been fully determined why EBV is so immunostimulatory vivo, the functional similarity of the EBV latent membrane protein-1 (LMP1) to the CD40 receptor has been demonstrated. Indeed, LMP1 has been viewed as a constitutively activated viral mimic of the CD40 receptor. The present invention provides that LMP1 and a related protein, LMP1-CD40, can be used as molecular adjuvants for DCs and macrophages. The present invention further provides that both LMP1 and LMP1-CD40 strongly activated these antigen-presenting cells (APCs). This function is maintained when these molecules are inserted into the HIV-1 genome and the resulting viruses are strongly activating for APCs in vitro. Consequently, the present invention provides that LMP1 and LMP1-CD40 can serve as portable gene cassettes with adjuvant-like qualities that can be used to improve the cellular immune response to viral vaccines.

Cells and reagents: Venous blood is obtained from Continental Blood Services, Inc. (Miami, Fla.) as anonymous fluffy Coat donations from HIV-seronegative donors. Peripheral blood mononuclear cells (PBMCs) are isolated by centrifugation over Ficoll-hypaque and subsequently cultured in RPMI 1640 (Thermo Scientific HyClone, Logan, Utah) supplemented with 5% human AB serum (Lonza, Allendale, N.J.) and 10 mM HEPES (Invitrogen, Carlsbad, Calif.) (complete RPMI 1640), 293T HEK cells are cultured in Dulbecco's modified Eagle medium (DMEM) supplemented with 10% fetal bovine serum (FBS), 2 mM L-glutamine, and antibiotics (100 U/ml penicillin and 100 μg/ml streptomycin). TZM-bl cells are Obtained through the National Institutes of Health AIDS Research and Reference Reagent Program (catalogue no. 8129, contributed by John C. Kappes and Xiaoyun Wu), cultured in RPMI 1640 medium (supplemented with 10% FBS, 2 mM L-glutamine, and antibiotics), and used to quantify infectious HIV virions.

Plasmid DNAs: Plasmid DNA encoding enhanced green fluorescent protein (EGFP) is obtained from Dr. Chelsa Spina. pNL-BaL (termed pHIV in the figure legends) is a macrophage-tropic proviral clone of pNL4-3 containing the CCR5-utilizing envelope from HIV-1BaL. Plasmids are grown in *E. coli* DH 5α and isolated using a Plasmid Maxi Kit (QIAGEN, Valencia, Calif.). To reduce the presence of exogenous stimulating materials, the plasmids are further cleaned using Triton X-114 extraction.

Construction of LMP1 and LMP1-CD40 adjuvant gene cassettes: cDNA is prepared from Raji B cells (American Type Culture Collection, Manassas, Va.) and the LMP1 sequence of EBV is isolated by polymerase chain reaction (PCR) and found to be identical to the reference sequence (GenBank M58153.1). Related to LMP1 is an artificial fusion protein containing the multimerizing, membrane-associated N-terminus of LMP1 conjoined with the intracytoplasmic domain of CD40, i.e., LMP1-CD40. This membrane-associated intracellular fusion protein mimics the constitutive signaling of CD40 without the need for an external ligand. LMP1-CD40 is constructed by fusing DNA encoding the N-terminal 190 amino acids of LMP1 (beginning with the ATG start codon) with the C-terminal 58 amino acids of CD40 followed by a TGA translational stop codon. For the preparation of and LMP1-CD40 mRNA described below, these sequences are cloned into the pGEM-4Z/A64 vector.

Preparation of HIV-1 virions expressing LMP1 or LMP1-CD40: Levy et al. (2004) Proc Acad Sci USA 101: 4204-9, has described the design of replication competent HIV-1 pro-viral clones in which exogenous coding sequences such as EGFP can be inserted just 5-prime to nef, followed by an internal ribosome entry site (IRES) that allows continued translation of the natural Nef protein (FIG. 2). Starting with the macrophage-tropic pNL-BaL proviral clone, overlap PCR was used to construct plasmids expressing either EGFP (pHIV-EGFP), LMP1 (pHIV-LMP1) LMP1-CD40 (pHIV-LMP1-CD40). The present invention provides that these exogenous genes are expressed in fief-spliced mRNAs where the nef-spliced mRNAs are very strongly expressed and are the predominant mRNA species in macrophages during the first 24 hours following HIV-1 infection. This design maximizes the expression of these exogenous genes, whereas other provirus designs would be expected to result in more modest expression of these transgenes.

Example 11

Preparation of DCs and Macrophages and Virus Transduction

To isolate monocytes from PBMCs, cells are first adhered to T175 plastic flasks (Corning-Costar, Cambridge, Mass.) for 24 hours in RPMI 1640 containing 10% heat-inactivated human AB serum. Following washing to remove non-adherent cells, the adherent monocytes are harvested by gentle scraping and transferred into 24-well at a density of $1\times10^6$ cells/well. To allow differentiation into monocyte-derived macrophages (macrophages), the cultures are incubated for an additional 7 days. To prepare monocyte-derived dendritic cells (DCs), the monocytes are cultured in 800 U/ml GM-CSF and 500 U/ml IL-4 (R & D Systems, Inc., Minneapolis, Minn.) for 5 days, adding fresh Granulocyte macrophage colony-stimulating factor (GM-CSF) and IL-4 on day 3.

Lentiviral transduction of DCs and macrophages and flow cytometry: Infections are initiated by aspirating the supernatant media from the wells containing $10^6$ DCs or macrophages and then adding 100 μl/well of media containing 100 ng p24 equivalents of HIV (calculated to be a multiplicity of infection of 0.1) followed by culture at 37° C. for 4 hours. Next the cells are washed twice with RPMI medium and then fed with 2 ml of complete RPMI 1640 followed by incubation at 37° C. for up to 8 days. The culture supernatants of transduced DCs or macrophages are collected at different time points and stored at −80° C. For flow cytometry, macrophages are stained on the plates and then harvested by scraping, white DCs are first harvested by gentle scraping and then re-suspended for staining. Cells are washed in fluorescence-activated cell sorter buffer (PBS supplemented with 3% fetal calf serum and 0.02% sodium azide) and then stained by fluorochrome-conjugated antibodies. Flow cytometry is performed using a LSRII bioanalyzer (Becton Dickinson) and analyzed with the FlowJo software program (Tree Star, San Carlos, Calif.).

Measurement of DC and macrophage activation by cytokine assays and RT-PCR for chemokine mRNA: For cytokine measurements, supernatants are collected from DC and macrophage cultures either 48 hours after mRNA electroporation or 7 days after virus infection and stored at −80° C. until assay. Concentrations of IL-8, IL-6, IL-1β, IL-10 and IL-12p70 are measured by cytometric bead array (CBA) (BD Biosciences, San Jose, Calif.) according to manufacturer's instructions. Additionally, macrophages are infected for 7 days and then analyzed by RT-PCR to measure steady-state levels of CCL3 (MIP-1α), CCL4 (MIP-1β) and CCL5 (RANTES).

In vitro immunization assay for T cell responses: DCs from an HIV seronegative donor are exposed to different HIV viruses for 6 days which introduced HIV antigens into these antigen-presenting cells. The DCs are then incubated with autologous T cells for 12-days in the presence of 5 μM nevirapine to prevent HIV infection of any added CD4+ T cells. IL-2 (5 U/ml) is added on day 3 and day 8. Following DC-T coculture, antigen-specific T cell responses are quantified by IFN-γ ELIPOT assay. Cultured cells ($10^5$/well) are added to 96-well multiscreen plates (Millipore, Bedford, Mass.) that have been precoated with 0.5 g/ml of anti-IFN-γ monoclonal antibody (BD Biosciences, San Jose, Calif.). A pool of 15-mer Gag HIV-1 Clade B consensus peptides (AIDS Reagent Program Cat. #8117) is added at a final concentration of 5 μg/ml. As a negative control, cells are also cultured without peptide. Plates are incubated overnight at 37° C., 5% $CO_2$ and developed. The numbers of spots are determined using an automated ELISPOT plate reader (CTL Technologies, Cleveland, Ohio), and the spot-forming counts (SFC) are calculated by subtracting the negative-control wells (mean plus 3 standard deviations). A value of 55 SFC/$10^6$ PBMC or greater after subtraction of background is considered positive.

Statistics: Data are analyzed using PRISM 4.0 (GraphPad Software, La Jolla, Calif.) and expressed as the mean±SEM. Statistical comparisons are analyzed by Student's t test, A P value of 0.05 is considered statistically significant.

Electroporation of DCs with LMP1 and LMP1-CD40 mRNAs: Plasmids containing the coding sequences for LMP1 (pLMP1) and LMP1-CD40 (pLMP1-CD40) are linearized by digestion with NdeI downstream of the poly A tail and then in vitro transcribed with 17 polymerase to synthesize capped mRNA with additional poly (A) tail using the mMessage mMachine kit (Ambion, Austin, Tex.). DC cultures are re-suspended at a concentration of $10^7$ cells/ml in Opti-MEM medium (Invitrogen), following which 0.2 ml is added to a 4 mm electroporation cuvette along with 10 μg of mRNA. Transfection is performed by electroporation using a Gene Pulser (BioRad Laboratories, Hercules, Calif.) set to 350 V, 150 μF. Following electroporation, the cells are plated in 6 well plates in complete RPMI 1640 and cultured for another 48 hours.

Preparation and characterization of virus stocks: To prepare viruses from the proviral clones, $5 \times 10^6$ 293T cells are first plated in 100 mm diameter dishes in complete DMEM. The next day, 5 μg of either pHIV, pHIV-EGFP, pHIV-LMP1, pHIV-LMP1-CD40 plasmid DNA is transfected using the GenJet Plus Transfection Reagent according to the manufacturer's instructions (Signagen Laboratories, Iamsville, Md.). The cell culture media is replaced 24 hours later, and virus-containing supernatants are collected after a further 24 hours in culture. Cell debris is removed by centrifugation and the supernatants are filtered through a 0.45μ membrane (Millipore, Bedford, Mass.). Virus stocks are titered using the TZM-bl cell assay and expressed as the 50% tissue culture infectious dose ($TCID_{50}$) as calculated using the Reed and Muench formula. For the experiment shown in FIG. 14, the virus stock is further purified using immunomagnetic beads (μMACS Virus Isolation Kit, Miltenyi Biotec, Auburn, Calif.), which eliminates the possible confounding effects of non-virion soluble molecules or cellular debris.

Western blotting for LMP1 and LMP1-CD40 expression is used to confirm that HIV-LMP1 and HIV-LMP-CD40 viruses lead to expression of their respective proteins in 293 T cell viral lysates. SDS lysis buffer is added to cells and run on a 10% SDS-PAGE gel, following by transfer to nitrocellulose membranes, blocking with 5% evaporated milk with 0.2% Tween-20 in PBS. Membranes are stained overnight at 4° C. with either mouse anti-EBV LMP1 monoclonal antibody (3H2104,a,b,c, 1:100 dilution, Santa Cruz Biotechnology, Santa. Cruz, Calif.) or rabbit anti-human CD40 polyclonal antibody (C-20, 1:200 dilution, Santa Cruz Biotechnology, Santa Cruz, Calif.). Membranes are then washed with PBS-0.2% Tween-20 and incubated with either horseradish peroxidase (HRP)-conjugated goat anti-mouse or anti-rabbit antibody (Pierce, Rockford, Ill.) at a 1:5,000 dilution in blocking buffer. Then the membranes are washed and incubated in HRP substrate (Pico chemiluminescence; Pierce), placed on Whatman 3MM filter paper and exposed to film (BioMax; Kodak, Rochester, N.Y.). Bands of the predicted sizes are observed for p24 Gag (24 kDa), LMP1 (39 kDa), LMP1-CD40 (26 kDa).

Measurement of DC and macrophage activation by flow cytometry: To assess the maturation and activation of DCs and macrophages, the conjugated monoclonal antibodies against the following surface molecules are used: CD40 (clone 5C3, BD Pharmingen, San Diego, Calif.); CD80 (clone L307.4, BD Pharmingen, San Diego, Calif.); CD83 (clone HB15, BD Pharmingen, San Diego, Calif.); and CD86 (clone 2331, BD Pharmingen, San Diego, Calif.); HLA-DR (clone L243, BD Pharmingen, San Diego, Calif.); CCR7 (clone 3D12, BD Pharmingen, San Diego, Calif.).

Quantitative RT-PCR for chemokine mRNAs: Macrophages are infected for 7 days and then analyzed by RT-PCR to measure steady-state levels of CCL3 (MIP-1α), CCL4 (MIP-1β), and CCL5 (RANTES). Total RNA is prepared using RNeasy kit (Qiagen Valencia, Calif.), treated with RNAse-free DNAse (Roche Molecular Biochemicals, Indianapolis, Ind.) and used as template in an RT-PCR assay. RNA is reverse transcribed in a 20 μl reaction containing 0.1 μg of total RNA, 0.1 μg of oligo(dT), 200 U of reverse transcriptase (Finnzymes, Finland) and 0.2 μM each of dATP, dCTP, dGTP and dTTP. After incubation at 40° C. for 1 hour to generate cDNA, aliquots are analyzed by real-time PCR using the Power SYBR Green Supermix (Applied Biosystems). The following primers are used: CCL3 (MIP-1α)-specific primers, 5'-GTCTGTGCTGATCCCAGTGA-3' (forward) (SEQ ID NO: 5) and 5'-TTGTCACCAGACGCG-GTGTG-3' (reverse) (SEQ ID NO: 6); CCL4 (MIP-1β)-specific primers, 5'-GTCTGTGCTGATCCCAGTGA-3' (forward) (SEQ ID NO: 7) and 5'-GGACACTTATC-CTTTGGCTA-3' (reverse) (SEC) ID NO: 8); CCL5 (RANTES)-specific primers, 5'-CCGCGGCAGC-CCTCGCTGTCATCC-3 (forward) (SEQ ID NO: 9) and 5'-CATCTCCAAAGAGTTGATGTACTCC-3' (reverse) (SEQ ID NO: 10). For normalization, GAPDH and β-actin real-time PCR is carried out on the same samples. Normalized mRNA levels for each transcript are calculated as (½ΔCt×1,000), where ΔCt value=Ct (test mRNA)–Ct (GAPDH mRNA). To control for contamination with genomic DNA, parallel amplifications are performed in the absence of reverse transcriptase and are uniformly negative.

Example 12

Figure 1A:
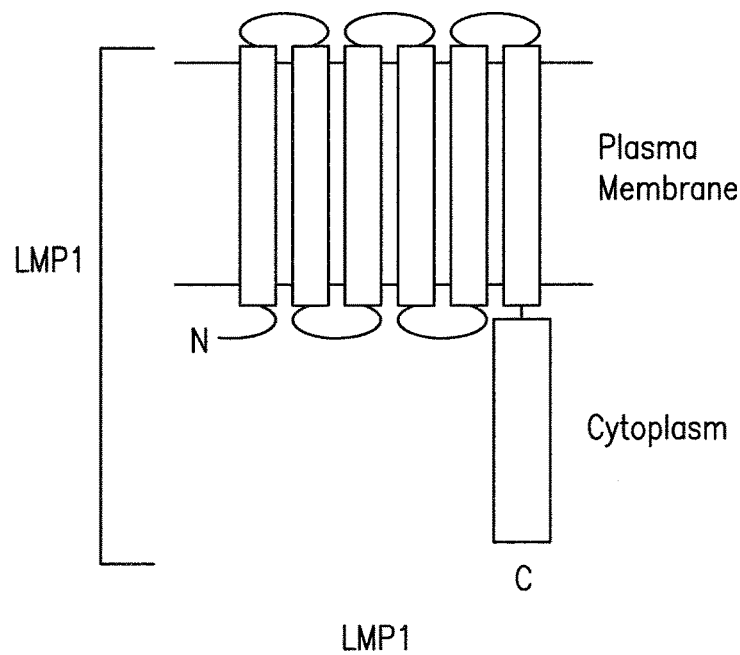
FIG. 1 shows the latent membrane protein 1 (LMP1) and LMP1-CD40 as prototypes for a multimerizing-intracellular signaling cassette. LMP1 from the Epstein-Barr Virus (EBV) is a membrane-associated protein with an N-terminus that contains six transmembrane domains and a C-terminus that includes an intracellular signaling domain. The LMP1 N-terminus is known to self-associate, leading to the formation of clustered, multimeric patches in the plane of the membrane. LMP1-CD40 is a chimeric fusion protein which employs the N-terminus of LMP1 for multimerization and membrane association and the intracellular signaling domain of CD40. In one aspect, no spacer or linker is present between the LMP1 and CD40 portions, but they can be easily included into the sequence. Both LMP1 and LMP1-CD40 are constitutively active, meaning that no ligand or other stimulus is needed for them to initiate signaling through the CD40 pathway.
Figure 1B:
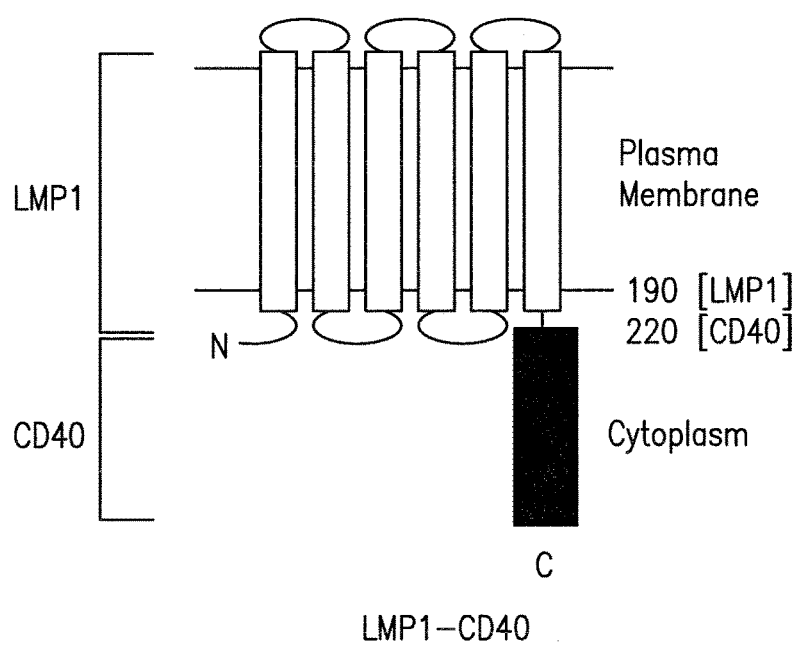

EBV LMP1 Activates Dendritic Cells and Functions as a Molecular Adjuvant when Incorporated into an HIV Vaccine Preparation of LMP1 and LMP1-CD40: The Raji B cell line is used for the preparation of LMP1 cDNA which encoded a 387 amino acids protein. To prepare LMP1-CD40, PCR gene construction techniques are used to fuse the nucleotides for the N-terminal 190 AA of LMP1 (GenBank M58153.1) with the C-terminal cytoplasmic tail of human CD40 (residues 220-277, GenBank NM_001250). The resulting proteins are depicted in FIG. 1. Notably, LMP1 N-terminal residues form a domain with six transmembrane regions that self-associates in the plane of the membrane, thereby clustering the cytoplasmic tails of these proteins. On the intracellular side of the plasma membrane, the clustered signaling domains recruit adapter molecules such as TRAFs to initiate downstream signaling events. CD40L is not needed to induce clustering of these receptor mimics and as a result both LMP1 and LMP1-CD40 are constitutively active.

Electroporation of mRNAs for LMP1 or LMP1-CD40 activate DCs: Both LMP1 and LMP1-CD40 are known to be active in B cells and certain epithelial cells, but their effects on DCs are not previously known. Consequently, in vitro transcribed mRNA for LMP1 or LMP1-CD40 is electroporated into DCs. For comparison, control cultures included DCs electroporated without added mRNA (mock) and DCs electroporated with mRNA for enhanced green fluorescent protein (GFP), an inactive protein. As shown in FIG. 12A, LMP1 or LMP1-CD40 mRNA alone is sufficient to upregulate CD40, CD80, and the CD83 maturation marker on DCs as measured by flow cytometry. CD86 expression, however, is not significantly changed, reflecting its independent regulation in these cells. In parallel with these membrane changes, DCs are also stimulated to secrete cytokines in to the media as measured by cytometric bead assay (CBA) (FIG. 12B). Both LMP1 and LMP1-CD40 induce sizable amounts of TNFα, IL-6, and IL-8. A trace amount of IL-1β is produced as well, but essentially IL-10 or IL-12p70 is made. The lack of IL-12p70 production is consistent with reports that CD40 stimulation alone is insufficient to cause IL-12p70 production in the absence of a second stimulus such as bacterial endotoxin/LPS or other TLR agonist. Thus, the data demonstrate that LMP1 and LMP1-CD40 are sufficient to activate many important DC functions even when used alone as unvectored isolated gene cassettes.

Introduction of LMP1 or LMP-1-CD40 into an HIV-1 proviral construct: Given the DC-activating effects of LMP1 and LMP1-CD40 alone, the present invention provides that they can retain this function when produced in the context of a viral vector. Consequently, a proviral clone of pNL4-3 is obtained that has been modified to contain the macrophage-trophic envelope gene of HIV-1BAL yielding a CCR5-utilizing virus that can infect DCs and macrophages. This virus is further engineered using the design of Levy et al. (2004) Proc Natl Acad Sci USA 101: 4204-9, where exogenous coding sequences can be inserted into the HIV-1 genome just 5-prime to nef, followed by an internal ribosome entry site (IRES) that allows continued translation of the Nef protein (FIG. 2). This results in infection-competent, replicating viruses that express either LMP1 (HIV-LMP1) or an LMP1-CD40 fusion (HIV-LMP1-CD40). When the plasmids encoding HIV-LMP1 or HIV-LMP1-CD40 are transfected into 293 cells, the synthesis of correctly sized LMP1 and LMP1-CD40 proteins is demonstrated by Western blotting (FIG. 16).

HIV-LMP1 and HIV-LMP1-CD40 stimulate DCs and macrophages to upregulate immunologically important cell surface molecules. DCs and macrophages are transduced with HIV-LMP1 HIV-LMP1-CD40 and cultured for 4 days to allow these viruses to enter the cells and express virally encoded proteins. At this time point, DCs develop extensive dendritic processes similar to the changes induced by stimulation with cells expressing membrane CD40L. Using flow cytometry analysis, both engineered viruses affect DCs (FIG. 13A) by upregulating CD40, CD80, and CD83, and had only minor effects on the expression of CD86. A similar pattern of DC activation is shown when LMP1 or LMP CD40 mRNAs are electroporated into DCs (FIG. 12A), indicating that the specific functions of these molecules are unchanged by incorporation into a viral vector. In addition, HLA-DR (an MHC-II molecule) and CCR7 are also studied. While HIV-LMP1 and HIV-LMP1-CD40 do not affect HLA-DR expression by DCs and macrophages, both of these engineered viruses upregulate CCR7 expression. Since CCR7 controls the entry of cells into lymph nodes, the present invention provides that the CCR7 upregulation produced by HIV-LMP1 or HIV-LMP1-CD40 can allow these transduced cells to migrate to lymph nodes where they can in turn present the viral antigens encoded by the HIV vector.

Similarly, macrophages are strongly stimulated by HIV-LMP1 and upregulated CD40, CD80, CD83, and CD86 expression (FIG. 13B). In contrast, HIV-LMP1-CD40 is not a strong stimulator of macrophages, although CD86 is modestly upregulated. These changes are mirrored in the morphological changes observed in these cultures. HIV-LMP1 exposed macrophages undergo extensive cell-cell clumping as previously reported using CD40L stimulation. In contrast, HIV-LMP1-CD40 induces a more modest degree of clumping. Thus, for these cell surface proteins, it appears that LMP1 is strongly active in both DCs and macrophages whereas LMP1-CD40 is more active in DCs than macrophages.

HIV-LMP1 and HIV-LMP1-CD40 stimulate DCs and macrophages to produce cytokines and chemokines. As further studies of the DCs and macrophages cultures shown in FIG. 13, culture supernatants from day 4 are studied for the secretion of cytokines and chemokines. For DCs (FIG. 14A), HIV-LMP1 significantly increases the production of IL-1β, IL-6, IL-8, IL-12p70, and TNFα. In contrast, HIV-LMP1-CD40 is less active than HIV-LMP1 for cytokine induction in DCs. As shown in FIG. 14B, HIV-LMP1 and HIV-LMP1-CD40 induces macrophages to make IL-6, IL-8, and small amounts of IL-12p70, IL-1β and TNFα. In contrast, there are no significant effects on IL-10 production. Serial measurements made on days 4, 7, and 10 show that high levels of IL-1β, IL-6, and IL-8 persist in these cultures, whereas IL-10, IL-12p70, and TNFα fall to background levels by day 10. In addition, steady-state levels of three chemokines (CCL3 (MIP-1α), CCL4 (MIP-1β), and CCL5 (RANTES)) are increased in macrophages infected by HIV-LMP1 and especially HIV-LMP1-CD40, suggesting fine differences in the cell signaling produced by the two viral constructs (FIG. 17).

HIV-LMP1 and HIV-LMP1-CD40 upregulate the antigen-presenting functions of DCs in an in vitro immunization assay. To provide an initial indicator of the effects of HIV-LMP1 and HIV-LMP1-CD40 on immune responses to the HIV viral vector, an in vitro immunization model is used. This assay relies on the fact that T cells from HIV-uninfected individuals have a low but definite frequency of reactivity to HIV antigens. Consequently, when purified autologous T cells are cultured on DCs exposed to these viruses and supplemented with IL-2, the rare anti-HIV T cells in the population can be expected to respond to the HIV antigens in the DCs. Using an IFN-γ ELISPOT assay and a pool of HIV Gag peptides, exposure to HIV-LMP1 is found to significantly enhance the in vitro response to Gag antigen (FIG. 15). In contrast, HIV-LMP1-CD40 is no better than control HIV-GFP in this assay. Thus, in some embodiments, HIV-LMP1 is a strong immunogen in vivo and it may be more active than HIV-LMP1-CD40.

Example 13

LMP1 and LMP1-CD40 can be Used as Immune Stimulators for DCs and Macrophages

The starting point is the clinical observation that EBV infection elicits extremely strong CD8+ T cell responses directed against its own antigens and immunological studies showing that this virus contains a viral mimic of the CD40 receptor, LMP1, which is constitutively active. LMP1 is known to be active in B cells, but its effects on DCs and macrophages had not been previously reported. The present invention provides that LMP1 and LMP1-CD40 are activators of these cells and can be inserted into viral vectors, for example HIV, to convert a weakly immunostimulatory virus into a strong immune stimulator that can be used as the basis for a candidate vaccine.

The key finding is that LMP1 and LMP1-CD40 can be used in isolation to stimulate DCs and macrophages. This can be accomplished by electroporating mRNAs for these genes into these cells in vitro and observing the pattern of activation that resulted. Costimulatory proteins on the cell surface are upregulated and cytokine production is induced. These data confirm prior reports that the transfection of plasmid DNA encoding LMP1 has strong CD40L-like activating effects on B cells and B cell-derived tumor lines. Extending these prior findings, the present example shows that LMP1 and LMP1-CD40, separate from any vector containing them, can act alone as completely functional immunostimulatory molecules capable of activating DCs and macrophages.

As adjuvant molecules, LMP1 and LMP1-CD40 offer several advantages: First, LMP1 is one of the few immunostimulatory proteins that do not elicit strong CD8+ T cell responses against itself. While very strong CD8+ T cell responses are directed against the lytic proteins expressed by EBV, CD8+ T cell reactivity against LMP1 is difficult to detect. Thus, DCs and macrophages activated by LMP1 (and presumably also LMP1-CD40) are not likely to be rapidly killed by pre-existing or induced CD8+ T cells recognizing peptides from this protein.

Second, LMP1 and LMP1-CD40 have potential advantages over using CD40L as a molecular adjuvant. Prior studies have shown that the inclusion of CD40L into Vaccinia, canarypox, adenovirus, lentiviral vectors, and SIV significantly improved the immunogenicity of these viruses and viral vectors. In all of these cases, the production of virus or virus-like particles (VLPs) from CD40L-expressing cells leads to virions and VLPs bearing functional CD40L on their membrane surface, which can be problematic. Virions and VLPs bearing surface CD40L can bind indiscriminately to the many cell types that express the CD40 receptor, including B cells and endothelial cells. This binding can have functional consequences and CD40L-bearing viruses and VLPs have been shown to activate bystander B cells and macrophages. This results in a potential for inducing autoimmunity and other deleterious effects. In contrast, LMP1 and LMP1-CD40 are cell-associated proteins that internally activate the cells that express them; they do not confer a ligand-like ability to activate other cells that come in contact with the cells that express them. Thus, and LMP1-CD40L should not disturb the cell-targeting qualities built into a viral vector nor should they lead to wide-spread and possibly toxic bystander cell activation. As a result, the present invention provides that a viral vector bears these molecules to be "self-adjuvanting," where the tight linkage in time and space of the vector-expressed antigen to these adjuvant molecules allows these two moieties to serve as a complete immunogen, focusing the immune response on the selected antigen.

In addition to LMP1 and LMP1-CD40, a chemically controlled method of multimerizing the CD40 intracellular signaling domain has been developed. In their system, chemically induced dimerization (CID), a bivalent chemical is used to cluster specially modified CD40 domains tethered to the cytoplasmic side of the plasma membrane. Like LMP1 and LMP1-CD40, this approach requires the introduction of gene constructs into cells either by plasmid transfection or viral transduction. Unlike LMP1 and LMP1-CD40, the system requires the separate administration of the CID crosslinking molecule so that it attains pharmacologically adequate tissue levels in vivo. This degree of regulatory control in this system is attractive, but it can be achieved in other ways. For example, the LMP1 and LMP CD40 system described herein can be regulated using an inducible promoter system. The Tet-On promoter system can be optimized to create an HIV construct that replicates only in the presence of doxycycline. Such a conditionally replicating form of HIV-LMP1 or HIV-LMP1-CD40 can be a safer way of using these vaccine candidates. Even safer would be to use a form of HIV or lentivirus that is limited to a single cycle of replication in vivo. The present invention provides that any viral vector well known in the art can be modified to include LMP1 or LMP1-CD40 as molecular adjuvants.

The studies reported herein suggest yet other modifications for improved vectored vaccines. CD40 stimulation is highly synergistic with Toll-like receptor (TLR) stimulation for the induction of CD8+ cell responses, which raises the possibility of combining LMP1 or LMP1-CD40 with constitutively active forms of TLRs. Also, in vivo studies are needed to determine if the fine differences between LMP1 and LMP1-CD40 signaling will result in meaningful differences in vaccine responses.

In conclusion, this example describes two portable genetic adjuvants, LMP1 and LMP1-CD40, which can be used to activate DCs and macrophages. These molecules have considerable potential for strengthening existing vaccines based on attenuated viruses or viral vectors. In particular, they can be especially important for the design of HIV vaccines given our finding that these genetic adjuvants can be easily introduced into the genome of this otherwise poorly immunogenic virus.

Example 14

Latent Membrane Protein 1 as a Molecular Adjuvant for Single-Cycle Lentiviral Vaccines Molecular adjuvants are a promising method to enhance virus-specific immune responses and protect against HIV-1 infection. Immune activation by ligands for receptors such as CD40 can induce dendritic cell activation and maturation. The present example provides the incorporation of two CD40 mimics, Epstein Barr Virus gene LMP1 or an LMP1-CD40 chimera, into a strain of SIV that is engineered to be limited to a single cycle of infection.

Full length LMP1 or the chimeric protein LMP1-CD40 is cloned into the nef-locus of single-cycle SIV. Human and Macaque monocyte derived macrophages and DC are infected with these viruses. Infected cells are analyzed for activation surface markers by flow cytometry. Cells are also analyzed for secretion of pro-inflammatory cytokines IL-6, IL-8, IL-12p70 and TNFα by cytometric bead array.

Overall, single-cycle SIV expressing LMP1 and LMP1-CD40 produces a broad and potent Th1-biased immune response in human as well as rhesus macaque macrophages and DC when compared with control virus. Single-cycle SIV-LMP1 also enhances antigen presentation by lentiviral vector vaccines; illustrating that LMP1-mediated immune activation can enhance lentiviral vector vaccines against HIV-1.

To develop an effective lentiviral vector vaccine against HIV-1 infection it may be necessary to focus on enhancing the activation of dendritic cells, and other professional antigen presenting cells, in order to maximize the stimulation of virus-specific immune responses. One of the critical events in the induction of immune response is the maturation of DCs and macrophages. Maturing DCs and macrophages undergo a rapid burst of cytokine synthesis and expression of costimulatory molecules. Dendritic cells then migrate to the T-cell areas of draining secondary lymphoid organs to prime naïve T cells and initiate an adaptive immune response. IL-12p70 is secreted by activated macrophages and DC and stimulates IFN-γ secretion by T lymphocytes and NK cells. To improve the efficacy of vaccines, single-cycle SIV vaccines can be developed by incorporating inducers of antigen presenting cell maturation and cytokine secretion, specifically looking at CD40 stimulation and the role of the viral protein LMP1.

LMP1 is an integral membrane protein of Epstein Barr Virus (EBV) with a molecular weight of approximately 63 kDa consisting of three domains. LMP1 expression induces many of the changes associated with EBV infection and activation of primary B cells, including cell clumping; increased cell surface expression of CD23, CD39, CD40, CD44; decreased expression of CD10; and increased expression of the cell adhesion molecules CD11a (LFA1), CD54 (ICAM1), and CD58 (LFA3). At least four signaling pathways; namely nuclear factor κB (NF-κB), c-Jun N-terminal kinase (JNK)-AP-1, p38/MAPK (mitogen activated protein kinase), and Janus kinase (JAK)-STAT (signal transducers and activators of transcription), are implicated in the function of LMP1. Within the C-terminus of there are at least two activating regions referred to as CTAR1 and CTAR2 (C-terminal activating region). CTAR1 is located proximal to the membrane (amino acids 186-231) and is essential for EBV mediated transformation of primary B CTAR2 (amino acids 351-386) is located at the extreme C-terminus of LMP1 and is required for long term growth of EBV positive primary B cells. Both CTAR1 and CTAR2 can activate NF-κB independently. Aggregation of LMP1 within the plasma membrane is a crucial prerequisite for signaling. LMP1 aggregation appears to be an intrinsic property of the transmembrane domain. This signaling is similar to signaling by the tumor necrosis factor receptor (TNFR) CD40. The main difference between LMP1 and the TNFR family is that LMP1 functions as a constitutively activated receptor and, therefore, does not rely on the binding of an extracellular ligand for costimulation. Experiments have also evaluated the chimeric molecule LMP1-CD40, consisting of the LMP1 transmembrane domain and the CD40 cytoplasmic tail. These experiments suggest that the LMP1-CD40 chimera is also constitutively active in vitro.

In the present example, LMP1 and LMP1-CD40 genes are incorporated into the genome of pseudotyped single-cycle SIV viral particles. These genes are expected to enhance the immunogenicity of the virus, thereby stimulating antigen presentation by infected APC. The immunogenicity of SIV-LMP1 and SIV-LMP1-CD40 are evaluated in vitro using human as well as macaque monocyte-derived DCs and macrophages. The present invention provides that LMP1 and LMP1-CD40 significantly enhance the ability of SIV to activate DCs and macrophages. SIV-LMP1 also enhances the priming of naive Gag-specific T cells in vitro. These results are encouraging for the clinical evaluation of LMP1 and LMP1 chimeric constructs as a novel class of adjuvant for HIV vaccines and other immunotherapy strategies.

Cells and media: Embryonic kidney (293T) cells are grown at 37° C. under 5% $CO_2$ in Dulbecco's modified Eagle medium (DMEM) supplemented with 10% fetal bovine serum (FBS), 2 mM. L-glutamine, and antibiotics (100 U/ml penicillin and 100 μg/ml streptomycin), (referred to as complete medium). Human as well as rhesus macaque peripheral blood mononuclear cells (PBMCs) are prepared by Ficoll-Hypaque density centrifugation and maintained in RPMI medium (Hyclone, Logan, Utah) supplemented with 5% human serum (Lonza, Allendale, N.J.) and 10 mM HEPES (Invitrogen, Carlsbad, Calif.).

Plasmid Construction: The construct SIVmac239 FS-ΔPR-ΔINEGFP contains mutations in the gag-pal frameshift site (FS) and deletion in the protease (ΔPR) integrase (ΔIN) coding regions of the pot gene. The Nef coding region is replaced with GFP. All constructs with the immunostimulatory genes LMP1 or LMP1-CD40 are cloned by overlap PCR and inserted into the SIVmac239 FS-ΔPR-ΔINEGFP vector using unique XbaI and SacII sites flanking the GFP gene. All viral clones are confirmed by DNA sequencing both before and after ligation into the viral vector. All DNA plasmids are purified with the Qiagen Endo-Free kit and checked for endotoxin levels prior to transfection.

Preparation of viral stocks: Single-cycle virus stocks are prepared by harvesting the supernatant of 293T cells transfected with different viral plasmids. VSV-G trans-complemented single-cycle SIV is produced by co-transfection of 293T cells with the Gag-Pot expression construct pGPfusion, 5 μg of an expression construct for the Indiana or the New Jersey serotype of VSV-G and a full-length proviral DNA construct for each scSIV strain. 293T cells are seeded at $5 \times 10^6$ cell per 100-mm dish in cell culture medium (Dulbecco's modified Eagle's medium [DMEM] supplemented with 10% fetal bovine serum [FBS], L-glutamine, penicillin and streptomycin) and transfected the following day with 5 μg of each plasmid using Genjet plus transfection Reagent (Signagen Laboratories, Iamsville, Md.). Twenty-four hours after transfection, the plates are rinsed twice with serum-free medium and the cell culture medium is replaced with DMEM supplemented with 10% FBS. Twenty-four hours later, the cell culture supernatant is collected, clarified by centrifugation at 500×g for 10 min, and filtered through a 0.45 μm-pore-size membrane (Millipore, Bedford, Mass.). To prepare high-titre stocks, viral particles are concentrated by repeated low speed centrifugation using YM-50 ultrafiltration units (Millipore, Bedford, Mass.). Aliquots (1 mL) of scSIV are cryopreserved at −80° C. and the concentration of virus is determined by p27 antigen capture ELISA (Advanced BioScience Laboratories, Kensington, Md.).

Single-cycle SIV infectivity assays: One million CEM×174 cells are incubated with 100 ng p27 equivalents of scSIV in 100 μl volume for 2 hours at 37° C. Cultures are then expanded to a volume of 2 ml in R10 medium (RPMI supplemented with 10% FBS, L-glutamine, penicillin and streptomycin) and incubated in 24-well plates at 37° C. for 4 days. Cells are treated with Fix and Perm reagents (BD Biosciences, San Jose, Calif.) and stained with FITC-conjugated sly Gag-specific monoclonal antibody (Immunodiagnostics Inc. Woburn, Mass.). After staining, cells are fixed in 2% paraformaldehyde PBS and analyzed by flow cytometry to determine the frequency of SIV Gag-positive infected cells.

Sodium dodecyl sulfate-polyacrylamide gel electrophoresis and Western blotting: Viral particle stocks are run on a 10% sodium dodecyl sulfate-polyacrylamide gel (Bio-Rad, Hercules, Calif.). Proteins are then transferred to nitrocellulose membranes (0.22 µm; GE Osmonics, Minnetonka, Minn.) and blocked (5% milk in PBS-0.2% Tween 20). The membranes are incubated individually with primary antibody overnight at 4° C. These antibodies include the following: (i) 1:100 dilution of mouse anti-EBV LMP1 monoclonal antibody (3H2104,a,b,c Santa Cruz Biotechnology, Santa Cruz, Calif.), (ii) 1:500 dilution of mouse anti-CD40 polyclonal antibody (C-20, Santa Cruz Biotechnology, Santa Cruz, Calif.), and (iii) 1:2,000 dilution of mouse anti-Gag p27 antibody, obtained through the National Institutes of Health AIDS Research and Reference Reagent Program (Germantown, Md.) (SIVmac251 Gag monoclonal [KK64], catalogue no. 2321, from Karen Kent and Caroline Powell). Membranes are washed with PBS-0.2% Tween 20 and incubated with horseradish peroxidase (HRP)-conjugated goat anti-mouse antibody (Pierce. Rockford, Ill.) at a 1:5,000 dilution in blocking buffer. Following incubation in the secondary antibody, the membranes are washed and then incubated HRP substrate (Pico chemiluminescence; Pierce). Membranes are placed on Whatman 3MM filter paper and exposed to film (BioMax; Kodak, Rochester, N.Y.).

Preparation and transduction of monocyte-derived macrophages and dendritic cells: PBMC from healthy blood donors (Continental Blood Services, Miami, Fla.) are isolated from bully coats by density centrifugation using Ficoll-Hypaque (Amersham Pharmacia Biotech Inc., Piscataway, N.J.). Cells are cultured at $2 \times 10^6$ cells/ml, in RPMI-1640 media supplemented with 10% decomplemented human AB serum (Biowhittaker, Walkersvilie, Md.), 2 mmol/liter L-glutamine, 100 U/ml penicillin G and 100 µg/ml streptomycin (GIBCO BRL, Gaithersburg, Md.), in a 5% $CO_2$ atmosphere at 37° C. To isolate monocytes, PBMC underwent plastic adherence on T175 tissue flasks (Corning-Costar, Cambridge, Mass.). To generate enriched populations of monocyte-derived macrophages (macrophages) and monocyte-derived dendritic cells (DCs) the following procedures are performed. To generate macrophages, adherent cells are extensively washed and maintained for 24 hours in medium supplemented with 10% heat-inactivated human serum. Adherent monocytes are washed, removed from the flask by gentle scraping, seeded onto 24-well plates at a density of $1 \times 10^6$ cells/well, and cultured for seven days. To generate immature DCs, plastic-adhered monocytes are cultured in GM-CSF, 800 U/ml and IL-4, 500 U/ml (R & DSystems, Inc., Minneapolis, Minn.) for 5 days, adding fresh GM-CSF and IL-4 on day 3. All cell culture reagents are endotoxin free.

Virus transduction and flow cytometry: Immature DCs or macrophages are transduced at day 6. One million macrophages or DCs are incubated with 50 ng p27 equivalents of scSIV (MOI of 0.05) in 100 µl volume for 2 hours at 37° C. Cultures are then expanded to a volume of 2 ml RPMI supplemented with 5% human serum, L-glutamine, penicillin and streptomycin and incubated at 37° C. for 4 days. The culture supernatants of transduced macrophages or DCs are collected at various time points and stored at −80° C. Macrophages are stained on the plates, while DCs are harvested by gently resuspending the cells and staining with anti-CD40, anti-CD80, anti-CD83, anti-CD86, anti-CD11c or anti-HLA-DR or anti-CCR7 in fluorescence-activated cell sorter buffer (PBS supplemented with 3% fetal calf serum and 0.02% sodium azide). Intracellular staining for p27 is also performed to measure infectivity. Expression is monitored by flow cytometric analysis using a LSRII bioanalyzer (Becton Dickinson) and analyzed using the FlowJo software program (Tree Star, San Carlos, Calif.).

Chemokine and cytokine assays: Cell culture supernatants are obtained from macrophages and DCs infected with different viruses at various time points. Supernatant samples are collected, centrifuged for 5 minutes at 13,000×g to clarify, and the supernatant stored at −80° C. Concentrations of IL-1β, IL-6, IL-8, IL-10, IL-12p70 and TNFα are measured using cytometric bead array (CBA) (BD Biosciences, San Jose, Calif.) according to the manufacturers instructions.

RT-PCR analysis of chemokine mRNA: For the measurement of MIP-1α (CCL3), MIP-1β (CCL4), and RANTES (CCL5) mRNA levels in the infected macrophages and DCs, quantitative RT-PCR is performed. Briefly, total RNA is prepared using the RNeasy kit (Qiagen Inc., Valencia, Calif.), and reverse transcribed in a 20 µl reaction containing 0.1 µg of total RNA, 0.1 µg of oligo(dT), 200 U of reverse transcriptase (Finnzymes, Finland) and 0.2 µM each of dATP, dCTP, dGTP and dTTP. After 1 hr incubation at 40° C., cDNA products are generated. Real-time PCR is performed using the Power SYBR Green Supermix (Applied Biosystems) and the following primers: MIP-1α (CCL3)-specific primers, 5'-GTC TGT GCT GAT CCC AGT GA-3' (forward) (SEQ ID NO: 5) and 5'-TTG TCA CCA GAC GCG GTG TG-3' (reverse) (SEQ ID NO: 6); MIP-1β (CCL4)-specific primers, 5'-GTC TGT GCT GAT CCC AGT GA-3' (forward) (SEQ ID NO: 7) and 5'-GGA CAC TTA TCC TTT GGC TA-3' (reverse) (SEQ ID NO: 8); RANTES (CCL5)-specific primers, 5'-CCG CGG CAG CCC TCG CTG TCA TCC-3' (forward) (SEQ ID NO: 9) and 5'-CAT CTC CAA AGA GTT GAT GTA CTC C-3' (reverse) (SEQ ID NO: 10). For normalization, GAPDH and β-actin real-time PCR is carried out on the same samples. Normalized mRNA levels for each transcript are calculated as ($\frac{1}{2}\Delta Ct \times 1,000$), where $\Delta Ct$ value=Ct (test mRNA)−Ct (GAPDH mRNA). To control for contamination with genomic DNA, parallel amplifications are performed in the absence of reverse transcriptase. These are uniformly negative.

Enzyme Linked Immuno-Spot (ELISPOT) assay: IFN-γ ELISPOT assays are performed as follows. Briefly, isolated PBMCs are plated at a concentration of 100,000 cells per well in 96-well multiscreen plates (Millipore, Bedford, Mass.) that had been precoated with 0.5 glint of anti-IFN-γ monoclonal antibody (BD Biosciences, San Jose, Calif.). An SIVmac239 Gag peptide pool (15-mers overlapping by 11 amino acids (NIH AIDS Reagent Program)) is added at a final concentration of 5 µg/ml. Four wells containing PBMCs and complete medium alone are used as negative controls along with four positive controls with Phorbol Myristate Acetate (PMA, 5 ng/ml) and Ionomycin (500 ng/ml). Plates are incubated overnight at 37° C., 5% $CO_2$ and developed. The numbers of spots per well are counted using an automated ELISPOT plate reader (CTL technologies), and the number of specific spot-forming cells (SFC), is calculated by subtracting the negative-control wells (mean plus 3 standard deviations). A value of 55 SFC/$10^6$ PBMC or greater (after subtraction of background) is considered positive.

Statistics. Data are analyzed using PRISM 4.0 (GraphPad Software, La Jolla, Calif.) and expressed as the mean±SEM.

Statistical comparisons are analyzed by Student's t test. A p-value of 0.05 is chosen for statistical significance.

Example 15

Transduction of Human DCs and Macrophages with SIV Encoding LMP1 and LMP1-CD40 Results in Enhanced Activation and Maturation Preparation of LMP1 and LMP1-CD40: Both LMP1 and LMP1-CD40 chimera genes are constructed from PCR fragments, using Raji B cell line cDNA and human CD40 cDNA as PCR templates. The resulting proteins are depicted in FIG. 1. The LMP1 N-terminal residues form a domain with six transmembrane regions that self-associates in the plane of the membrane, clustering the cytoplasmic tails of the protein. The cytoplasmic tail, either from LMP1 or CD40, contains signaling domains that recruit adapter molecules such as TRAFs to initiate downstream signaling events. Receptor-ligand interaction is not required to induce clustering, and as a result both LMP1 and LMP1 CD40 are constitutively active.

Generation of pseudotyped single-cycle SIV expressing LMP1 or LMP1-CD40: The single-cycle SIV viral construct scSIVmac239FS-ΔPRΔINEGFP is used as a template to generate single-cycle SIV virus expressing either LMP1 or LMP1-CD40 (FIG. 19). After confirming recombinant clones by sequencing, Western blot analysis is performed for Gag, LMP1, and CD40 following transfection of 293T cell lysates with SIV viral constructs. Gag (p27) is present in all 293T lysates, whereas LMP1 and CD40 proteins are present only for LMP1 and LMP1-CD40 adjuvanted viruses, respectively (FIG. 20A). Theoretical molecular weights of LMP1 (42 kDa) and LMP1-CD40 (28 kDa), are consistent with Western blot values (40 kDa and 30 kDa respectively).

Transduction of human DCS and macrophages with SIV encoding LMP1 and LMP1-CD40 results in enhanced activation and maturation. Viruses expressing LMP1-CD40, or control GFP are tested for their ability to activate human DCS and macrophages. The optimal infectious dose is determined as MOI of 0.05 and optimal time for analysis as 4 days post infection (FIG. 27). Under these conditions, scSIV expressing LMP1 or LMP1-CD40 induces morphological changes in DCs and macrophages, including clumping and elongation of cells within the culture. Similar morphological responses are also observed after treatment with LPS, suggesting that LMP1 and LMP1-CD40 are inducing activation of cells within the infected cultures. The expression levels of various maturation and activation surface markers on virus-transduced macrophages and DCs are tested by flow cytometry. Cells are again evaluated 4 days after infection with scSIV viruses. Transduction with scSIV-LMP1 results dendritic cell activation and maturation as measured by significantly increased levels of CD40, CD80 and CD83 expression, while scSIV-LMP1-CD40 results in significant increased levels CD40, CD80 and HLA-DR expression when compared to scSIV-GFP-transduced cells. (FIG. 21A). The present invention provides that the activation signal provided by LMP1 and LMP1-CD40 is strong enough to initiate both activation and maturation of DCs. Similarly, there is a significant increase in the expression of maturation markers CD40 and CD80 scSIV-LMP1 transduced macrophages, whereas scSIV-LMP1-CD40 results in an increase in the expression levels of CD40, CD80 and CD83 (FIG. 21B).

scSIV expressing LMP1 or LMP1-CD40 results in increased secretion of inflammatory cytokines and β-chemokines from human and macaque DCs and macrophages. The secretion of various human inflammatory cytokines by virus-infected DCs or macrophages is evaluated. Inflammatory cytokine assays are performed by cytometric bead array (CBA). DCs are infected with different single-cycle SIV viruses at MOI of 0.05 and supernatants are collected at various time intervals. scSIV-LMP1 infection results in a significant increase in IL-1β, IL-6, IL-8, IL-10, IL-12p70 and TNFα, while scSIV-LMP1-CD40 infection results in increase in IL-1β, IL-6, IL-8, IL-10 and TNFα at various time points (FIG. 24A). Moreover, no measurable amount of IL-12p70 is detected in scSIV-GFP or scSIV-LMP1-CD40 infected DCs.

Table 1—Statistical overview of cytokines secretion from a representative experiment of infected human DCs and macrophages (upper panel) and macaques DCs and macrophages (tower panel) with LMP1 and LMP1-CD40 adjuvanted virus. Human inflammatory cytokine quantitation is performed from the culture supernatants by cytometric bead array (CBA). Data are analyzed with the unpaired t test: *, $p<0.05$; , $p<0.01$; *, $p<0.001$ compared with the scSIV-GFP infected group.

TABLE 1

Statistical overview of cytokines secretion.

| | Cytokines (pg/ml) | Macrophages | | | Dendritic Cells | | |
|---|---|---|---|---|---|---|---|
| | | SIV-EGFP | SIV-LMP1 | SIV-LMP1-CD40 | SIV-EGFP | SIV-LMP1 | SIV-LMP1-CD40 |
| Human cells | IL-1β | 1.53 ± 0.66 | 1.92 ± 0.84 | ND | 1.10 ± 0.73 | 8.54 ± 0.63 ($p < 0.001$) | 2.01 ± 0.62 |
| | IL-6 | 3.53 ± 1.84 | 27.86 ± 4.2 ($p < 0.01$) | 17.21 ± 15.2 | 3.66 ± 2.02 | 265.57 ± 66.45 ($p < 0.01$) | 13.79 ± 0.55 ($p < 0.01$) |
| | IL-8 | 1882.3 ± 335 | 4292.5 ± 646 ($p < 0.05$) | 5000 ± 0.66 ($p < 0.001$) | 537.5 ± 213.3 | 2941.3 ± 338.1 ($p < 0.01$) | 2330.5 ± 39.4 ($p < 0.001$) |
| | IL-10 | 3.66 ± 0.11 | 2.96 ± 0.68 | 3.06 ± 0.31 | 4.53 ± 0.31 | 27.03 ± 6.64 ($p < 0.05$) | 9.57 ± 0.93 ($p < 0.01$) |
| | IL-12p70 | ND | 1.63 ± 0.17 | ND | ND | 55.8 ± 17.57 | ND |
| | TNF | 0.46 ± 0.42 | 3.13 ± 0.11 ($p < 0.01$) | 0.93 ± 0.55 | 0.43 ± 0.57 | 208.39 ± 42.53 ($p < 0.01$) | 13.46 ± 1.15 ($p < 0.001$) |

TABLE 1-continued

Statistical overview of cytokines secretion.

| | | Macrophages | | | Dendritic Cells | | |
|---|---|---|---|---|---|---|---|
| | Cytokines (pg/ml) | SIV-EGFP | SIV-LMP1 | SIV-LMP1-CD40 | SIV-EGFP | SIV-LMP1 | SIV-LMP1-CD40 |
| Macaque cells | IL-1β | 0.13 ± 0.04 | 34.30 ± 1.13 (p < 0.01) | 1.43 ± 0.11 (p < 0.05) | 0.20 ± 0.06 | 2.90 ± 0.80 (p < 0.05) | 0.76 ± 0.82 |
| | IL-6 | 1.90 ± 0.06 | 15.00 ± 2.60 (p < 0.01) | 7.16 ± 1.02 (p < 0.01) | 2.36 ± 0.37 | 173.63 ± 21.91 (p < 0.001) | 89.50 ± 24.60 (p < 0.01) |
| | IL-8 | 64.23 ± 2.57 | 1445.2 ± 158.7 (p < 0.001) | 1107.1 ± 99.5 (p < 0.001) | 2626.6 ± 537.2 | 5001 ± 0.66 (p < 0.001) | 5001 ± 0.66 (p < 0.01) |
| | IL-10 | 0.40 ± 0.53 | ND | 0.40 ± 0.53 | 0.50 ± 0.66 | ND | 0.36 ± 0.48 |
| | IL-12p70 | 0.83 ± 0.48 | 0.80 ± 0.46 | 0.80 ± 0.46 | ND | ND | ND |
| | TNF | 0.76 ± 0.44 | 13.50 ± 2.73 (p < 0.01) | 3.93 ± 0.84 (p < 0.05) | 1.60 ± 0.20 | 294.12 ± 26.15 (p < 0.001) | 99.53 ± 33.31 (p < 0.05) |

Table 1 summarizes the concentration and p-values for cytokines secretion from infected human and macaque DCs and macrophages (data are analyzed with the unpaired t test: *, p<0.05; , p<0.01; *, p<0.001 compared with the SIV-GFP infected group. ND: not detected). Values for scSIV-LMP1 or scSIV-LMP1-CD40 are compared to scSIV-GFP. Significantly higher secretion of inflammatory cytokines is observed from macaque DCs and macrophages upon infection with LMP1 and LMP1-CD40 adjuvanted scSIV viruses compared to control virus. In all assays LPS is used as a positive control and induced high levels of IL-8, IL-6, and TNFα from both dendritic cells and macrophages. These results confirm that LMP1 and LMP1-CD40 are able to activate DCs and macrophages in vitro both in humans and non-human primates. The present invention provides that incorporating LMP1 and LMP1-CD40 into SIV enhances its ability to activate DCs and macrophages. β-chemokine RNA expression is also evaluated by real time RT-PCR of macrophages 4 days following infection. Total cellular RNA is isolated, reverse transcribed to cDNA and MIP-1α, MIP-1β, and RANTES mRNA expression is analyzed by real time PCR assay. When macrophages are infected with recombinant scSIV viruses, LMP1 results in a significant increase in MIP-1β and RANTES mRNA expression, whereas LMP1-CD40 results in significant increase in MIP-1α, MIP-1β and RANTES mRNA expression (FIG. 22B). The present invention provides that expressions of both pro-inflammatory cytokines and β-chemokines are enhanced by single cycle SIV expressing LMP1 or LMP1-CD40.

SIV-LMP1 infected DCs can enhance antigen-specific immune responses from autologous T cells. IL-12p70 is an important regulator of IFN-γ secretion by T cells. The present invention provides that induced IL-12p70 production by scSIV-LMP1 transduced DCs can also increase IFN-γ secretion by autologous T cells following DC stimulation, for example, in a 12-day DC:T cell co-culture assay. DCs are transduced with scSIV-LMP1, scSIV-LMP1-CD40 or scSIV for 4 days, washed, and then cultured with autologous T cells for 12 days in the presence of nevirapine and 5u/ml of IL-2 (FIG. 23A). T cells are then restimulated with an SIV Gag 15-mer overlapping peptide pool (NIH AIDS reagent program). IFN-γ secreting cells are identified by ELISPOT analysis. The scSIV-LMP1 and scSIV-LMP1-CD40 infected DCs induce an increased IFN-γ cell response as compared to the scSIV control (FIG. 23B).

In the present example, methods to develop safe and efficacious SIV vaccines are provided by incorporating adjuvant genes LMP1 and LMP1-CD40 into the genome of single cycle SIV. These and similar vaccination strategies are based on the activation of DCs and macrophages via CD40 signaling, resulting in an inflammatory response that is able to enhance antigen-specific T responses in the vaccine. This CD40 signaling may be especially critical in eliciting CTL responses in conditions such as AIDS where the number or activity of CD4+ cells is limiting. The incorporation of LMP1 and LMP1-CD40 into scSIV viral particles results in enhanced immunogenicity compared to parent scSIV as evidenced by the induction of Th1 cytokines and both DC and macrophage maturation. The scSIV viral genome is an efficient vector for the expression of LMP1, LMP1-CD40 and the synthesis of these virus-encoded proteins is confirmed by Western blot. As an indication of the potency of the LMP1 adjuvants, scSIV viruses expressing LMP1 and LMP1-CD40 induce morphological changes in DCs and macrophages, including clumping and elongation suggestive of activation of these cells.

The immunogenicity of scSIV incorporating LMP1 and LMP1-CD40 is evaluated in vitro by measuring the expression levels of cell surface markers transduced DCs and macrophages. The expression levels of maturation markers CD40, CD80, CD83, CCR7 and HLA-DR are higher in LMP1 and LMP1-CD40 adjuvanted scSIV transduced DCs as compared to the GFP control group. The expression of CD40, CD80, CCR7, and HLA-DR are similar to positive control cells matured with cytokines, however the expression level of CD83 on LMP1 and LMP1-CD40 virus transduced DC is not as high as that on cytokine cocktail-maturated DCs. This could be explained by the fact that the MOI used in the infection experiments is very low (0.05). This low MOI can lead to a low level of transfection, normally 10-20% of cells exposed to SIV constructs. These results suggest that the activation signal provided by LMP1 and LMP1-CD40 is potent enough to initiate activation. There is also a modest increase in the expression of maturation markers such as CD40 and CD83 LMP1 adjuvanted scSIV transduced macrophages, whereas LMP1-CD40 adjuvanted scSIV results in a marked increase in the expression levels of CD40, CD80 and CD83 on infected macrophages. These differences suggest a positive feedback whereby CD40 signaling from LMP1-CD40 enhances the expression of CD40 protein on the cell surface.

Overall, Th1 cytokine secretion is dramatically enhanced by SIV encoding LMP1, with increased cytokine secretion observed within 12-24 hours post-infection. This rapid cytokine induction includes a modest level of IL-12p70, suggesting that SIV-LMP1 infected DCs can potentially enhance SIV-specific T cell response in vivo. This is balanced with a modest secretion of IL-10 following scSIV- LMP1 infection of DC. Much greater secretion levels are observed with cytokines IL-1β, IL-6, TNFα and especially IL-8. Transduction with SIV-LMP1 resulted in a 50-fold induction of IL-12p70 secretion compared to transduction with SIV-GFP (from ~1 pg/ml to 50 pg/ml at 84 hours). Given the critical role of IL-12 in the stimulation of IFN-γ production, proliferation T cells, and generation of cytotoxic T lymphocytes, using LMP1 as an adjuvant can result in increased DC activation and an enhanced Th1 immune response. This IL-12 induction is consistent with LMP1 inducing a constitutive CD40-like signal, a key role in Epstein Barr virus pathogenesis. Binding of CD40L to its receptor on immature DCs triggers DCs activation and maturation and increases DCs survival. One of the cytokines upregulated in DCs activated by CD40L binding is IL-12, a cytokine responsible for polarizing CD4+ T cells to a Th1 phenotype. Researches with DNA vaccines have showed that increasing the activation level of DC through CD40-CD4 interactions significantly enhances the intensity of cell mediated immunity and humoral immune responses. Since IL-12 stimulates production, proliferation of T cells, and generation of cytotoxic T lymphocytes, the present invention provides that LMP1 and LMP1-CD40 result in increased DCs activation and a strong Th1 immune response.

The chemokines MIP-1α, MIP-1β, and RANTES play a critical rote in innate immune control of HIV by DCs and macrophages. Surprisingly, LMP1 and LMP1-CD40 are able to enhance these chemokines in the context of recombinant SIV virus infection. However, LMP1 is unique in its ability to induce IL-12p70, suggesting LMP1 can be a better inducer of T cell responses. Again, this chemokine secretion highlights the ability of LMP1 and LMP1-CD40 to increase the immune response during sly infection of DCs and macrophages and suggests that these recombinant viruses may block viral replication while simultaneously enhances anti-HIV SIV immune responses.

In addition to DC maturation and cytokine secretion, the immunogenicity LMP1 and LMP1-CD40 are further confirmed by the coculture of virus infected DCs with autologous T cells for 12 days. The data suggests that the LMP1 adjuvant gene cassette is able to convert a weakly immunogenic virus into a strongly immunogenic one that can augment T cell responses against viral antigens. By comparison, scSIV-LMP1-CD40 is less active in this assay, consistent with the overall weaker effect of scSIV-LMP1-CD40 DCs compared to scSIV-LMP1 virus.

Thus, the present invention provides that LMP1 or LMP1-CD40 can act as a potent molecular adjuvant, providing a new class of adjuvant for use in recombinant vaccine strategies. In addition, LMP1 and LMP1 chimeras/fusion proteins can be used as viral vector vaccine adjuvants or adjuvants for DNA or RNA based vaccines. Use of LMP1 for these or other subunit vaccine strategies is provided. These vaccines can potentially target DCs, macrophages, and B cells, where B cell responses are also augmented by LMP1 expression, including the induction of T independent class switching.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

Although the invention has been described with reference to the above example, it will be understood that modifications and variations are encompassed within the spirit and scope of the invention. Accordingly, the invention is limited only by the following claims.

What is claimed is:

1. An isolated protein comprising a multimerizing domain from the N-terminal fragment of Latent Membrane Protein 1 (LMP1) operatively joined to a cytoplasmic signaling domain of a heterologous receptor such that the protein assembles into a complex of three or more protein moieties; wherein the LMP1 multimerizing domain is translated from nucleic acids that do not contain introns.

2. The protein of claim 1, wherein the cytoplasmic signaling domain comprises a cytoplasmic fragment of a member of Tumor Necrosis Factor Receptor Superfamily (TNFRSF).

3. The protein of claim 1, wherein the cytoplasmic signaling domain comprises a cytoplasmic fragment selected from the group consisting of CD40, CD27, Fas, Lymphotoxin beta receptor (LTBR), nerve growth factor receptor (NGFR), Tumor necrosis factor receptor superfamily member 1A (TNFRSF1A), Tumor necrosis factor receptor superfamily member 1B (TNFRSF1B), Tumor necrosis factor receptor superfamily member 4 (TNFRSF4), Tumor necrosis factor receptor superfamily member 8 (TNFRSF8), Tumor necrosis factor receptor superfamily member 9 (TNFRSF9), Tumor necrosis factor receptor superfamily member 10A (TNFRSF10A), Tumor necrosis factor receptor superfamily member 10B (TNFRSF10B), Tumor necrosis factor receptor superfamily member 10D (TNFRSF10D), Tumor necrosis factor receptor superfamily member 11A (TNFRSF11A), Tumor necrosis factor receptor superfamily member 12A (TNFRSF12A), Tumor necrosis factor receptor superfamily member 13B (TNFRSF13B), Tumor necrosis factor receptor superfamily member 13C (TNFRSF13C), Tumor necrosis factor receptor superfamily member 14 (TNFRSF14), Tumor necrosis factor receptor superfamily member 17 (TNFRSF17), Tumor necrosis factor receptor superfamily member 18 (TNFRSF 18), Tumor necrosis factor receptor superfamily member 19 (TNFRSF19), Tumor necrosis factor receptor superfamily member 21 (TNFRSF21), and Tumor necrosis factor receptor superfamily member 25 (TNFRSF25).

4. The protein of claim 1, wherein the cytoplasmic signaling domain comprises CD40.

5. The protein of claim 1, wherein the multimerizing domain comprises at least four transmembrane regions.

6. The protein of claim 1, comprising a Latent Membrane Protein 1 (LMP 1)-CD40 fusion protein.

7. An isolated virus, microbe, or host cell, comprising:
(i) a first expression cassette for expressing a protein, comprising a multimerizing domain from the N-terminal fragment of Latent Membrane Protein 1 (LMP1); operatively joined to a cytoplasmic signaling domain of a receptor such that the protein assembles into a complex of three or more protein moieties, and wherein, when the protein is Latent Membrane Protein-1 (LMP1), then the nucleic acid encoding LMP1 does not contain introns; and (ii) a second expression cassette for expressing a protein antigen, with the proviso that the protein antigen is not an Epstein-Barr virus (EBV) protein.

8. The isolated virus, microbe, or host cell of claim 7, whereby the protein comprises cell stimulatory activity from the cytoplasmic signaling domain.

9. The isolated virus, microbe, or host cell of claim 7, wherein the protein comprises:
a multimerizing domain comprising an N-terminus fragment of latent membrane protein 1 (LMP1); and
a cytoplasmic signaling domain comprising a cytoplasmic fragment of a member of Tumor necrosis factor receptor superfamily (TNFRSF).

10. The isolated virus, microbe, or host cell of claim 9, wherein the protein comprises a LMP1-CD40 fusion protein.

11. The isolated virus of claim 7, wherein the virus expresses the protein of claim 8 (i) after infection or transduction of the virus into cells.

12. The isolated virus or microbe of claim 7, wherein the virus or microbe expresses the protein of claim 7 (i) after infection or transduction of the virus or microbe into cells, wherein the virus or microbe is selected from the group consisting of Human immunodeficiency virus-1 (HIV-1), Simian immunodeficiency virus (SIV), influenza virus, parainfluenza virus, dengue virus, Hepatitis A virus, Hepatitis B virus, Hepatitis C virus, Cytomegalovirus (CMV), adenovirus, adeno-associated virus, Simian virus 40 (SV 40), Modified Vaccinia Ankara (MVA), Vesicular stomatitis virus (VSV), arenaviruses, bunyaviruses, flaviviruses, West Nile virus, Japanese Encephalitis virus, Venezuelan equine encephalitis virus, Eastern equine encephalitis virus, Western equine encephalitis, herpesviruses, measles virus, rhabdoviruses, *Listeria, Salmonella*, and combinations thereof.

13. The isolated virus, microbe, or host cell of claim 7, wherein the antigen comprises a tumor antigen, viral antigen, or microbial antigen.

14. The isolated host cell of claim 7, wherein the host cell is a microorganism.

15. An immunogenic composition, comprising:
(i) a delivery system comprising a microorganism other than Epstein-Barr virus (EBV);
(ii) an antigen comprising a tumor antigen, viral antigen, or microbial antigen, wherein the antigen is endogenous to the microorganism used to deliver the immunogenic composition or not normally expressed by the microorganism used to deliver the immunogenic composition, and wherein the antigen is not an EBV protein;
(iii) a protein encoded by the expression cassette of claim 7 (i) and
(iv) wherein the immunogenic composition induces a dendritic cell, macrophage, T cell lymphocyte, or anticancer response greater than that induced by the same composition lacking the expression cassette of claim 7 (i).

16. The immunogenic composition of claim 15, wherein the protein encoded by the expression cassette of claim 7 (i) is comprised of a multimerizing domain comprising an N-terminus fragment of latent membrane protein 1 (LMP1) and a cytoplasmic signaling domain comprising a cytoplasmic fragment of a member of the Tumor necrosis factor receptor superfamily (TNFRSF).

17. The immunogenic composition of claim 15, wherein the protein encoded by the expression cassette of claim 7 (i) comprises a LMP1-CD40 fusion protein.

18. The immunogenic composition of claim 15, wherein the delivery system comprises a DNA virus, RNA virus, or prokaryotic organism.

19. The immunogenic composition of claim 15, wherein the delivery system comprises a virus or microbe selected from the group consisting of Human immunodeficiency virus-I (HIV-1), Simian immunodeficiency virus (SIV), influenza virus, parainfluenza virus, dengue virus, Hepatitis A virus, Hepatitis B virus, Hepatitis C virus, Cytomegalovirus (CMV), adenovirus, adeno-associated virus, Simian virus 40 (SV 40), Vaccinia virus, Modified Vaccinia Ankara (MVA), Vesicular stomatitis virus (VSV), arenaviruses, bunyaviruses, flaviviruses, West Nile virus, Japanese encephalitis virus, Venezuelan encephalitis virus, Eastern equine encephalitis virus, herpesviruses, measles virus, rhabdovirus, *Listeria, Salmonella*, and combinations thereof.

20. A method for stimulating an immune response in a subject comprising: administering to a cell an effective amount of a polynucleotide comprising a first expression cassette for expressing the protein of claim 1, and/or a second expression cassette for expressing an antigen, thereby stimulating an immune response.

21. The method of claim 20, wherein at least two nucleic acid sequences are administered, where a first nucleic acid sequence comprises the first expression cassette for expressing the protein of claim 1, and a second nucleic acid sequence comprises the second expression cassette for expressing an antigen, and the two nucleic acid sequences are contained within the same or two different polynucleotide molecules.

22. The method of claim 20, wherein the nucleic acid comprises a DNA vaccine.

23. The method of claim 20, wherein the nucleic acid comprises an in vitro synthesized and optionally modified RNA molecule.

24. The method of claim 20, wherein the cytoplasmic signaling domain comprises a cytoplasmic fragment of a member of Tumor necrosis factor receptor superfamily (TNFRSF).

25. The method of claim 20, wherein the protein comprises a LMP1-CD40 fusion protein.

26. The method of claim 20, wherein the antigen comprises a tumor antigen, viral antigen, or microbial antigen.

27. An avirulent, oncolytic herpes simplex virus having an intact Us12 gene and an endogenous Us11 gene expressed as a late gene, wherein the virus is modified from the wild-type herpes simplex virus with both $_{\gamma 1}34.5$ genes of the virus being deleted and Us11 genes that are expressed as immediate-early (IE) genes being inserted into the $_{\gamma 1}34.5$ gene locus in place of both $_{\gamma 1}34.5$ genes; wherein the virus comprises an expression cassette for expressing the protein of claim 8 (i).

28. A herpes simplex virus 1 (HSV1) strain, lacking one or more of a functional ICP34.5-encoding gene, a functional ICP6-encoding gene, a functional glycoprotein H-encoding gene and a functional thymidine kinase-encoding gene, and which is derived from HSV1 strain JS1 as deposited at the European Collection of Cell Cultures (ECACC) under accession number 01010209; wherein the virus comprises an expression cassette for expressing the protein of claim 7 (i).

29. A herpes simplex virus which: (i) comprises a gene encoding an immunostimulatory protein; (ii) lacks a functional ICP34.5 encoding gene and a functional ICP47 encoding gene; (iii) is replication competent in tumor cells; and (iv) is derived from HSV1 JS1 as deposited at the European collection of cell cultures (ECAACC) under accession number 01010209; wherein the virus comprises an expression cassette for expressing the protein of claim 7 (i).

30. A modified, oncolytic herpes simplex virus (HSV) strain comprising: a modified, oncolytic herpes simplex virus (HSV) strain wherein the HSV strain is a clinical isolate from a recurrent cold sore and has a greater ability than a reference laboratory HSV strain modified in the same manner as the clinical isolate to replicate in or kill tumor cells, and wherein the reference laboratory HSV strain is selected from the group consisting of HSV1 strain 17+, HSV1 strain F and HSV1 strain KOS; wherein the virus comprises an expression cassette for expressing the protein of claim 7 (i).

31. A method of treating cancer in subject comprising:
    administering to the subject an effective amount of an oncolytic virus wherein the virus comprises an expression cassette for expressing the protein of claim 1.

32. The method of claim 31, wherein the oncolytic virus is selected from the group consisting of a Newcastle Disease Virus, a Mumps Virus, a Measles Virus, a Vesicular Stomatitis Virus, a Para-influenza Virus, an Influenza Virus, an Adenovirus, a Herpes Virus, a Vaccinia Virus, a Reovirus, and a Seneca Valley virus, or combinations thereof.

33. A method of preparing a self-adjuvanting immunogenic composition, wherein said composition comprises a genetically modified microorganism, wherein said method comprises insertion of a gene cassette encoding the protein of claim 1 into the genome of the microorganism.

34. The method of claim 33, further comprising delivering the genetically modified microorganism to a subject.

35. The method of claim 33, wherein the protein encoded by the gene cassette comprises LMP1-CD40.

36. The method of claim 33, wherein the microorganism comprises a virus or prokaryotic organism.

37. The isolated virus, microbe, or host cell of claim 7, wherein cytoplasmic signaling domain of the protein comprises a cytoplasmic fragment selected from the group consisting of CD40, CD27, Fas, Lymphotoxin beta receptor (LTBR), nerve growth factor receptor (NGFR), Tumor necrosis factor receptor superfamily member 1A (TNFRSF1A), Tumor necrosis factor receptor superfamily member 1B (TNFRSF1B), Tumor necrosis factor receptor superfamily member 4 (TNFRSF4), Tumor necrosis factor receptor superfamily member 8 (TNFRSF8), Tumor necrosis factor receptor superfamily member 9 (TNFRSF9), Tumor necrosis factor receptor superfamily member 10A (TNFRSF10A), Tumor necrosis factor receptor superfamily member 10B (TNFRSF10B), Tumor necrosis factor receptor superfamily member 10D (TNFRSF10D), Tumor necrosis factor receptor superfamily member 11A (TNFRSF11A), Tumor necrosis factor receptor superfamily member 12A (TNFRSF12A), Tumor necrosis factor receptor superfamily member 13B (TNFRSF13B), Tumor necrosis factor receptor superfamily member 13C (TNFRSF13C), Tumor necrosis Factor receptor superfamily member 14 (TNFRSF14), Tumor necrosis factor receptor superfamily member 17 (TNFRSF17), Tumor necrosis factor receptor superfamily member 18 (TNFRSF18), Tumor necrosis factor receptor superfamily member 19 (TNFRSF19), Tumor necrosis factor receptor superfamily member 21 (TNFRSF21), and Tumor necrosis factor receptor superfamily member 25 (TNFRSF25).

38. The isolated virus, microbe, or host cell of claim 7, wherein the cytoplasmic signaling domain of the protein comprises CD40.

39. The isolated virus, microbe, or host cell of claim 7, wherein the multimerizing domain comprises at least four transmembrane regions.

* * * * *

UNITED STATES PATENT AND TRADEMARK OFFICE
CERTIFICATE OF CORRECTION

Page 1 of 1

PATENT NO. : 10,238,734 B2
APPLICATION NO. : 13/635885
DATED : March 26, 2019
INVENTOR(S) : Richard Syd Kornbluth and Geoffrey William Stone It is certified that error appears in the above-identified patent and that said Letters Patent is hereby corrected as shown below:

In the Claims

In Column 100, Lines 51-59, please amend Claim 27 by replacing "claim 8(i)" with --claim 7(i)--

Signed and Sealed this
Twenty-first Day of April, 2020

Andrei Iancu
*Director of the United States Patent and Trademark Office*

SEQUENCE LISTING

```
<160> NUMBER OF SEQ ID NOS: 14

<210> SEQ ID NO 1
<211> LENGTH: 11481
<212> TYPE: DNA
<213> ORGANISM: Artificial Sequence
<220> FEATURE:
<223> OTHER INFORMATION: Synthetic construct

<400> SEQUENCE: 1
tggaagggct aatttggtcc caaaaaagac aagagatcct tgatctgtgg atctaccaca      60
cacaaggcta cttccctgat tggcagaact acacaccagg gccagggatc agatatccac     120
tgacctttgg atggtgcttc aagttagtac cagttgaacc agagcaagta gaagaggcca     180
aataaggaga gaagaacagc ttgttacacc ctatgagcca gcatgggatg gaggacccgg     240
agggagaagt attagtgtgg aagtttgaca gcctcctagc atttcgtcac atggcccgag     300
agctgcatcc ggagtactac aaagactgct gacatcgagc tttctacaag ggactttccg     360
ctggggactt tccagggagg tgtggcctgg gcgggactgg ggagtggcga gccctcagat     420
gctacatata agcagctgct ttttgcctgt actgggtctc tctggttaga ccagatctga     480
gcctgggagc tctctggcta actagggaac ccactgctta agcctcaata aagcttgcct     540
```

```
tgagtgctca aagtagtgtg tgcccgtctg ttgtgtgact ctggtaacta gagatccctc    600 agacccttt  agtcagtgtg gaaaatctct agcagtggcg cccgaacagg gacttgaaag    660
cgaaagtaaa gccagaggag atctctcgac gcaggactcg gcttgctgaa gcgcgcacgg    720
caagaggcga ggggcggcga ctggtgagta cgccaaaaat tttgactagc ggaggctaga    780
aggagagaga tgggtgcgag agcgtcggta ttaagcgggg gagaattaga taaatgggaa    840
aaaattcggt taaggccagg gggaagaaa caatataaac taaaacatat agtatgggca    900
agcagggagc tagaacgatt cgcagttaat cctggccttt tagagacatc agaaggctgt    960
agacaaatac tgggacagct acaaccatcc cttcagacag gatcagaaga acttagatca   1020
ttatataata caatagcagt cctctattgt gtgcatcaaa ggatagatgt aaaagacacc   1080
aaggaagcct tagataagat agaggaagag caaaacaaaa gtaagaaaaa ggcacagcaa   1140
gcagcagctg acacaggaaa caacagccag gtcagccaaa attaccctat agtgcagaac   1200
ctccaggggc aaatggtaca tcaggccata tcacctagaa ctttaaatgc atgggtaaaa   1260
gtagtagaag agaaggcttt cagcccagaa gtaatacccc tgttttcagc attatcagaa   1320
ggagccaccc cacaagattt aaataccatg ctaaacacag tggggggaca tcaagcagcc   1380
atgcaaatgt taaaagagac catcaatgag gaagctgcag aatgggatag attgcatcca   1440
gtgcatgcag ggcctattgc accaggccag atgagagaac caaggggaag tgacatagca   1500
ggaactacta gtacccttca ggaacaaata ggatggatga cacataatcc acctatccca   1560
gtaggagaaa tctataaaag atggataatc ctgggattaa ataaaatagt aagaatgtat   1620
agccctacca gcattctgga cataagacaa ggaccaaagg aacccttag agactatgta   1680 gaccgattct ataaaactct aagagccgag caagcttcac aagaggtaaa aaattggatg   1740
acagaaacct tgttggtcca aaatgcgaac ccagattgta agactatttt aaaagcattg   1800
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg gaaatgtgga   2040
aaggaaggac accaaatgaa agattgtact gagagacagg ctaattttt agggaagatc   2100 tggccttccc acaagggaag gccagggaat tttcttcaga gcagaccaga gccaacagcc   2160
ccaccagaag agagcttcag gtttggggaa gagacaacaa ctccctctca gaagcaggag   2220
ccgatagaca aggaactgta tcctttagct tccctcagat cactctttgg cagcgacccc   2280
tcgtcacaat aaagatagg gggcaattaa aggaagctct attagataca ggagcagatg   2340
atacagtatt agaagaaatg aatttgccag gaagatggaa accaaaaatg ataggggaa   2400 ttggaggttt tatcaaagta ggacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaaa   2640
taaaagcatt agtagaaatt tgtacagaaa tggaaaagga aggaaaaatt tcaaaaattg   2700
ggcctgaaaa tccatacaat actccagtat ttgccataaa gaaaaagac agtactaaat   2760 ggagaaaatt agtagatttc agagaactta ataagaaac tcaagatttc tgggaagttc   2820
aattaggaat accacatcct gcagggttaa aacagaaaaa atcagtaaca gtactggatg   2880
```

```
tgggcgatgc atattttca gttccttag ataaagactt caggaagtat actgcattta    2940
ccatacctag tataaacaat gagacaccag ggattagata tcagtacaat gtgcttccac   3000
agggatggaa aggatcacca gcaatattcc agtgtagcat gacaaaaatc ttagagcctt   3060
ttagaaaaca aaatccagac atagtcatct atcaatacat ggatgatttg tatgtaggat   3120
ctgacttaga aatagggcag catagaacaa aaatagagga actgagacaa catctgttga   3180
ggtggggatt taccacacca gacaaaaaac atcagaaaga acctccattc ctttggatgg   3240
gttatgaact ccatcctgat aaatggacag tacagcctat agtgctgcca gaaaaggaca   3300
gctggactgt caatgacata cagaaattag tgggaaaatt gaattgggca agtcagattt   3360
atgcagggat taaagtaagg caattatgta aacttcttag gggaaccaaa gcactaacag   3420
aagtagtacc actaacagaa gaagcagagc tagaactggc agaaaacagg agattctaa    3480
aagaaccggt acatggagtg tattatgacc catcaaaaga cttaatagca gaaatacaga   3540
agcaggggca aggccaatgg acatatcaaa tttatcaaga gccatttaaa aatctgaaaa   3600
caggaaaata tgcaagaatg aagggtgccc acactaatga tgtgaaacaa ttaacagagg   3660
cagtacaaaa aatagccaca gaaagcatag taatatgggg aaagactcct aaatttaaat   3720
tacccataca aaaggaaaca tgggaagcat ggtggacaga gtattggcaa gccacctgga   3780
ttcctgagtg ggagtttgtc aatacccctc ccttagtgaa gttatggtac cagttagaga   3840
aagaacccat aataggagca gaaacttct atgtagatgg ggcagccaat agggaaacta   3900
aattaggaaa agcaggatat gtaactgaca gaggaagaca aaaagttgtc ccctaacgg    3960
acacaacaaa tcagaagact gagttacaag caattcatct agctttgcag gattcgggat   4020
tagaagtaaa catagtgaca gactcacaat atgcattggg aatcattcaa gcacaaccag   4080
ataagagtga atcagagtta gtcagtcaaa taatagagca gttaataaaa aaggaaaaag   4140
tctacctggc atgggtacca gcacacaaag gaattggagg aaatgaacaa gtagatgggt   4200
tggtcagtgc tggaatcagg aaagtactat ttttagatgg aatagataag gcccaagaag   4260
aacatgagaa atatcacagt aattggagag caatggctag tgattttaac ctaccacctg   4320
tagtagcaaa agaaatagta gccagctgtg ataaatgtca gctaaaaggg gaagccatgc   4380
atggacaagt agactgtagc ccaggaatat ggcagctaga ttgtacacat ttagaaggaa   4440
aagttatctt ggtagcagtt catgtagcca gtggatatat agaagcagaa gtaattccag   4500
cagagacagg gcaagaaaca gcatacttcc tcttaaaatt agcaggaaga tggccagtaa   4560
aaacagtaca tacagacaat ggcagcaatt tcaccagtac tacagttaag gccgcctgtt   4620
ggtgggcggg gatcaagcag gaatttggca ttccctacaa tccccaaagt caaggagtaa   4680
tagaatctat gaataaagaa ttaaagaaaa ttataggaca ggtaagagat caggctgaac   4740
atcttaagac agcagtacaa atggcagtat tcatccacaa ttttaaaaga aagggggga   4800
ttggggggta cagtgcaggg gaaagaatag tagacataat agcaacagac atacaaacta   4860
aagaattaca aaaacaaatt acaaaaattc aaaattttcg ggtttattac agggacagca   4920
gagatccagt ttggaaagga ccagcaaagc tcctctggaa aggtgaaggg gcagtagtaa   4980
tacaagataa tagtgacata aaagtagtgc caagaagaaa agcaaagatc atcagggatt   5040
atggaaaaca gatggcaggt gatgattgtg tggcaagtag acaggatgag gattaacaca   5100
tggaaaagat tagtaaaaca ccatatgtat atttcaagga agctaaggga ctggttttat   5160
agacatcact atgaaagtac taatccaaaa ataagttcag aagtacacat cccactaggg   5220
gatgctaaat tagtaataac aacatattgg ggtctgcata caggagaaag agactggcat   5280
```

```
ttgggtcagg gagtctccat agaatggagg aaaaagagat atagcacaca agtagaccct   5340
gacctagcag accaactaat tcatctgcac tattttgatt gttttttcaga atctgctata  5400
agaaatacca tattaggacg tatagttagt cctaggtgtg aatatcaagc aggacataac   5460
aaggtaggat ctctacagta cttggcacta gcagcattaa taaaaccaaa acagataaag   5520
ccacctttgc ctagtgttag gaaactgaca gaggacagat ggaacaagcc ccagaagacc   5580
aagggccaca gagggagcca tacaatgaat ggacactaga gcttttagag gaacttaaga   5640
gtgaagctgt tagacatttt cctaggatat ggctccataa cttaggacaa catatctatg   5700
aaacttacgg ggatacttgg gcaggagtgg aagccataat aagaattctg caacaactgc   5760
tgtttatcca tttcagaatt gggtgtcgac atagcaagaa taggtattat tcaacagagg   5820
agagcaagaa atggagccag tagatcctaa actagagccc tggaagcatc caggaagtca   5880
gcctaagact gcttgtacca cttgctattg taaaaagtgt tgctttcatt gccaagtttg   5940
cttcataaca aaaggcttag gcatctccta tggcaggaag aagcggagac agcgacgaag   6000
agctcctcaa gacagtgaga ctcatcaagt ttctctatca aagcagtaag tagtacatgt   6060
aatgcaagct ttacaaatat cagctatagt aggattagta gtagcagcaa taatagcaat   6120
agttgtgtgg accatagtat tcatagaata taggaaaata ttaaggcaaa gaaaaataga   6180
caggttaatt gatagaataa cagaaagagc agaagacagt ggcaatgaga gtgacggaga   6240
tcaggaagag ttatcagcac tggtggagat ggggcatcat gctccttggg atattaatga   6300
tctgtaatgc tgaagaaaaa ttgtgggtca cagtctatta tggggtacct gtgtggaaag   6360
aagcaaccac cactctattt tgtgcatcag atcgtaaagc atatgataca gaggtacata   6420
atgtttgggc cacacatgcc tgtgtaccca cagaccccaa cccacaagaa gtagaattga   6480
aaaatgtgac agaaaatttt aacatgtgga aaaataacat ggtagaacaa atgcatgagg   6540
atataatcag tttatgggat caaagcctaa agccatgtgt aaaattaacc ccactctgtg   6600
ttactttaaa ttgcactgat ttgaggaatg ctactaatgg gaatgacact aataccacta   6660
gtagtagcag gggaatggtg gggggaggag aaatgaaaaa ttgctctttc aatatcacca   6720
caaacataag aggtaaggtg cagaaagaat atgcactttt ttataaactt gatatagcac   6780
caatagataa taatagtaat aatagatata ggttgataag ttgtaacacc tcagtcatta   6840
cacaggcctg tccaaaggta tcctttgagc caattcccat acattattgt gccccggctg   6900
gttttgcgat tctaaagtgt aaagataaga agttcaatgg aaaaggacca tgtacaaatg   6960
tcagcacagt acaatgtaca catggaatta ggccagtagt atcaactcaa ctgctgttaa   7020
atggcagtct agcagaagaa gaggtagtaa ttagatccgc caatttcgcg gacaatgcta   7080
aagtcataat agtacagctg aatgaatctg tagaaattaa ttgtacaaga cccaacaaca   7140
atacaagaaa aagtatacat ataggaccag gcagagcatt ttatacaaca ggagaaataa   7200
taggagatat aagacaagca cattgtaacc ttagtagagc aaaatggaat gacactttaa   7260
ataagatagt tataaaatta agagaacaat ttgggaataa acaatagtc tttaagcact   7320
cctcaggagg ggacccagaa attgtgacgc acagttttaa ttgtggaggg gaatttttct   7380
actgtaattc aacacaactg tttaatagta cttggaatgt tactgaagag tcaaataaca   7440
ctgtagaaaa taacacaatc acactcccat gcagaataaa acaaattata aacatgtggc   7500
aggaagtagg aagagcaatg tatgcccctc ccatcagagg acaaattaga tgttcatcaa   7560
atattacagg gctgctatta acaagagatg gtggtcctga ggacaacaag accgaggtct   7620
```

```
tcagacctgg aggaggagat atgagggata attggagaag tgaattatat aaatataaag   7680
tagtaaaaat tgaaccatta ggagtagcac ccaccaaggc aaagagaaga gtggtgcaga   7740
gagaaaaaag agcagtggga ataggagctg tgttccttgg gttcttggga gcagcaggaa   7800
gcactatggg cgcagcggca atgacgctga cggtacaggc cagactatta ttgtctggta   7860
tagtgcaaca gcagaacaat ctgctgaggg ctattgaggc gcaacagcat ctgttgcaac   7920
tcacagtctg gggcatcaag cagctccagg caagagtcct ggctgtggaa agatacctaa   7980
gggatcaaca gctcctgggg atttggggtt gctctggaaa actcatctgc accactgctg   8040
tgccttggaa tgctagttgg agtaataaat ctctgaataa gatttgggat aacatgacct   8100
ggatagagtg ggacagagaa attaacaatt acacaagcat aatatacagc ttaattgaag   8160
aatcgcagaa ccaacaagaa aagaatgaac aagaattatt agaattagat aaatgggcaa   8220
gtttgtggaa ttggtttgac ataacaaaat ggctgtggta tataaaaata ttcataatga   8280
tagtaggagg cttgataggt ttaagaatag ttttttctgt actttctata gtgaatagag   8340
ttaggcaggg atactcacca ttatcgtttc agacccacct cccatcctcg aggggacccg   8400
acaggcccgg aggaatcgaa gaagaagtg gagagagaga cagagacaga tccggtccat   8460
tagtgaacgg atccttagca cttatctggg acgatctgcg gagcctgtgc ctcttcagct   8520
accaccgctt gagagactta ctcttgattg taacgaggat tgtggaactt ctgggacgca   8580
gggggtggga agccctcaaa tattggtgga atctcctaca gtattggagt caggaactaa   8640
agaatagtgc tgttaacttg ctcaatgcca cagccatagc agtagctgag gggacagata   8700
gggttataga agtattacaa gcagcttata gagctattcg ccacatacct agaagaataa   8760
gacagggctt ggaaaggatt ttgctataag atggaacacg accttgagag gggcccaccg   8820
ggcccgcgac ggccccctcg aggacccccc ctctcctctt ccctaggcct tgctctcctt   8880
ctcctcctct tggcgctact gttttggctg tacatcgtta tgagtgactg gactggagga   8940
gccctccttg tcctctattc ctttgctctc atgcttataa ttataatttt gatcatcttt   9000
atcttcagaa gagaccttct ctgtccactt ggagcccttt gtatactcct actgatgatc   9060
accctcctgc tcatcgctct ctggaatttg cacggacagg cattgttcct tggaattgtg   9120
ctgttcatct tcgggtgctt acttgtctta ggtatctgga tctacttatt ggagatgctc   9180
tggcgacttg gtgccaccat ctggcagctt ttggccttct tcctagcctt cttcctagac   9240
ctcatcctgc tcattattgc tctctatcta caacaaaact ggtggactct attggttgat   9300
ctcctttggc tcctcctgtt tctggcgatt ttaatctgga tgtattacca tggacaacga   9360
cacagtgatg aacaccacca cgatgactcc ctcccgcacc ctcaacaagc taccgatgat   9420
tctggccatg aatctgactc taactccaac gagggcagac accacctgct cgtgagtgga   9480
gccggcgacg gacccccact ctgctctcaa aacctaggcg cacctggagg tggtcctgac   9540 aatgcccac aggaccctga caacactgat gacaatggcc cacaggaccc tgacaacact   9600
gatgacaatg gcccacatga cccgctgcct caggaccctg acaacactga tgacaatggc   9660
ccacaggacc ctgacaacac tgatgacaat ggcccacatg acccgctgcc tcatagccct   9720
agcgactctg ctggaaatga tggaggccct ccacaattga cggaagaggt tgaaaacaaa   9780
ggaggtgacc agggcccgcc tttgatgaca gacggaggcg gcggtcatag tcatgattcc   9840
ggccatggcg gcggtgatcc acaccttcct acgctgcttt tgggttcttc tggttccggt   9900
ggagatgatg acgaccccca cggcccagtt cagctaagct actatgacta agccgccacc   9960
atggagggtt accccctct ccctcccccc cccctaacgt tactggccga agccgcttgg  10020
```

```
aataaggccg gtgtgcgttt gtctatatgt tattttccac catattgccg tcttttggca    10080
atgtgagggc ccggaaacct ggccctgtct tcttgacgag cattcctagg ggtctttccc    10140
ctctcgccaa aggaatgcaa ggtctgttga atgtcgtgaa ggaagcagtt cctctggaag    10200
cttcttgaag acaaacaacg tctgtagcga ccctttgcag gcagcggaac cccccacctg    10260
gcgacaggtg cctctgcggc caaaagccac gtgtataaga tacacctgca aaggcggcac    10320
aaccccagtg ccacgttgtg agttggatag ttgtggaaag agtcaaatgg ctctcctcaa    10380
gcgtattcaa caaggggctg aaggatgccc agaaggtacc ccattgtatg ggatctgatc    10440
tggggcctcg gtgcacatgc tttacatgtg tttagtcgag gttaaaaaac gtctaggccc    10500
cccgaaccac ggggacgtgg ttttcctttg aaaaacacga tgataatggc cacaaccatg    10560
ggtggcaagt ggtcaaaaag tagtgtgatt ggatggcctg ctgtaaggga agaatgaga    10620 cgagctgagc cagcagcaga tggggtggga gcagtatctc gagacctaga aaacatgga    10680 gcaatcacaa gtagcaatac agcagctaac aatgctgctt gtgcctggct agaagcacaa    10740
gaggaggaag aggtgggttt ccagtcaca cctcaggtac ctttaagacc aatgacttac     10800
aaggcagctg tagatcttag ccactttta aaagaaaagg ggggactgga agggctaatt     10860
cactcccaaa gaagacaaga tatccttgat ctgtggatct accacacaca aggctacttc    10920
cctgattggc agaactacac accagggcca ggggtcagat atccactgac ctttggatgg    10980
tgctacaagc tagtaccagt tgagccagat aaggtagaag aggccaataa aggagagaac    11040
accagcttgt tacaccctgt gagcctgcat ggaatggatg accctgagag agaagtgtta    11100
gagtggaggt ttgacagccg cctagcattt catcacgtgg cccgagagct gcatccggag    11160
tacttcaaga actgctgaca tcgagcttgc tacaagggac tttccgctgg ggactttcca    11220
gggaggcgtg gcctgggcgg gactggggag tggcgagccc tcagatgctg catataagca    11280 gctgctttt gcctgtactg ggtctctctg gttagaccag atctgagcct gggagctctc     11340
tggctaacta gggaacccac tgcttaagcc tcaataaagc ttgccttgag tgcttcaagt    11400
agtgtgtgcc cgtctgttgt gtgactctgg taactagaga tccctcagac ccttttagtc    11460
agtgtggaaa atctctagca a                                              11481

<210> SEQ ID NO 2
<211> LENGTH: 11067
<212> TYPE: DNA
<213> ORGANISM: Artificial Sequence
<220> FEATURE:
<223> OTHER INFORMATION: Synthetic construct

<400> SEQUENCE: 2
tggaagggct aatttggtcc caaaaaagac aagagatcct tgatctgtgg atctaccaca      60
cacaaggcta cttccctgat tggcagaact acacaccagg gccagggatc agatatccac     120
tgacctttgg atggtgcttc aagttagtac cagttgaacc agagcaagta gaagaggcca    180
aataaggaga gaagaacagc ttgttacacc ctatgagcca gcatgggatg gaggacccgg    240
agggagaagt attagtgtgg aagtttgaca gcctcctagc atttcgtcac atggcccgag    300
agctgcatcc ggagtactac aaagactgct gacatcgagc tttctacaag gactttccg    360 ctggggactt ccagggagg tgtggcctgg gcgggactgg ggagtggcga gccctcagat    420
gctacatata agcagctgct ttttgcctgt actgggtctc tctggttaga ccagatctga    480
gcctgggagc tctctggcta actagggaac ccactgctta agcctcaata aagcttgcct    540
```

```
tgagtgctca aagtagtgtg tgcccgtctg ttgtgtgact ctggtaacta gagatccctc    600
agaccctttt agtcagtgtg gaaaatctct agcagtggcg cccgaacagg gacttgaaag    660
cgaaagtaaa gccagaggag atctctcgac gcaggactcg gcttgctgaa gcgcgcacgg    720
caagaggcga gggcggcga ctggtgagta cgccaaaaat tttgactagc ggaggctaga    780
aggagagaga tgggtgcgag agcgtcggta ttaagcgggg gagaattaga taaatgggaa    840
aaaattcggt taaggccagg gggaagaaa caatataaac taaaacatat agtatgggca    900
agcagggagc tagaacgatt cgcagttaat cctggccttt tagagacatc agaaggctgt    960
agacaaatac tgggacagct acaaccatcc cttcagacag gatcagaaga acttagatca   1020
ttatataata caatagcagt cctctattgt gtgcatcaaa ggatagatgt aaaagacacc   1080
aaggaagcct tagataagat agaggaagag caaaacaaaa gtaagaaaaa ggcacagcaa   1140
gcagcagctg acacaggaaa caacagccag gtcagccaaa attaccctat agtgcagaac   1200
ctccaggggc aaatggtaca tcaggccata tcacctagaa ctttaaatgc atgggtaaaa   1260
gtagtagaag agaaggcttt cagcccagaa gtaatacccat tgttttcagc attatcagaa   1320
ggagccaccc cacaagattt aaataccatg ctaaacacag tggggggaca tcaagcagcc   1380
atgcaaatgt taaaagagac catcaatgag gaagctgcag aatgggatag attgcatcca   1440
gtgcatgcag ggcctattgc accaggccag atgagagaac caaggggaag tgacatagca   1500
ggaactacta gtacccttca ggaacaaata ggatggatga cacataatcc acctatccca   1560
gtaggagaaa tctataaaag atggataatc ctgggattaa ataaaatagt aagaatgtat   1620
agccctacca gcattctgga cataagacaa ggaccaaagg aacccttag agactatgta   1680 gaccgattct ataaaactct aagagccgag caagcttcac aagaggtaaa aaattggatg   1740
acagaaacct tgttggtcca aaatgcgaac ccagattgta agactatttt aaaagcattg   1800
ggaccaggag cgacactaga agaaatgatg acagcatgtc agggagtggg gggacccggc   1860
cataaagcaa gagttttggc tgaagcaatg agccaagtaa caaatccagc taccataatg   1920
atacagaaag gcaattttag gaaccaaaga aagactgtta agtgtttcaa ttgtggcaaa   1980
gaagggcaca tagccaaaaa ttgcagggcc cctaggaaaa agggctgttg gaaatgtgga   2040
aaggaaggac accaaatgaa agattgtact gagagacagg ctaattttt agggaagatc   2100 tggccttccc acaagggaag gccagggaat tttcttcaga gcagaccaga gccaacagcc   2160
ccaccagaag agagcttcag gtttggggaa gagacaacaa ctccctctca gaagcaggag   2220
ccgatagaca aggaactgta tcctttagct tccctcagat cactctttgg cagcgacccc   2280
tcgtcacaat aaagataggg gggcaattaa aggaagctct attagataca ggagcagatg   2340
atacagtatt agaagaaatg aatttgccag gaagatggaa accaaaaatg ataggggaa   2400 ttggaggttt tatcaaagta ggacagtatg atcagatact catagaaatc tgcggacata   2460
aagctatagg tacagtatta gtaggaccta cacctgtcaa cataattgga agaaatctgt   2520
tgactcagat tggctgcact ttaaattttc ccattagtcc tattgagact gtaccagtaa   2580
aattaaagcc aggaatggat ggcccaaaag ttaaacaatg gccattgaca gaagaaaaa   2640 taaaagcatt agtagaaatt tgtacagaaa tggaaaagga aggaaaaatt tcaaaaattg   2700
ggcctgaaaa tccatacaat actccagtat ttgccataaa gaaaaaagac agtactaaat   2760
ggagaaaatt agtagatttc agagaactta ataagagaac tcaagatttc tgggaagttc   2820
aattaggaat accacatcct gcagggttaa aacagaaaaa atcagtaaca gtactggatg   2880
tgggcgatgc atattttca gttcccttag ataaagactt caggaagtat actgcattta   2940
```

```
ccatacctag tataaacaat gagacaccag ggattagata tcagtacaat gtgcttccac    3000
agggatggaa aggatcacca gcaatattcc agtgtagcat gacaaaaatc ttagagcctt    3060
ttagaaaaca aaatccagac atagtcatct atcaatacat ggatgatttg tatgtaggat    3120
ctgacttaga aataggggcag catagaacaa aaatagagga actgagacaa catctgttga    3180
ggtggggatt taccacacca gacaaaaaac atcagaaaga acctccattc ctttggatgg    3240
gttatgaact ccatcctgat aaatggacag tacagcctat agtgctgcca gaaaaggaca    3300
gctggactgt caatgacata cagaaattag tgggaaaatt gaattgggca agtcagattt    3360
atgcagggat taaagtaagg caattatgta aacttcttag gggaaccaaa gcactaacag    3420
aagtagtacc actaacagaa gaagcagagc tagaactggc agaaaacagg gagattctaa    3480
aagaaccggt acatggagtg tattatgacc catcaaaaga cttaatagca gaaatacaga    3540
agcaggggca aggccaatgg acatatcaaa tttatcaaga gccatttaaa aatctgaaaa    3600
caggaaaata tgcaagaatg aagggtgccc acactaatga tgtaaaacaa ttaacagagg    3660
cagtacaaaa aatagccaca gaaagcatag taatatgggg aaagactcct aaatttaaat    3720
tacccataca aaaggaaaca tgggaagcat ggtggacaga gtattggcaa gccacctgga    3780
ttcctgagtg ggagtttgtc aatacccctc ccttagtgaa gttatggtac cagttagaga    3840
aagaacccat aataggagca gaaacttttct atgtagatgg ggcagccaat agggaaacta    3900
aattaggaaa agcaggatat gtaactgaca gaggaagaca aaaagttgtc cccctaacgg    3960
acacaacaaa tcagaagact gagttacaag caattcatct agctttgcag gattcgggat    4020
tagaagtaaa catagtgaca gactcacaat atgcattggg aatcattcaa gcacaaccag    4080
ataagagtga atcagagtta gtcagtcaaa taatagagca gttaataaaa aaggaaaaag    4140
tctacctggc atgggtacca gcacacaaag gaattggagg aaatgaacaa gtagatgggt    4200
tggtcagtgc tggaatcagg aaagtactat ttttagatgg aatagataag gcccaagaag    4260
aacatgagaa atatcacagt aattggagag caatggctag tgattttaac ctaccacctg    4320
tagtagcaaa agaaatagta gccagctgtg ataaatgtca gctaaaaggg gaagccatgc    4380
atggacaagt agactgtagc ccaggaatat ggcagctaga ttgtacacat ttagaaggaa    4440
aagttatcct ggtagcagtt catgtagcca gtggatatat agaagcagaa gtaattccag    4500
cagagacagg gcaagaaaca gcatacttcc tcttaaaatt agcaggaaga tggccagtaa    4560
aaacagtaca tacagacaat ggcagcaatt tcaccagtac tacagttaag gccgcctgtt    4620
ggtgggcggg gatcaagcag gaatttggca ttccctacaa tccccaaagt caaggagtaa    4680
tagaatctat gaataaagaa ttaagaaaaa ttataggaca ggtaagagat caggctgaac    4740
atcttaagac agcagtacaa atggcagtat tcatccacaa ttttaaaaga aaaggggggga    4800 ttgggggggta cagtgcaggg gaaagaatag tagacataat agcaacagac atacaaacta    4860
aagaattaca aaaacaaatt acaaaaattc aaaattttcg ggtttattac agggacagca    4920
gagatccagt ttggaaagga ccagcaaagc tcctctggaa aggtgaaggg gcagtagtaa    4980
tacaagataa tagtgacata aaagtagtgc caagaagaaa agcaaagatc atcagggatt    5040
atggaaaaca gatggcaggt gatgattgtg tggcaagtag acaggatgag gattaacaca    5100
tggaaaagat tagtaaaaca ccatatgtat atttcaagga aagctaagga ctggttttat    5160
agacatcact atgaaagtac taatccaaaa ataagttcag aagtacacat cccactaggg    5220
gatgctaaat tagtaataac aacatattgg ggtctgcata caggagaaag agactggcat    5280
```

```
ttgggtcagg gagtctccat agaatggagg aaaaagagat atagcacaca agtagaccct    5340
gacctagcag accaactaat tcatctgcac tattttgatt gttttcaga atctgctata     5400 agaaatacca tattaggacg tatagttagt cctaggtgtg aatatcaagc aggacataac    5460
aaggtaggat ctctacagta cttggcacta gcagcattaa taaaaccaaa acagataaag    5520
ccacctttgc ctagtgttag gaaactgaca gaggacagat ggaacaagcc ccagaagacc    5580
aagggccaca gagggagcca tacaatgaat ggcactaga gcttttagag gaacttaaga    5640
gtgaagctgt tagacatttt cctaggatat ggctccataa cttaggacaa catatctatg    5700
aaacttacgg ggatacttgg gcaggagtgg aagccataat aagaattctg caacaactgc    5760
tgtttatcca tttcagaatt gggtgtcgac atagcaagaa taggtattat tcaacagagg    5820
agagcaagaa atggagccag tagatcctaa actagagccc tggaagcatc caggaagtca    5880
gcctaagact gcttgtacca cttgctattg taaaaagtgt tgctttcatt gccaagtttg    5940
cttcataaca aaaggcttag gcatctccta tggcaggaag aagcggagac agcgacgaag    6000
agctcctcaa gacagtgaga ctcatcaagt ttctctatca aagcagtaag tagtacatgt    6060
aatgcaagct ttacaaatat cagctatagt aggattagta gtagcagcaa taatagcaat    6120
agttgtgtgg accatagtat tcatagaata taggaaaata ttaaggcaaa gaaaatagac    6180
caggttaatt gatagaataa cagaaagagc agaagacagt ggcaatgaga gtgacggaga    6240
tcaggaagag ttatcagcac tggtggagat ggggcatcat gctccttggg atattaatga    6300
tctgtaatgc tgaagaaaaa ttgtgggtca cagtctatta tggggtacct gtgtggaaag    6360
aagcaaccac cactctattt tgtgcatcag atcgtaaagc atatgataca gaggtacata    6420
atgtttgggc cacacatgcc tgtgtaccca cagaccccaa cccacaagaa gtagaattga    6480
aaaatgtgac agaaaatttt aacatgtgga aaaataacat ggtagaacaa atgcatgagg    6540
atataatcag tttatgggat caaagcctaa agccatgtgt aaaattaacc ccactctgtg    6600
ttactttaaa ttgcactgat ttgaggaatg ctactaatgg gaatgacact aataccacta    6660
gtagtagcag gggaatggtg gggggaggag aaatgaaaaa ttgctctttc aatatcacca    6720
caaacataag aggtaaggtg cagaaagaat atgcactttt ttataaactt gatatagcac    6780
caatagataa taatagtaat aatagatata ggttgataag ttgtaacacc tcagtcatta    6840
cacaggcctg tccaaaggta tcctttgagc caattcccat acattattgt gccccggctg    6900
gttttgcgat tctaaagtgt aaagataaga agttcaatgg aaaaggacca tgtacaaatg    6960
tcagcacagt acaatgtaca catggaatta ggccagtagt atcaactcaa ctgctgttaa    7020
atggcagtct agcagaagaa gaggtagtaa ttagatccgc caatttcgcg gacaatgcta    7080
aagtcataat agtacagctg aatgaatctg tagaaattaa ttgtacaaga cccaacaaca    7140
atacaagaaa aagtatacat ataggaccag gcagagcatt ttatacaaca ggagaaataa    7200
taggagatat aagacaagca cattgtaacc ttagtagagc aaaatggaat gacactttaa    7260
ataagatagt tataaaatta agagaacaat ttgggaataa acaatagtc tttaagcact    7320 cctcaggagg ggacccagaa attgtgacgc acagttttaa ttgtggaggg gaatttttct    7380
actgtaattc aacacaactg tttaatagta cttggaatgt tactgaagag tcaaataaca    7440
ctgtagaaaa taacacaatc acactcccat gcagaataaa acaaattata aacatgtggc    7500
aggaagtagg aagagcaatg tatgcccctc ccatcagagg acaaattaga tgttcatcaa    7560
atattacagg gctgctatta acaagagatg gtggtcctga ggacaacaag accgaggtct    7620
tcagacctgg aggaggagat atgagggata attggagaag tgaattatat aaatataaag    7680
```

-continued

```
tagtaaaaat tgaaccatta ggagtagcac ccaccaaggc aaagagaaga gtggtgcaga       7740
gagaaaaaag agcagtggga ataggagctg tgttccttgg gttcttggga gcagcaggaa       7800
gcactatggg cgcagcggca atgacgctga cggtacaggc cagactatta ttgtctggta       7860
tagtgcaaca gcagaacaat ctgctgaggg ctattgaggc gcaacagcat ctgttgcaac       7920
tcacagtctg gggcatcaag cagctccagg caagagtcct ggctgtggaa agatacctaa       7980
gggatcaaca gctcctgggg atttggggtt gctctggaaa actcatctgc accactgctg       8040
tgccttggaa tgctagttgg agtaataaat ctctgaataa gatttgggat aacatgacct       8100
ggatagagtg ggacagagaa attaacaatt acacaagcat aatatacagc ttaattgaag       8160
aatcgcagaa ccaacaagaa aagaatgaac aagaattatt agaattagat aaatgggcaa       8220
gtttgtggaa ttggtttgac ataacaaaat ggctgtggta tataaaaata ttcataatga       8280
tagtaggagg cttgataggt ttaagaatag ttttttctgt actttctata gtgaatagag       8340
ttaggcaggg atactcacca ttatcgtttc agacccacct cccatcctcg aggggacccg       8400
acaggcccgg aggaatcgaa gaagaaggtg gagagagaga cagagacaga tccggtccat       8460
tagtgaacgg atccttagca cttatctggg acgatctgcg gagcctgtgc ctcttcagct       8520
accaccgctt gagagactta ctcttgattg taacgaggat tgtggaactt ctgggacgca       8580
gggggtggga agccctcaaa tattggtgga atctcctaca gtattggagt caggaactaa       8640
agaatagtgc tgttaacttg ctcaatgcca cagccatagc agtagctgag gggacagata       8700
gggttataga agtattacaa gcagcttata gagctattcg ccacatacct agaagaataa       8760
gacagggctt ggaaaggatt tgctataag atggaacacg accttgagag gggcccaccg       8820
ggcccgcgac ggccccctcg aggacccccc ctctcctctt ccctaggcct tgctctcctt       8880
ctcctcctct tggcgctact gttttggctg tacatcgtta tgagtgactg gactggagga       8940
gccctccttg tcctctattc ctttgctctc atgcttataa ttataatttt gatcatcttt       9000
atcttcagaa gagaccttct ctgtccactt ggagcccttt gtatactcct actgatgatc       9060
accctcctgc tcatcgctct ctggaatttg cacggacagg cattgttcct tggaattgtg       9120
ctgttcatct tcgggtgctt acttgtctta ggtatctgga tctacttatt ggagatgctc       9180
tggcgacttg gtgccaccat ctggcagctt ttggccttct tcctagcctt cttcctagac       9240
ctcatcctgc tcattattgc tctctatcta caacaaaact ggtggactct attggttgat       9300
ctcctttggc tcctcctgtt tctggcgatt ttaatctgga tgtattacca tggacaacga       9360
aagaagccaa ccaataaggc ccccacccc aagcaggaac cccaggagat caattttccc       9420
gacgatcttc ctggctccaa cactgctgct ccagtgcagg agactttaca tggatgccaa       9480
ccggtcaccc aggaggatgg caaagagagt cgcatctcag tgcaggagag acagtgagcc       9540
gccaccatgg agggttaccc ccctctccct ccccccccc taacgttact ggccgaagcc       9600
gcttggaata aggccggtgt gcgtttgtct atatgttatt ttccaccata ttgccgtctt       9660
ttggcaatgt gagggcccgg aaacctggcc ctgtcttctt gacgagcatt cctaggggtc       9720
tttcccctct cgccaaagga atgcaaggtc tgttgaatgt cgtgaaggaa gcagttcctc       9780
tggaagcttc ttgaagacaa acaacgtctg tagcgaccct ttgcaggcag cggaaccccc       9840
cacctggcga caggtgcctc tgcggccaaa agccacgtgt ataagataca cctgcaaagg       9900
cggcacaacc ccagtgccac gttgtgagtt ggatagttgt ggaaagagtc aaatggctct       9960
cctcaagcgt attcaacaag gggctgaagg atgcccagaa ggtaccccat tgtatgggat      10020
```

```
ctgatctggg gcctcggtgc acatgcttta catgtgttta gtcgaggtta aaaaacgtct    10080
aggccccccg aaccacgggg acgtggtttt cctttgaaaa acacgatgat aatggccaca    10140
accatgggtg gcaagtggtc aaaaagtagt gtgattggat ggcctgctgt aagggaaaga    10200
atgagacgag ctgagccagc agcagatggg gtgggagcag tatctcgaga cctagaaaaa    10260
catggagcaa tcacaagtag caatacagca gctaacaatg ctgcttgtgc ctggctagaa    10320
gcacaagagg aggaagaggt gggttttcca gtcacacctc aggtaccttt aagaccaatg    10380
acttacaagg cagctgtaga tcttagccac ttttaaaag aaaagggggg actggaaggg    10440
ctaattcact cccaaagaag acaagatatc cttgatctgt ggatctacca cacacaaggc    10500
tacttccctg attggcagaa ctacacacca gggccagggg tcagatatcc actgaccttt    10560
ggatggtgct acaagctagt accagttgag ccagataagg tagaagaggc caataaagga    10620
gagaacacca gcttgttaca ccctgtgagc ctgcatggaa tggatgaccc tgagagagaa    10680
gtgttagagt ggaggtttga cagccgccta gcatttcatc acgtggcccg agagctgcat    10740
ccggagtact tcaagaactg ctgacatcga gcttgctaca agggactttc cgctggggac    10800
tttccaggga ggcgtggcct gggcgggact ggggagtggc gagccctcag atgctgcata    10860
taagcagctg cttttttgcct gtactgggtc tctctggtta ccagatct gagcctggga     10920 gctctctggc taactaggga acccactgct aagcctcaa taaagcttgc cttgagtgct    10980
tcaagtagtg tgtgcccgtc tgttgtgtga ctctggtaac tagagatccc tcagacccctt   11040 ttagtcagtg tggaaaatct ctagcaa                                        11067

<210> SEQ ID NO 3
<211> LENGTH: 15
<212> TYPE: PRT
<213> ORGANISM: Artificial Sequence
<220> FEATURE:
<223> OTHER INFORMATION: Synthetic construct

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 23
<212> TYPE: PRT
<213> ORGANISM: Artificial Sequence
<220> FEATURE:
<223> OTHER INFORMATION: Synthetic construct

<400> SEQUENCE: 4

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gtctgtgctg atcccagtga                                                     20

<210> SEQ ID NO 6
```

```
<211> LENGTH: 20
<212> TYPE: DNA
<213> ORGANISM: Artificial Sequence
<220> FEATURE:
<223> OTHER INFORMATION: Primer

<400> SEQUENCE: 6
ttgtcaccag acgcggtgtg                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gtctgtgctg atcccagtga                                               20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ggacacttat cctttggcta                                               20

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ccgcggcagc cctcgctgtc atcc                                          24

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
catctccaaa gagttgatgt actcc                                         25

<210> SEQ ID NO 11
<211> LENGTH: 570
<212> TYPE: DNA
<213> ORGANISM: Epstein-Barr Virus

<400> SEQUENCE: 11
atggaacacg accttgagag gggcccaccg ggcccgcgac ggcccccctcg aggacccccc    60 ctctcctctt ccctaggcct tgctctcctt ctcctcctct tggcgctact gttttggctg   120
tacatcgtta tgagtgactg gactggagga gccctccttg tcctctattc ctttgctctc   180
atgcttataa ttataatttt gatcatcttt atcttcagaa gagaccttct ctgtccactt   240
ggagcccttt gtatactcct actgatgatc accctcctgc tcatcgctct ctggaatttg   300
cacggacagg cattgttcct tggaattgtg ctgttcatct tcgggtgctt acttgtctta   360
ggtatctgga tctacttatt ggagatgctc tggcgacttg gtgccaccat ctggcagctt   420
```
ttggccttct tcctagcctt cttcctagac ctcatcctgc tcattattgc tctctatcta      480
caacaaaact ggtggactct attggttgat ctcctttggc tcctcctgtt tctggcgatt      540
ttaatctgga tgtattacca tggacaacga                                        570

<210> SEQ ID NO 12
<211> LENGTH: 177
<212> TYPE: DNA
<213> ORGANISM: Homo sapiens

<400> SEQUENCE: 12
aagaagccaa ccaataaggc cccccacccc aagcaggaac cccaggagat caattttccc       60
gacgatcttc ctggctccaa cactgctgct ccagtgcagg agactttaca tggatgccaa      120
ccggtcaccc aggaggatgg caaagagagt cgcatctcag tgcaggagag acagtga        177

<210> SEQ ID NO 13
<211> LENGTH: 6184
<212> TYPE: DNA
<213> ORGANISM: Artificial Sequence
<220> FEATURE:
<223> OTHER INFORMATION: Synthetic construct

<400> SEQUENCE: 13
gaattcgttg gtggtcgcca tggatggtgt tattgtatac tgtctaaacg cgttagtaaa       60
acatggcgag gaaataaatc atataaaaaa tgatttcatg attaaaccat gttgtgaaaa      120
agtcaagaac gttcacattg gcggacaatc taaaaacaat acagtgattg cagatttgcc      180
atatatggat aatgcggtat ccgatgtatg caattcactg tataaaaaga atgtatcaag      240
aatatccaga tttgctaatt tgataaagat agatgacgat gacaagactc ctactggtgt      300
atataattat tttaaaccta agatgccat tcctgttatt atatccatag aaaggatag       360 agatgtttgt gaactattaa tctcatctga taaagcgtgt gcgtgtatag agttaaattc      420
atataaagta gccattcttc ccatggatgt ttcctttttt accaaaggaa atgcatcatt      480
gattattctc ctgtttgatt tctctatcga tgcggcacct ctcttaagaa gtgtaaccga      540
taataatgtt attatatcta gacaccagcg tctacatgac gagcttccga gttccaattg      600
gttcaagttt tacataagta taagtccga ctattgttct atattatata tggttgttga       660
tggatctgtg atgcatgcaa tagctgataa tagaaactta gcaaatatta gcaaaaatat      720
attagacaat actacaatta acgatgagtg tagatgctgt tattttgaac cacagattag      780
gattcttgat agagatgaga tgctcaatgg atcatcgtgt gatatgaaca gacattgtat      840
tatgatgaat ttacctgatg taggcgaatt tggatctagt atgttgggga aatatgaacc      900
tgacatgatt aagattgctc tttcggtggc tgggtaccag gcgcgccttt cattttgttt      960
ttttctatgc tataaatggt gagcaagggc gaggagctgt tcaccggggt ggtgcccatc     1020
ctggtcgagc tggacggcga cgtaaacggc cacaagttca gcgtgtccgg cgagggcgag     1080
ggcgatgcca cctacggcaa gctgaccctg aagttcatct gcaccaccgg caagctgccc     1140
gtgccctggc ccaccctcgt gaccaccctg acctacggcg tgcagtgctt cagccgctac     1200
cccgaccaca tgaagcagca cgacttcttc aagtccgcca tgcccgaagg ctacgtccag     1260
gagcgcacca tcttcttcaa ggacgacggc aactacaaga cccgcgccga ggtgaagttc     1320
gagggcgaca ccctggtgaa ccgcatcgag ctgaagggca tcgacttcaa ggaggacggc     1380
aacatcctgg ggcacaagct ggagtacaac tacaacagcc acaacgtcta tatcatggcc     1440

```
gacaagcaga agaacggcat caaggtgaac ttcaagatcc gccacaacat cgaggacggc     1500
agcgtgcagc tcgccgacca ctaccagcag aacaccccca tcggcgacgg ccccgtgctg     1560
ctgcccgaca ccactacct gagcacccag tccgccctga gcaaagaccc caacgagaag      1620
cgcgatcaca tggtcctgct ggagttcgtg accgccgccg ggatcactct cggcatgcac     1680
gagctgtaca agtaagcggc cgctggtacc caacctaaaa attgaaaata aatacaaagg     1740
ttcttgaggg ttgtgttaaa ttgaaagcga gaaataatca taaataagcc cggggatgcc     1800
gccaccatgg aacacgacct tgagaggggc ccaccgggcc cgcgacggcc ccctcgagga     1860 cccccctct cctcttccat aggccttgct ctccttctcc tgctcttggc gctactgttt      1920
tggctgtaca tcattatgag taactggact ggaggagccc tccttgtcct ctatgccttt     1980
gctctcatgc ttgtgattat cattttgatc atctttatct tcagaagaga ccttctctgt     2040
ccacttggag ccctttgtct actcctactg atgatcaccc tcctgctcat cgctctctgg     2100
aatttgcacg acaggcatt gtaccttgga attgtgctgt tcatcttcgg gtgcttactt      2160
gtcttaggtc tctggatcta cttattggag attctctggc gacttggtgc caccatctgg     2220
cagcttttgg ccttcttcct agccttcttc ctagacatca tcctgctcat tattgctctc    2280
tatctacaac aaaactggtg gactctattg gttgatctcc tttggctcct cctgtttctg     2340
gcgattttaa tctggatgta ttaccatgga caacgacaca gtgatgaaca ccaccacgat     2400
gactccctcc cgcacccctca acaagctacc gatgattcta gcaatcaatc tgactctaac    2460
tccaacgagg gcagacacct cctgctcgtg agtggagccg gcgacggacc cccactctgc     2520
tctcaaaacc taggcgcacc tggaggtggt cctaacaatg gcccacagga ccctgacaac     2580
actgatgaca atggcccaca ggaccctgac aacactgatg acaatggccc acatgacccg     2640
ctgcctcagg accctgacaa cactgatgac aatggcccac aggaccctga acactgat      2700 gacaatggcc cacatgaccc gctgcctcat aaccctagcg actctgctgg aaatgatgga     2760
ggccctccac aattgacgga agaggtggaa acaaaggag gtgaccaggg cccgcctttg      2820
atgacagacg gtggcggcgg tcatagtcat gattccggcc atgacggcat agatccacac     2880
cttcctacgc tgcttttggg tacttctggt tccggtggag atgatgacga cccccacggc     2940
ccagttcagc taagctacta tgactaactg cagggaaagt tttataggta gttgatagaa     3000
caaaatacat aattttgtaa aaataaatca ctttttatac taatatgaca cgattaccaa     3060 tactttgtt actaatatca ttagtatacg ctacacctt tcctcagaca tctaaaaaaa       3120
taggtgatga tgcaacttta tcatgtaatc gaaataatac aaatgactac gttgttatga     3180
gtgcttggta taaggagccc aattccatta ttctttagc tgctaaaagc gacgtcttgt      3240
attttgataa ttataccaag gataaaatat cttacgactc tccatacgat gatctagtta     3300
caactatcac aattaaatca ttgactgcta gagatgccgg tacttatgta tgtgcattct     3360
ttatgacatc gcctacaaat gacactgata agtagatta tgaagaatac tccacagagt     3420
tgattgtaaa tacagatagt gaatcgacta tagacataat actatctgga tctacacatt    3480
caccagaaac tagttaagct tgtctcccta tagtgagtcg tattagagct ggcgtaatc     3540 atggtcatag ctgtttcctg tgtgaaattg ttatccgctc acaattccac acaacatacg    3600
agccggaagc ataaagtgta aagcctgggg tgcctaatga gtgagctaac tcacattaat    3660
tgcgttgcgc tcactgcccg ctttcgagtc gggaaacctg tcgtgccagc tgcattaatg    3720
aatcggccaa cgcgcgggga gaggcggttt gcgtattggg cgctcttccg cttcctcgct    3780
cactgactcg ctgcgctcgg tcgttcggct gcggcgagcg gtatcagctc actcaaaggc    3840
```

```
ggtaatacgg ttatccacag aatcagggga taacgcagga agaacatgt gagcaaaagg    3900
ccagcaaaag gccaggaacc gtaaaaaggc cgcgttgctg cgttttccg ataggctccg    3960
ccccctgac gagcatcaca aaaatcgacg ctcaagtcag aggtggcgaa acccgacagg    4020
actataaaga taccaggcgt ttccccctgg aagctccctc gtgcgctctc ctgttccgac    4080
cctgccgctt accggatacc tgtccgcctt tctcccttcg ggaagcgtgg cgctttctca    4140
tagctcacgc tgtaggtatc tcagttcggt gtaggtcgtt cgctccaagc tgggctgtgt    4200
gcacgaaccc cccgttcagc ccgaccgctg cgccttatcc ggtaactatc gtcttgagtc    4260
caacccggta agacacgact tatcgccact ggcagcagcc actggtaaca ggattagcag    4320
agcgaggtat gtaggcggtg ctacagagtt cttgaagtgg tggcctaact acggctacac    4380
tagaaggaca gtatttggta tctgcgctct gctgaagcca gttaccttcg aaaaagagt    4440
tggtagctct tgatccggca aacaaaccac cgctggtagc ggtggttttt tgtttgcaa    4500
gcagcagatt acgcgcagaa aaaaggatc tcaagaagat cctttgatct tttctacggg    4560
gtctgacgct cagtggaacg aaaactcacg ttaagggatt ttggtcatga gattatcaaa    4620
aaggatcttc acctagatcc ttttaaatta aaaatgaagt tttaaatcaa tctaaagtat    4680
atatgagtaa acttggtctg acagttacca atgcttaatc agtgaggcac ctatctcagc    4740
gatctgtcta tttcgttcat ccatagttgc ctgactcccc gtcgtgtaga taactacgat    4800
acgggagggc ttaccatctg gccccagtgc tgcaatgata ccgcgagacc cacgctcacc    4860
ggctccagat ttatcagcaa taaaccagcc agccggaagg gccgagcgca gaagtggtcc    4920
tgcaacttta tccgcctcca tccagtctat taattgttgc cgggaagcta gagtaagtag    4980
ttcgccagtt aatagtttgc gcaacgttgt tggcattgct acaggcatcg tggtgtcacg    5040
ctcgtcgttt ggtatggctt cattcagctc cggttcccaa cgatcaaggc gagttacatg    5100
atcccccatg ttgtgcaaaa aagcggttag ctccttcggt cctccgatcg ttgtcagaag    5160
taagttggcc gcagtgttat cactcatggt tatggcagca ctgcataatt ctcttactgt    5220
catgccatcc gtaagatgct tttctgtgac tggtgagtac tcaaccaagt cattctgaga    5280
atagtgtatg cggcgaccga gttgctcttg cccggcgtca atacgggata ataccgcgcc    5340
acatagcaga actttaaaag tgctcatcat tggaaaacgt tcttcggggc gaaaactctc    5400
aaggatctta ccgctgttga gatccagttc gatgtaaccc actcgtgcac ccaactgatc    5460
ttcagcatct tttactttca ccagcgtttc tgggtgagca aaaacaggaa ggcaaaatgc    5520
cgcaaaaaag ggaataaggg cgacacggaa atgttgaata ctcatactct tcctttttca    5580
atattattga agcatttatc agggttattg tctcatgagc ggatacatat ttgaatgtat    5640
ttagaaaaat aaacaaatag gggttccgcg cacatttccc cgaaaagtgc cacctgacgt    5700
ctaagaaacc attattatca tgacattaac ctataaaaat aggcgtatca cgaggccctt    5760
tcgtctcgcg cgtttcggtg atgacggtga aaacctctga cacatgcagc tcccggagac    5820
ggtcacagct tgtctgtaag cggatgccgg gagcagacaa gcccgtcagg gcgcgtcagc    5880
gggtgttggc gggtgtcggg gctggcttaa ctatgcggca tcagagcaga ttgtactgag    5940
agtgcaccat atgcggtgtg aaataccgca cagatgcgta aggagaaaat accgcatcag    6000
gcgccattcg ccattcaggc tgcgcaactg ttgggaaggg cgatcggtgc gggcctcttc    6060
gctattacgc cagctggcga aggggggatg tgctgcaagg cgattaagtt gggtaacgcc    6120
agggttttcc cagtcacgac gttgtaaaac gacggccagt gaattggatt taggtgacac    6180
```

-continued

| | |
|---|---|
| tata | 6184 |

<210> SEQ ID NO 14
<211> LENGTH: 5775
<212> TYPE: DNA
<213> ORGANISM: Artificial Sequence
<220> FEATURE:
<223> OTHER INFORMATION: Synthetic construct

<400> SEQUENCE: 14

| | |
|---|---|
| gaattcgttg gtggtcgcca tggatggtgt tattgtatac tgtctaaacg cgttagtaaa | 60 |
| acatggcgag gaaataaatc atataaaaaa tgatttcatg attaaaccat gttgtgaaaa | 120 |
| agtcaagaac gttcacattg gcggacaatc taaaaacaat acagtgattg cagatttgcc | 180 |
| atatatggat aatgcggtat ccgatgtatg caattcactg tataaaaga atgtatcaag | 240 |
| aatatccaga tttgctaatt tgataaagat agatgacgat gacaagactc ctactggtgt | 300 |
| atataattat tttaaaccta agatgccat tcctgttatt atatccatag gaaaggatag | 360 |
| agatgtttgt gaactattaa tctcatctga taaagcgtgt gcgtgtatag agttaaattc | 420 |
| atataaagta gccattcttc ccatggatgt ttccttttt accaaaggaa atgcatcatt | 480 |
| gattattctc ctgtttgatt tctctatcga tgcggcacct ctcttaagaa gtgtaaccga | 540 |
| taataatgtt attatatcta gacaccagcg tctacatgac gagcttccga gttccaattg | 600 |
| gttcaagttt tacataagta taaagtccga ctattgttct atattatata tggttgttga | 660 |
| tggatctgtg atgcatgcaa tagctgataa tagaacttac gcaaatatta gcaaaaatat | 720 |
| attagacaat actacaatta acgatgagtg tagatgctgt tattttgaac cacagattag | 780 |
| gattcttgat agagatgaga tgctcaatgg atcatcgtgt gatatgaaca gacattgtat | 840 |
| tatgatgaat ttacctgatg taggcgaatt tggatctagt atgttgggga aatatgaacc | 900 |
| tgacatgatt aagattgctc tttcggtggc tgggtaccag gcgcgccttt cattttgttt | 960 |
| ttttctatgc tataaatggt gagcaagggc gaggagctgt tcaccggggt ggtgcccatc | 1020 |
| ctggtcgagc tggacggcga cgtaaacggc cacaagttca gcgtgtccgg cgagggcgag | 1080 |
| ggcgatgcca cctacggcaa gctgaccctg aagttcatct gcaccaccgg caagctgccc | 1140 |
| gtgccctggc ccaccctcgt gaccaccctg acctacggcg tgcagtgctt cagccgctac | 1200 |
| cccgaccaca tgaagcagca cgacttcttc aagtccgcca tgcccgaagg ctacgtccag | 1260 |
| gagcgcacca tcttcttcaa ggacgacggc aactacaaga cccgcgccga ggtgaagttc | 1320 |
| gagggcgaca ccctggtgaa ccgcatcgag ctgaagggca tcgacttcaa ggaggacggc | 1380 |
| aacatcctgg ggcacaagct ggagtacaac tacaacagcc acaacgtcta tatcatggcc | 1440 |
| gacaagcaga agaacggcat caaggtgaac ttcaagatcc gccacaacat cgaggacggc | 1500 |
| agcgtgcagc tcgccgacca ctaccagcag aacaccccca tcggcgacgg ccccgtgctg | 1560 |
| ctgcccgaca accactacct gagcacccag tccgccctga gcaaagaccc caacgagaag | 1620 |
| cgcgatcaca tggtcctgct ggagttcgtg accgccgccg ggatcactct cggcatgcac | 1680 |
| gagctgtaca gtaagcggc cgctggtacc caacctaaaa attgaaaata aatacaaagg | 1740 |
| ttcttgaggg ttgtgttaaa ttgaaagcga gaaataatca taataagcc cggggatcca | 1800 |
| tggaacacga ccttgagagg ggcccaccgg gccgcgacg gcccctcga ggaccccccc | 1860 |
| tctcctcttc cataggcctt gctctccttc tcctgctctt ggcgctactg ttttggctgt | 1920 |
| acatcattat gagtaactgg actggaggag ccctccttgt cctctatgcc tttgctctca | 1980 |
| tgcttgtgat tatcattttg atcatcttta tcttcagaag agaccttctc tgtccacttg | 2040 |

```
gagcccttty tctactccta ctgatgatca ccctcctgct catcgctctc tggaatttgc    2100
acggacaggc attgtaccct ggaattgtgc tgttcatctt cgggtgctta cttgtcttag    2160
gtctctggat ctacttattg gagattctct ggcgacttgg tgccaccatc tggcagcttt    2220
tggccttctt cctagccttc ttcctagaca tcatcctgct cattattgct ctctatctac    2280
aacaaaactg gtggactcta ttggttgatc tcctttggct cctcctgttt ctggcgattt    2340
taatctggat gtattaccat ggacaacgaa aaaaggtggc caagaagcca accaataagg    2400
ccccccaccc caagcaggaa ccccaggaga tcaattttcc cgacgatctt cctggctcca    2460
acactgctgc tccagtgcag gagactttac atggatgcca accggtcacc caggaggatg    2520
gcaaagagag tcgcatctca gtgcaggaga cagtgact gcagggaaag ttttataggt    2580
agttgataga acaaaataca taattttgta aaaataaatc acttttata ctaatatgac    2640 acgattacca atacttttgt tactaatatc attagtatac gctacacctt ttcctcagac    2700
atctaaaaaa ataggtgatg atgcaacttt atcatgtaat cgaaataata caaatgacta    2760
cgttgttatg agtgcttggt ataaggagcc caattccatt attcttttag ctgctaaaag    2820
cgacgtcttg tattttgata attataccaa ggataaaata tcttacgact ctccatacga    2880
tgatctagtt acaactatca caattaaatc attgactgct agagatgccg gtacttatgt    2940
atgtgcattc tttatgacat cgcctacaaa tgacactgat aaagtagatt atgaagaata    3000
ctccacagag ttgattgtaa atacagatag tgaatcgact atagacataa tactatctgg    3060
atctacacat tcaccagaaa ctagttaagc ttgtctccct atagtgagtc gtattagagc    3120
ttggcgtaat catggtcata gctgtttcct gtgtgaaatt gttatccgct cacaattcca    3180
cacaacatac gagccggaag cataaagtgt aaagcctggg gtgcctaatg agtgagctaa    3240
ctcacattaa ttgcgttgcg ctcactgccc gctttcgagt cgggaaaccct gtcgtgccag    3300 ctgcattaat gaatcggcca acgcgcgggg agaggcggtt tgcgtattgg gcgctcttcc    3360
gcttcctcgc tcactgactc gctgcgctcg tcgttcggc tgcggcgagc ggtatcagct    3420
cactcaaagg cggtaatacg gttatccaca gaatcagggg ataacgcagg aaagaacatg    3480
tgagcaaaag gccagcaaaa ggccaggaac cgtaaaaagg ccgcgttgct ggcgtttttc    3540
gataggctcc gcccccctga cgagcatcac aaaaatcgac gctcaagtca gaggtggcga    3600
aacccgacag gactataaag ataccaggcg tttccccctg gaagctccct cgtgcgctct    3660
cctgttccga ccctgccgct taccggatac ctgtccgcct ttctcccttc gggaagcgtg    3720
gcgctttctc atagctcacg ctgtaggtat ctcagttcgg tgtaggtcgt tcgctccaag    3780
ctgggctgtg tgcacgaacc ccccgttcag cccgaccgct gcgccttatc cggtaactat    3840
cgtcttgagt ccaacccggt aagacacgac ttatcgccac tggcagcagc cactggtaac    3900
aggattagca gagcgaggta tgtaggcggt gctacagagt tcttgaagtg gtggcctaac    3960
tacggctaca ctagaaggac agtatttggt atctgcgctc tgctgaagcc agttaccttc    4020
ggaaaaagag ttggtagctc ttgatccggc aaacaaacca ccgctggtag cggtggtttt    4080
tttgtttgca agcagcagat tacgcgcaga aaaaaaggat ctcaagaaga tcctttgatc    4140
ttttctacgg ggtctgacgc tcagtggaac gaaaactcac gttaagggat tttggtcatg    4200
agattatcaa aaaggatctt cacctagatc cttttaaatt aaaaatgaag ttttaaatca    4260
atctaaagta tatatgagta aacttggtct gacagttacc aatgcttaat cagtgaggca    4320
cctatctcag cgatctgtct atttcgttca tccatagttg cctgactccc cgtcgtgtag    4380
```

```
ataactacga tacgggaggg cttaccatct ggccccagtg ctgcaatgat accgcgagac    4440
ccacgctcac cggctccaga tttatcagca ataaaccagc cagccggaag ggccgagcgc    4500
agaagtggtc ctgcaacttt atccgcctcc atccagtcta ttaattgttg ccgggaagct    4560
agagtaagta gttcgccagt taatagtttg cgcaacgttg ttggcattgc tacaggcatc    4620
gtggtgtcac gctcgtcgtt tggtatggct tcattcagct ccggttccca acgatcaagg    4680
cgagttacat gatcccccat gttgtgcaaa aaagcggtta gctccttcgg tcctccgatc    4740
gttgtcagaa gtaagttggc cgcagtgtta tcactcatgg ttatggcagc actgcataat    4800
tctcttactg tcatgccatc cgtaagatgc ttttctgtga ctggtgagta ctcaaccaag    4860
tcattctgag aatagtgtat gcggcgaccg agttgctctt gcccggcgtc aatacgggat    4920
aataccgcgc cacatagcag aactttaaaa gtgctcatca ttggaaaacg ttcttcgggg    4980
cgaaaactct caaggatctt accgctgttg agatccagtt cgatgtaacc cactcgtgca    5040
cccaactgat cttcagcatc ttttactttc accagcgttt ctgggtgagc aaaaacagga    5100
aggcaaaatg ccgcaaaaaa gggaataagg gcgacacgga aatgttgaat actcatactc    5160
ttcctttttc aatattattg aagcatttat cagggttatt gtctcatgag cggatacata    5220
tttgaatgta tttagaaaaa taaacaaata ggggttccgc gcacatttcc ccgaaaagtg    5280
ccacctgacg tctaagaaac cattattatc atgacattaa cctataaaaa taggcgtatc    5340
acgaggccct ttcgtctcgc gcgtttcggt gatgacggtg aaaacctctg acacatgcag    5400
ctcccggaga cggtcacagc ttgtctgtaa gcggatgccg ggagcagaca gcccgtcag     5460 ggcgcgtcag cgggtgttgg cgggtgtcgg ggctggctta actatgcggc atcagagcag    5520
attgtactga gagtgcacca tatgcggtgt gaaataccgc acagatgcgt aaggagaaaa    5580
taccgcatca ggcgccattc gccattcagg ctgcgcaact gttgggaagg gcgatcggtg    5640
cgggcctctt cgctattacg ccagctggcg aaagggggat gtgctgcaag gcgattaagt    5700
tgggtaacgc cagggttttc ccagtcacga cgttgtaaaa cgacggccag tgaattggat    5760
ttaggtgaca ctata                                                     5775
```